(12) United States Patent
Tamai et al.

(10) Patent No.: US 11,969,459 B2
(45) Date of Patent: Apr. 30, 2024

(54) THERAPEUTIC AGENT FOR CARDIOMYOPATHY, OLD MYOCARDIAL INFARCTION AND CHRONIC HEART FAILURE

(71) Applicants: StemRIM Inc., Osaka (JP); OSAKA UNIVERSITY, Osaka (JP)

(72) Inventors: Katsuto Tamai, Osaka (JP); Yoshiki Sawa, Osaka (JP); Shigeru Miyagawa, Osaka (JP); Takashi Kido, Osaka (JP); Takasumi Goto, Osaka (JP); Takehiko Yamazaki, Osaka (JP)

(73) Assignees: StemRIM Inc., Osaka (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 16/477,878

(22) PCT Filed: Jan. 26, 2018

(86) PCT No.: PCT/JP2018/002373
§ 371 (c)(1),
(2) Date: Jul. 13, 2019

(87) PCT Pub. No.: WO2018/139562
PCT Pub. Date: Aug. 2, 2018

(65) Prior Publication Data
US 2019/0343924 A1 Nov. 14, 2019

(30) Foreign Application Priority Data

Jan. 27, 2017 (JP) ................................. 2017-013293
Aug. 4, 2017 (JP) ................................. 2017-151788

(51) Int. Cl.
| | |
|---|---|
| *A61K 38/00* | (2006.01) |
| *A61K 38/19* | (2006.01) |
| *A61P 9/10* | (2006.01) |
| *C07K 14/00* | (2006.01) |

(52) U.S. Cl.
CPC ................ *A61K 38/19* (2013.01); *A61P 9/10* (2018.01)

(58) Field of Classification Search
CPC .................................. A61K 38/19; A61P 9/10
See application file for complete search history.

(56) References Cited

U.S. PATENT DOCUMENTS

| | | | |
|---|---|---|---|
| 3,896,810 A | 7/1975 | Akiyama | |
| 4,732,155 A | 3/1988 | Zetter et al. | |
| 5,661,127 A | 8/1997 | Bhatnagar et al. | |
| 5,851,986 A | 12/1998 | Takada et al. | |
| 5,902,799 A | 5/1999 | Herrmann et al. | |
| 6,723,319 B1 | 4/2004 | Ito et al. | |
| 6,905,874 B2 | 6/2005 | Berenson et al. | |
| 7,220,723 B2 | 5/2007 | Tracey et al. | |
| 7,288,250 B2 | 10/2007 | Newman et al. | |
| 7,446,100 B2 | 11/2008 | Pilarski | |
| 7,470,538 B2 | 12/2008 | Laughlin et al. | |
| 7,585,504 B2 | 9/2009 | Wu et al. | |
| 7,632,802 B2 | 12/2009 | Tessier et al. | |
| 7,749,959 B2 | 7/2010 | Tracey et al. | |
| 7,833,975 B2 | 11/2010 | Okazawa | |
| 7,939,057 B2 | 5/2011 | Battista et al. | |
| 8,114,668 B2 | 2/2012 | Stolen et al. | |
| 8,119,121 B2 | 2/2012 | Fraser et al. | |
| 8,551,470 B2 | 10/2013 | Son et al. | |

(Continued)

FOREIGN PATENT DOCUMENTS

| | | |
|---|---|---|
| AU | 2003228099 A1 | 1/2004 |
| AU | 2004203732 A1 | 7/2004 |

(Continued)

OTHER PUBLICATIONS

"Cardiomegaly" Merriam Webster, 2015 archived page, accessed via Wayback Machine [online] [accessed at https://web.archive.org/web/20150107154504/https://www.merriam-webster.com/medical/cardiomegaly on May 21, 2020]. (Year: 2015).*
Narumi, T. et al. "High-mobility group box 1-mediated heat shock protein beta 1 expression attenuates mitochondrial dysfunction and apoptosis". 2015. Journal of Molecular and Cellular Cardiology, 82, pp. 1-12. (Year: 2015).*
Takahashi, K. et al. "Modulated Inflammation by Injection of High-Mobility Group Box 1 Recovers Post-Infarction Chronically Failing Heart". 2008. 118[suppl 1]:S106-S114. (Year: 2008).*

(Continued)

*Primary Examiner* — Elizabeth C. Kemmerer
*Assistant Examiner* — Regina M DeBerry
(74) *Attorney, Agent, or Firm* — SALIWANCHIK, LLOYD & EISENSCHENK

(57) ABSTRACT

The present inventors have found that HMGB1 fragment peptides having a particular amino acid sequence exhibit the effects of improvement of cardiac function, inhibition of cardiomyocyte hypertrophy, inhibition of myocardial fibrosis, and promotion of angiogenesis in an animal model of dilated cardiomyopathy, that the particular HMGB1 fragment peptides also exhibit the effects of improvement of cardiac function, inhibition of cardiomegaly, inhibition of cardiomyocyte hypertrophy, inhibition of myocardial fibrosis, and promotion of angiogenesis in an animal model of ischemic cardiomyopathy caused by old myocardial infarction, and that the particular HMGB1 fragment peptides exhibit the effects of inhibition of cardiomyocyte hypertrophy and inhibition of myocardial fibrosis in an animal model of hypertensive cardiomyopathy. Based on these findings, pharmaceutical compositions are provided for the prevention and/or treatment of cardiomyopathy and old myocardial infarction and chronic heart failure resulting therefrom, which comprise an HMGB1 fragment peptide having a particular amino acid sequence.

28 Claims, 23 Drawing Sheets

Specification includes a Sequence Listing.

(56) References Cited

U.S. PATENT DOCUMENTS

| | | | |
|---|---|---|---|
| 8,673,580 B2 | 3/2014 | Tamai et al. | |
| 9,623,078 B2 * | 4/2017 | Tamai | C07K 14/4718 |
| 9,688,733 B2 | 6/2017 | Tamai et al. | |
| 9,919,010 B2 | 3/2018 | Tamai et al. | |
| 10,550,165 B2 * | 2/2020 | Tamai | A61P 1/04 |
| 10,595,530 B2 | 3/2020 | Goodman et al. | |
| 10,626,153 B2 | 4/2020 | Bianchi et al. | |
| 2003/0003482 A1 | 1/2003 | Halle et al. | |
| 2003/0060410 A1 | 3/2003 | Tracey et al. | |
| 2004/0031072 A1 | 2/2004 | La Rosa et al. | |
| 2004/0156851 A1 | 8/2004 | Newman | |
| 2004/0191246 A1 | 9/2004 | Connelly et al. | |
| 2004/0242481 A1 | 12/2004 | Bianchi et al. | |
| 2004/0249448 A1 | 12/2004 | Gault | |
| 2004/0265971 A1 | 12/2004 | Sato et al. | |
| 2005/0014255 A1 | 1/2005 | Tang et al. | |
| 2005/0101564 A1 | 5/2005 | Pilarski | |
| 2006/0003312 A1 | 1/2006 | Blau et al. | |
| 2006/0035851 A1 | 2/2006 | Bianchi et al. | |
| 2006/0039896 A1 | 2/2006 | Kleinsek et al. | |
| 2006/0069064 A1 | 3/2006 | Khaldoyanidi | |
| 2006/0111287 A1 | 5/2006 | Bianchi | |
| 2006/0183667 A1 | 8/2006 | Jonassen et al. | |
| 2007/0154529 A1 | 7/2007 | Bullerdiek | |
| 2007/0238663 A1 | 10/2007 | Capogrossi et al. | |
| 2008/0038309 A1 | 2/2008 | Fumero et al. | |
| 2009/0053277 A1 | 2/2009 | Nagaya et al. | |
| 2009/0062187 A1 | 3/2009 | Bianchi et al. | |
| 2009/0202500 A1 | 8/2009 | Tamai et al. | |
| 2010/0040608 A1 | 2/2010 | Wahren-Herlenius et al. | |
| 2010/0280493 A1 | 11/2010 | Nayak | |
| 2011/0097309 A1 | 4/2011 | Tamai et al. | |
| 2012/0237504 A1 | 9/2012 | Brooks et al. | |
| 2012/0251510 A1 | 10/2012 | Tamai et al. | |
| 2014/0206619 A1 | 7/2014 | Tamai et al. | |
| 2015/0273017 A1 * | 10/2015 | Tamai | C07K 14/4718 514/16.4 |
| 2016/0154012 A1 * | 6/2016 | Fuhrmann | G01N 33/92 506/9 |
| 2018/0055886 A1 | 3/2018 | Tamai et al. | |
| 2018/0072785 A1 | 3/2018 | Tamai et al. | |
| 2020/0038486 A1 | 2/2020 | Tamai et al. | |
| 2020/0291359 A1 | 9/2020 | Tamai et al. | |
| 2022/0265787 A1 | 8/2022 | Tamai et al. | |

FOREIGN PATENT DOCUMENTS

| | | | |
|---|---|---|---|
| CA | 2325226 A1 | 5/2001 | |
| CA | 2512512 A1 | 7/2004 | |
| CA | 2636788 A1 | 5/2008 | |
| CN | 1193092 C | 3/2005 | |
| CN | 1671742 A | 9/2005 | |
| CN | 100447154 C | 12/2008 | |
| CN | 101366728 A | 2/2009 | |
| CN | 101374538 A | 2/2009 | |
| CN | 102076350 A | 5/2011 | |
| CN | 102247392 A | 11/2011 | |
| CN | 102443064 A | 5/2012 | |
| CN | 102711777 A | 10/2012 | |
| CN | 103687946 A | 3/2014 | |
| CN | 104884076 A | 9/2015 | |
| CN | 107188948 A | 9/2017 | |
| EP | 0791601 A2 | 8/1997 | |
| EP | 1114862 A2 | 7/2001 | |
| EP | 1459759 A1 | 9/2004 | |
| EP | 2039367 A1 | 3/2009 | |
| EP | 2055308 A1 | 5/2009 | |
| EP | 2284255 A1 | 2/2011 | |
| EP | 2301559 A1 | 3/2011 | |
| EP | 2301560 A1 | 3/2011 | |
| EP | 2601971 A1 | 6/2013 | |
| EP | 2913058 A1 | 9/2015 | |
| EP | 2913059 B1 | 4/2018 | |
| EP | 2494977 B1 | 6/2018 | |
| EP | 2703487 B1 | 6/2018 | |
| EP | 3556378 A1 | 10/2019 | |
| EP | 3358011 B1 | 3/2020 | |
| EP | 3719117 A1 | 10/2020 | |
| EP | 3750553 A1 | 12/2020 | |
| JP | 3018313 B2 | 3/2000 | |
| JP | 3421741 B2 | 11/2001 | |
| JP | 2003505506 A | 2/2003 | |
| JP | 2005508913 A | 4/2005 | |
| JP | 2005512507 A | 5/2005 | |
| JP | 2005537253 A | 12/2005 | |
| JP | 2006510619 A | 3/2006 | |
| JP | 2006517537 A | 7/2006 | |
| JP | 2006523085 A | 10/2006 | |
| JP | 4982739 B2 | 12/2007 | |
| JP | 2008507505 A | 3/2008 | |
| JP | 2008511300 A | 4/2008 | |
| JP | 2010503630 A | 2/2010 | |
| JP | 5134772 B2 | 1/2013 | |
| KR | 10-2005-0054907 A | 6/2005 | |
| KR | 20090078304 A | 7/2009 | |
| KR | 101448800 B1 | 10/2014 | |
| KR | 10-2015-0103660 A | 9/2015 | |
| KR | 10-1636139 B1 | 7/2016 | |
| RU | 2005102593 A | 10/2005 | |
| RU | 2410125 C2 | 4/2009 | |
| RU | 2599448 C2 | 10/2016 | |
| WO | 0108683 A1 | 2/2001 | |
| WO | 02074337 A1 | 9/2002 | |
| WO | 02088181 A2 | 11/2002 | |
| WO | 02092004 A2 | 11/2002 | |
| WO | 03026691 A2 | 4/2003 | |
| WO | 03043651 A1 | 5/2003 | |
| WO | 2004004763 A2 | 1/2004 | |
| WO | 2004004770 A1 | 1/2004 | |
| WO | 2004044001 A2 | 5/2004 | |
| WO | 2004046345 A2 | 6/2004 | |
| WO | 2004061456 A2 | 7/2004 | |
| WO | 2005025604 A2 | 3/2005 | |
| WO | 2005074984 A1 | 8/2005 | |
| WO | 2005087797 A1 | 9/2005 | |
| WO | 2006008779 A1 | 1/2006 | |
| WO | 2006010628 A1 | 2/2006 | |
| WO | 2006024547 A2 | 3/2006 | |
| WO | 2006047820 A1 | 5/2006 | |
| WO | 2006077614 A1 | 7/2006 | |
| WO | 2006080434 A1 | 8/2006 | |
| WO | 2006100651 A1 | 9/2006 | |
| WO | 2006114805 A2 | 11/2006 | |
| WO | 2007015546 A1 | 2/2007 | |
| WO | 2007031100 A1 | 3/2007 | |
| WO | 2007061762 A2 | 5/2007 | |
| WO | 2007076200 A2 | 7/2007 | |
| WO | 2007130725 A2 | 11/2007 | |
| WO | 2008018641 A1 | 2/2008 | |
| WO | 2008031612 A1 | 3/2008 | |
| WO | 2008053892 A1 | 5/2008 | |
| WO | 2008155659 A2 | 12/2008 | |
| WO | 2009133939 A1 | 11/2009 | |
| WO | 2009133940 A1 | 11/2009 | |
| WO | 2009133943 A1 | 11/2009 | |
| WO | 2011046570 A1 | 4/2011 | |
| WO | 2011052668 A1 | 5/2011 | |
| WO | 2012147470 A1 | 11/2012 | |
| WO | 2014065347 A1 | 5/2014 | |
| WO | 2014065348 A1 | 5/2014 | |
| WO | WO-2014191364 A1 * | 12/2014 | A61K 31/713 |
| WO | 2016184795 A1 | 11/2016 | |
| WO | 2018186480 A1 | 10/2018 | |
| WO | 2019107530 A1 | 6/2019 | |
| WO | 2019107566 A1 | 6/2019 | |
| WO | 2019156137 A1 | 8/2019 | |
| WO | 2020071519 A1 | 4/2020 | |
| WO | 2020071520 A1 | 4/2020 | |

(56) References Cited

FOREIGN PATENT DOCUMENTS

| WO | 2020158924 A1 | 8/2020 |
|---|---|---|
| WO | 2021201260 A1 | 10/2021 |

OTHER PUBLICATIONS

Andersson et al. "HMGB1 as a DNA-binding cytokine"; Journal of Leukocyte Biology vol. 72, Dec. 2002; pp. 1084-1091. (Year: 2002).*
Scoote et al., "Pathophysiology of Heart Failure," Chpt. 19, Essential Cardiology: Principles and Practice, 2nd Ed., Humana Press Inc., Totowa, NJ, pp. 347-369 (Year: 2006).*
Asch et al., "Lack of sensitivity of the electrocardiogram for detection of old myocardial infarction: A cardiac magnetic resonance imaging study," American Heart Journal, vol. 152(4), pp. 742-748 (Year: 2006).*
Maron et al., "Contemporary Definitions and Classification of the Cardiomyopathies," Circulation, 113(14), pp. 1807-1816 (Year: 2006).*
Ball et al., "Mesenchymal stem cells and neovascularization: role of platelet-derived growth factor receptors," J Cell Mol Bio, 11 pp. 1012-1030 (Year: 2007).*
Limana, et al. "HMGB1 attenuates cardiac remodeling in the failing heart via enhanced cardiac regeneration and miR-206-mediated inhibition of TIMP-3," PloS one 6.6: e19845, pp. 1-11 (Year: 2011).*
Blain et al., "δ-Sarcoglycan-Deficient Muscular Dystrophy: From Discovery to Therapeutic Approaches," Skeletal Muscle, vol. 1, Article: 13, pp. 1-12 (Year: 2011).*
Definition of cardiomyopathy, Harvard Health Publishing, pp. 1-3 (Year: 2014).*
Gallina et al., "A New Paradigm in Cardiac Regeneration: The Mesenchymal Stem Cell Secretome," Stem Cells Intl., Article ID 765846, pp. 1-10 (Year: 2015).*
Kido et al., "The Administration of High-morbidity Group Box 1 Fragment Prevents Deterioration of Cardiac Performance by Enhancement of Bone-Marrow Mesenchymal Stem Cells Homing in the Delta-Sarcoglycan-Deficient Hamster," vol. 136, Issue suppl_1: Abstracts from the AHA's 2017 Sessions (1 page) (Year: 2017).*
Weintraub et al., "Dilated cardiomyopathy," Lancet, 390, pp. 400-414 (Year: 2017).*
NCBI MedGen definition for "old myocardial infarction" https://www.ncbi.nlm.nih.gov/medgen/57612 (1 page) (Year: 2021).*
Selected cardiac diagnoses and ICD-10 codes (1 page) (Year: 2021).*
He et al. Exogenous High-Mobility Group Box 1 Protein Prevents Post-infarction Adverse Myocardial Remodeling Through TGF-b/Smad Signaling Pathway. Journal of Cellular Biochemistry 114:1634-1641; (2013). (Year: 2013).*
Kaneko et al. Bone Marrow Mononuclear Cell Transplantation Improves Cardiac Function in Ischemic Cardiomyopathy via High Mobility Group Box 1 Released from Dead Donor Cells. ABSTRACT 11250. Circulation. Issue: vol. 126(21) Supplement, 20 (Nov. 2012). (Year: 2012).*
Narumi et al. Cardiac-Specific Overexpression of High-Mobility Group Box 1 Protects Cardiomyocyte from Apoptosis During the Pathogenesis of Doxorubicin Cardiomyopathy. ABSTRACT 15265. Circulation. Issue: vol. 126(21) Supplement, 20 (Nov. 2012). (Year: 2012).*
Narumi et al. High-mobility group box 1-mediated heat shock protein beta 1 expression attenuates mitochondrial dysfunction and apoptosis. Journal of Molecular and Cellular Cardiology vol. 82:1-12 (2015). (Year: 2015).*
Funayama et al. Cardiac nuclear high mobility group box 1 prevents the development of cardiac hypertrophy and heart failure. Cardiovascular Research vol. 99, 657-664, (2013). (Year: 2013).*
Takahashi et al. Modulated Inflammation by Injection of High-Mobility Group Box 1 Recovers Post-Infarction Chronically Failing Heart. Circulation. vol. 118 [suppl 1]:S106-S114, (2008). (Year: 2008).*
Lotze et al. High-Mobility Group Box 1 Protein (HMGB1): Nuclear Weapon in the Immune Arsenal. Nature Reviews. Immunology vol. 5:331-342, (Apr. 2005). (Year: 2005).*
Fenton et al. Rheostat positions: A new classification of protein positions relevant to pharmacogenomics Medicinal Chemistry Research 29:1133-1146; (2020). (Year: 2020).*
Bhattacharya et al. Impact of genetic variation on three dimensional structure and function of proteins Plos One 12(3): e0171355; (2017). (Year: 2017).*
Tokuriki et al. Stability effects of mutations and protein evolvability. Curr. Opin. Struc. Biol. 19:596-604; (2009). (Year: 2009).*
Guo et al. Protein tolerance to random amino acid change. PNAS USA 101(25):9205-10; (2004). (Year: 2004).*
Bigazzi. Introduction to Review Series on Animal Models of Human Disease. Clinical Immunology and Immunopathology, vol. 74/No. 1, p. 1, (Jan. 1995). (Year: 1995).*
Bretag. Too much hype, not enough hope: Are balanced reporting and proper controls too much to expect from therapeutic studies in animal models of neuromuscular diseases that presage clinical trials in humans? Neuromuscular Disorders 17:203-205 (2007). (Year: 2007).*
Sisikian et al. Dilated Cardiomyopathy: Evolution of Pathogenesis Concepts and Potential For New Therapies. The New Armenian Medical Journal. vol. 9/No. 1, p. 4-18, (2015). (Year: 2015).*
Justice et al. Using the mouse to model human disease: increasing validity and reproducibility, Disease, Models & Mechanisms 9: 101-103, (2016). (Year: 2016).*
Del Buono et al. Ischemic Cardiomyopathy and Heart Failure After Acute Myocardial Infarction. Current Cardiology Reports 24:1505-1515, (2022). (Year: 2022).*
Hruby, V.J., "Designing Peptide Receptor Agonists and Antagonists." Nature Reviews Drug Discovery, 2002: 847-858.
Huttunen, H.J. et al., "Receptor for Advanced Glycation End Products-binding COOH-terminal Motif of Amphoterin Inhibits Invasive Migration and Metastasis," Cancer Research, 2002, 62: 4805-4811.
Instruction Manual of HiTrap chelating HP (Amersham Biosciences), 2003, pp. 1-6.
Ishikane, Shin, et al., "Development of multi-growth factor secreted fetal membrane-derived mesenchymal stem cell sheets." Grants-in-Aid for Scientific Research, 2014, pp. 1-6.
Shikane, S., "Therapeutic application of allogenic fetal membrane-derived mesenchymal stem cells transplantation in regenerative medicine," Pharmaceutical Bulletin of Fukuoka University, Mar. 2011, 11(0): 17-25.
"Isolating culture and induced differentiation of marrow mesenchyma stem cells," Principles and Protocols of Tissue Engineering, Jun. 2004, 277-8 (English translation attached).
Jansen, J. et al., "Transplantation of hematopoietic stem cells from the peripheral blood," Journal of Cellular and Molecular Medicine, 2005, 9(1): 37-50.
Jayaraman, L. et al., "High mobility group protein-1 (HMG-1) is a unique activator of p53," Genes & Development, 1998, 12(4): 462-472.
Jiang, Y. et al., "Pluripotency of mesenchymal stem cells derived from adult marrow," Nature, 2002, 418(6893): 41-49. Epub Jun. 20, 2012.
Jiao, C. et al., "Researchers find nerve damage may precede diabetic retinopathy," EurekAlert! Science News, Aor. 2016, https://www.eurekalert.org/pub_releases/2016-04/uoih-rfv042616.php.
Kaneda, et al., "Tissue repair mechanism by bone-marrow-derived stem cells." Experimental Mediciner, 2013, 31(5): 655-661.
Kassis, I. et al., "Isolation of mesenchymal stem cells from G-CSF mobilized human peripheral blood using fibrin microbeads," Bone Marrow Transplant, 2006, 37(10): 967-976.
Kawabata, H. et al., "High Mobility Group Box 1 is Upregulated After Spinal Cord Injury and Is Associated With Neuronal Cell Apoptosis," Spine, 2010, 35(11): 1109-1115.
Kern, S. et al., "Comparative Analysis of Mesenchymal Stem Cells from Bone Marrow, Umbilical Cord Blood, or Adipose Tissue," Stem Cells, 2006, 24(5): 1294-1301. Epub Jan. 12, 2006.
Kessler, M.W. et al., "Tissue Engineering and Cartilage," Organogenesis, Jan. 2008, 4(1): 28-32.

(56) References Cited

OTHER PUBLICATIONS

Kikuchi, K. et al., "HMGB1 as a therapeutic target in spinal cord injury: A hypothesis for novel therapy development (Review)," Experimental and Therapeutic Medicine, 2011, 2: 767-770.

Kikuchi, et al., "Systemic administration of HMGB1 improves bleomycin-induced skin fibrosis by locally accumulating bone marrow mesenchymal stem cells." Regenerative Medicine, Feb. 1, 2017, 16: 422.

Kim, S. et al., "Skin Regeneration Using Keratinocytes and Dermal Fibroblasts Cultured on Biodegradable Microspherical Polymer Scaffolds," Journal of Biomedical Materials Research Part B: Applied Biomaterials, 2005, 75(2): 369-377.

Kirov, S.A. et al., "In Vivo 2-Photon Microscopy Reveals G-CSF Enhanced Mobilization and Targeting of Neo- Endogenous Bone Marrow Stromal Cells to Stroke Injury Sites," Stroke, Apr. 2009, 40(4): 1-2, e133, Abstract No. 107.

Kitahara, T. et al., "High-Mobility Group Box 1 Restores Cardiac Function After Myocardial Infarcation in Transgenic Mice," Cardiovascular Research, European Society of Cardiology, Oct. 1, 2008, 80: 40-46.

Koc, O. et al., "Mesenchymal Stem Cells: Heading into the Clinic," Bone Marrow Transplantation, 2001, 27(3): 235-239.

Kohno, T. et al., "High Mobility Group Box 1 Protein is Associated With Post-Infarction Healing Process and Left Ventricular Remodeling," Circ. J., 2008, 72 Supplement 1, P J-004: 510-511.

Kokkola, R., et al., "RAGE is the Major Receptor for the Proinflammatory Activity of HMGB1 in Rodent Macrophages." Scandinavian Journal of Immunology, 2005, 61: 1-9.

Komurasaki, et al., "HMGB1 ameliorates bleomycin-induced skin fibrosis by promoting accumulation of mesenchymal stem cells to the lesion." The 48th Annual Meeting of The Japanese Society of Matrix Biology and Medicine, 2016, p. 78.

Komurasaki, Y., et al., "555 Systemic HMGB1 Administration Ameliorated Bleomycin-Induced Skin Fibrosis by Promoting Accumulation of Bone Marrow-Derived Mesenchymal Stem Cells to the Lesion." Journal of Investigative Dermatology, 2016, 136(9): S255.

Laflamme, M. et al., "Regenerating the heart," Nature Biotechnology, 2005, 23(7): 845-856.

La Rosa, T.J. et al., "Glycine max protein Seq ID No. 211221," Geneseq Accession No. AFQ20044, 2007.

Lanza, R et al., "Essentials of Stem Cell Biology—Chapter 27, Mesenchymal Stem Cells," Elsevier Academic Press, 2006, pp. 205-210.

Li, L., et al., "Emerging Role of HMGB 1 in Fibrotic Diseases." Journal of Cellular and Molecular Medicine, 2014, 18(12): 2331-2339.

Li, S. et al., "Millennium Review, Nonviral gene therapy: promises and challenges," Gene Ther., 2000, 7: 31-34, Macmillan Publishers Ltd.

Li, Y. et al., "Advancement of Human Multiply, Sex health and Reproductive Medical Science," Peking University Medical Press, Mar. 2007, 1st Edition, pp. 270-271.

Li, Z. et al., "Heat-Shock Proteins," Current Protocols in Immunology, 2003, Supplement 58, A.IT.1-A.IT.6.

Limana, F. et al., "Exogenous High-Mobility Group Box 1 Protein Induces Myocardial Regeneration After Infarction via Enhanced Cardiac C-Kit+ Cell Proliferation and Differentiation," Circulation Research, 2005, 97(8): e73-83. Epub Sep. 15, 2005.

Lin, S. et al., "The isolation of novel mesenchymal stromal cell chemotactic factors from the conditioned medium of tumor cells," Experimental Cell Research, 2008, 314(17): 3107-3117. Epub Aug. 8, 2008.

Liotta, F. et al., "Toll-Like Receptors 3 and 4 Are Expressed by Human Bone Marrow-Derived Mesenchymal Stem Cells and Can Inhibit Their T-Cell Modulatory Activity by Impairing Notch Signaling," Stem Cells, 2008, 26(1): 279-289. Epub Oct. 25, 2007.

Liu, K.et al., "Human Placental Extract Stimulates Liver Regeneration in Rats," Biological and Pharmaceutical Bulletin, 1998, 21(1): 44-49.

Lonza BenchGuides_Poietics hMSC Human Mesenchymal Stem Cells and Media( Document # TS-PT-212-7 04/08).

Lund, L., et al., "The Registry of the International Society for Heart and Lung Transplantation: Thirty-Third Adult Heart Transplantation Report-2016; Focus Theme: Primary Diagnostic Indications for Transplant." The Journal of Heart and Lung Transplantation, 2016, 35(10): 1158-1169.

Mansbridge, J. et al., "Skin Tissue Engineering," J. Biomater, Sci. Polymer, Ed., Aug. 1, 2008, 19(8): 955-968.

Martin-Murphy, B.V. et al., "The Role of Damage Associated Molecular Pattern Molecules in Acetaminophen- Induced Liver Injury in Mice," Toxicol Lett, Feb. 2010, 192(3): 1-20.

Maruyama, I., "Inflammation and HMGB1/RAGE system," Kekkan Igaku, 2005, 6(5): 519-525 (English translation attached).

Matsumoto, K., et al., "Up-Regulation of Hepatocyte Growth Factor Gene Expression by Inerleukin-1 in Human Skin Fibrosis," Biochemical and Biophysical Research Communications, 1992, 188(1): 235-243.

Meng, E. et al., "High Mobility Group Box 1 Protein Inhibits the Proliferation of Human Mesenchymal Stem Cells and Promotes Their Migration and Differentiation along Osteoblastic Pathway," Stem Cells and Development, 2008, 17(4): 805-814.

Meng, E. et al., "HMGB1 induces migration of human bone marrow-derived mesenchymal stem cells," Bulletin of the Academy of Militaryt Medical Sciences, 2006, 30(3): 213-216 (English translation attached).

Merenmies, J. et al., "30-kDa Heparin-binding Protein of Brain (Amphoterin) Involved in Neurite Outgrowth," Journal of Biological Chemistry 1991, 266(25): 16722-16729.

Mistry, A.R. et al., "Recombinant HMG1 Protein Produced in Pichia pastoris: A Nonviral Gene Delivery Agent," Biotechniques, 1997, 22(4): 718-729.

Mori, T. et al., "Stem Cells/ES cells—Mesenchymal Stem Cells—Human Bone Marrow Derived Mesenchymal Stem Cells," Saisei Iryou—Regenerative Medicine, 2005, 4(3): 421-429, 351.

Morosetti, R. et al., "MyoD expression restores defective myogenic differentiation of human mesoangioblasts from inclusion-body myositis muscle," PNAS, Nov. 7, 2006, 103(45): 16995-17000.

Mouse care guidance from the Institutional Animal Care and Use Committee at University of California, San Francisco; iacuc.ucsf.edu/Policies/BloodCollectionMice.doc; accessed May 15, 2014.

Muhamed, J., et al., "Phenotypic modulation of cell types around implanted polythylene terephthalate fabric in rabbit muscle." Toxicologic Pathology, 2013, 41: 497-507.

Muhammad, S. et al., "The HMGB1 Receptor RAGE Mediates Ischemic Brain Damage." The Journal of Neuroscience, Nov. 12, 2008, 28 (46): 12023-12031.

Müller, S. et al., "The double life of HMGB1 chromatin protein: architectural factor and extracellular signal," EMBO Journal, 2001, 20(16): 4337-4340.

Nakajima et al., "Dynamics and Role of High Mobility Group Box-1 (HMGB-1) in Injured Spinal Cord," Nihon Seikei Geka Gakkai Zasshi (J. Jpn. Orthop. Assoc.), 2010, 84(8): S1050.

Nakamura, K. et al., "p38 Mitogen-Activated Protein Kinase Functionally Contributes to Chondrogenesis Induced by Growth/Differentiation Factor-5 in ATDC5 Cells," Experimental Cell Research, 1999, 250(2): 351-363.

Narumi, T., et al., "High-mobility Group Box 1 Attenuates Mitochondrial Dysfunction and Apoptosis via Heat Shock Protein Beta 1 Induction in Doxorubicin-induced Cardiomyopathy." Bulletin of Yamagata University (Medical Science ), 2015, 33(2): 126-127. http://www.lib.yamagata-u.ac.jp/alllib/elib/kiyou/kiyoum/kiyoum-33-2/image/kiyoum-33-2-125to131.pdf.

Opitz, C.E. et al., "Toll-Like Receptor Engagement Enhances the Immunosuppressive Properties of Human Bone Marrow-Derived Mesenchymal Stem Cells by Inducing Indoleamine-2, 3-dioxygenase-1 via Interferon-β and Protein Kinase R," Stem Cells, 2009, 27(4): 909-919.

Otsuru, S. et al., "BMP-2 mobilizes robust bone marrow mesenchymal progenitor cells to the circulating blood in bone regeneration," The 28th Meeting of the Molecular Biology Society of Japan, 2005, 733(3P-1012) (translated English abstract attached).

(56) References Cited

OTHER PUBLICATIONS

Ozaki, Y. et al., "Comprehensive Analysis of Chemotactic Factors for Bone Marrow Mesenchymal Stem Cells," Stem Cells and Development, 2007, 16(1): 119-129.
Palumbo, R. et al., "Cells migrating to sites of tissue damage in response to the danger signal HMGB1 require NF-kB activation," Journal of Cell Biology, 2007, 179(1): 33-40.
Palumbo, R. et al., "Extracellular HMGB1, a signal of tissue damage, induces mesoangioblast migration and proliferation," The Journal of Cell Biology, 2004, 164(3): 441-449.
Palumbo, R. et al., "High mobility group box 1 protein, a cue for stem cell recruitment," Biochemical Pharmacology, 2004, 68(6): 1165-1170.
Pandya, N.M., et al., "Angiogenesis—A New Target for Future Therapy." Vascular Pharmacology, 2006, 44: 265-274.
Panepucci, R.A. et al., "Abstract # 4427: Comparison of Gene Expression of Mesenchymal Stem Cells from the Umbilical Cord and from the Bone Marrow," Blood, Nov. 2003, 16(102): Abstract.
Panepucci, R. A. et al., "Comparison of Gene Expression of Umbilical Cord Vein and Bone Marrow-Derived Mesenchymal Stem Cells." Stem Cells, Dec. 2004, 22 (7): 1263-1278.
Pankov, R. et al., Fibronectin at a glance, J. Cell Sci., Oct. 2002, 115(20): 3861-3863.
Park, J., et al., "Involvement of Toll-Like Receptors 2 and 4 in Cellular Activation by High Mobility Group Box 1 Protein." Journal of Biological Chemistry, 2004, 279(9): 7370-7377.
Paul, S.R. et al., "Stromal Cell-Associated Hematopoiesis: Immortalization and Characterization of a Primate Bone Marrow-Derived Stromal Cell Line," Blood, 1991, 77(8): 1723-1733.
Pevsner-Fischer, M. et al., "Toll-like receptors and their ligands control mesenchymal stem cell functions," Blood, 2007, 109(4): 1422-1432. Epub Oct. 12, 2006.
Pittenger, M. et al., "Multilineage Potential of Adult Human Mesenchymal Stem Cells," Science, 1999, 284(5411): 143-147.
Popovic, K. et al., "Increased Expression of the Novel Proinflammatory Cytokine High Mobility Group Box Chromosomal Protein 1 in Skin Lesions of Patients With Lupus Erythematosus," Arthritis & Rheumatism, 2005, 52(11): 3639-3645.
Pusterla, T. et al., "High mobility group B2 is secreted by myeloid cells and has mitogenic and chemoattractant activities similar to high mobility group B1," Autoimmunity, 2009, 42(4): 308-310.
Quertainmont, R. et al., "Mesenchymal Stem Cell Graft Improves Recovery after Spinal Cord Injury in Adult Rats through Neurotrophic and Pro-Angiogenic Actions," Plos One, Jun. 2012, 7(6): 1-15.
Racanelli, V., et al., "The Liver as an Immunological Organ." Hepatology, 2006, 43(2): Suppl. 1—S54-S62.
Rahimi-Movaghar, V. et al., "Effect of Decompression on Complete Spinal Cord Injury in Rats," International Journal of Neuroscience, 2008, 118: 1359-1373.
Raicevic, G. et al., "Inflammation modifies the pattern and the function of Toll-like receptors expressed by human mesenchymal stromal cells," Human Immunology, 2010, 71(3): 235-244. Epub Jan. 6, 2010.
Raucci, A., et al., "The Janus Face of HMGB1 in Heart Disease: A Necessary Update." Cellular and Molecular Life Sciences, 2019, 76: 211-229.
Robinson, M.J. et al., "The S100 Family Heterodimer, MRP-8/14, Binds with High Affinity to Heparin and Heparan Sulfate Glycosaminoglycans on Endothelial Cells," Journal of Biological Chemistry, 2002, 277(5): 3658-3665. Epub Nov. 26, 2001.
Ross, M.H., et al., "Histology: a Text and Atlas: With Correlated Cell and Molecular Biology." Lippincott Williams & Wilkins, 2018.
Ryckman, S. et al., "Proinflammatory Activities of S100: Proteins S100A8, S100A9, and S100A8/A9 Induce Neutrophil Chemotaxis and Adhesion." J. Immunol., 2003, 170(6): 3233-3242.
Santamaria-Kisiel, L. et al., "Calcium-dependent and-independent interactions of the S100 protein family." Biochem. J., 2006, 396: 201-214.
Sasaki, M. et al., "Mesenchymal Stem Cells Are Recruited into Wounded Skin and Contribute to Wound Repair by Transdifferentiation into Multiple Skin Cell Type." The Journal of Immunology, Feb. 15, 2008, 180(4): 2581-2587.
Saver, J.L., "Time Is Brain-Quantified." Stroke, 2006, 37: 263-266.
Schaffer, M. R. et al., "Wound Fluid Inhibits Wound Fibroblast Nitric Oxide Synthesis." Journal of Surgical Research, 2004, 122(1): 43-48.
Schon, M. P., Boehncke, W. H., "Medical Progress: Psoriasis." The New England Journal of Medicine, May 2005, 352 (18): 1899-1912.
Seong, YS., Matzinger, P., "Hydrophobicity: an ancient damage-associated molecular pattern that initiates innate immune responses." Nature Reviews: Immunology, Jun. 2004, 4(6): 469-478.
Shibata, F. et al., "Fibroblast growth-stimulating activity of S100A9 (MRP-14)." Eur. J. Biochem., Feb. 2004, 271 (11): 2137-2143.
Shing, Y et al., "Heparin Affinity: Purification of a Tumor-Derived Capillary Endothelial Cell Growth Factor." Science, Mar. 23, 1984, 223: 1296-1299.
Slater, M. et al., "Endometriotic cells exhibit metaplastic change and oxidative DNA damage as well as decreased function, compared to normal endometrium." Journal of Molecular Histology, 2005, 36(4): 257-263.
Somia, N., Verma, I. M., "Reviews, Gene Therapy: Trials and Tribulations." Nature Reviews: Genetics, Nov. 2000, 1(2): 91-99, Macmillan Publishers Ltd.
Boo, E. T. L. et al., "Heat Shock Proteins as Novel Therapeutic Targets in Cancer." in vivo, 2008, 22(3): 311-316.
Straino, S. et al., "High-Mobility Group Box 1 Protein in Human and Murine Skin: Involvement in Wound Healing." Journal of Investigative Dermatology, Jan. 2008, 128: 1545-1553.
Sun, S. et al., "Isolation of Mouse Marrow Mesenchymal Progenitors by a Novel and Reliable Method." Stem Cells, 2003, 21(5): 527-535.
Tagami, K. et al., "Elevation of serum high-mobility group box 1 protein during granulocyte colony-stimulating factorinduced peripheral blood stem cell mobilisation." British Journal of Haematology, 2006, 135(4): 567-569.
Tagliafico, E. et al., "TGFB/BMP activate the smooth muscle/bone differentiation programs in mesoangioblasts." Journal of Cell Science, Apr. 2004, 117 (19): 4377-4388.
Takahashi, K. et al., "Effects of HMGB1 on PostInfarction Chronic Heart Failure—Novel Mechanism Regarding Therapeutic Effects of Cell Therapy." Supplement, 2011, 27 I-E-19:S189.
Takami, Y. et al., "Synergistic induction of hepatocyte growth factor in human skin fibroblasts by the inflammatory cytokines interleukin-1 and interferon-y." Biochemical and Biophysical Research Communications, 2005, 327: 212-217.
Takeishi, Yasuchika et al., "Importance of Inflammation and Immune Response in Heart Failure—Toll-Like Receptor-Mediated Signaling Pathway and Ventricular Remodeling After Myocardial Infarction." Journal of Clinical and Experimental Medicine, Jan. 30, 2010, 232(5):378-385.
Tamai, K. et al., "Development and Outlook of Internal Regeneration-Inducing Pharmaceuticals that use in vivo Bone Marrow Mesenchymal Stem / Progenitor Cell-Mobilizing Factors," Gene & Medicine MOOK, Jul. 22, 2012, pp. 207-212.
Tamai, K., "Development of regeneration-inducing medicine utilizing the in vivo injured tissue regeneration mechanism of peripheral circulating mesenchymal cells." BIO Clinica, Sep. 10, 2016, 31(10): 1042-1046.
Tamai et al., "Nihon Hiuka Gakkai Zasshi," Japanese Journal of Dermatology, 2008, 118(4): 645 (#EL28-4) (translated English abstract attached, titled "New Wave of Wound Healing").
Alden, T. D. et al., "In Vivo Endochondral Bone Formation Using a Bone Morphogenetic Protein 2 Adenoviral Vector." Human Gene Therapy, Sep. 1999, 10(13): 2245-2253.
Arminan, A. et al., "Mesenchymal Stem Cells Provide Better Results Than Hematopoietic Precursors for the Treatment of Myocardial Infarction." Journal of the American College of Cardiology, 2010, 55 (20): 2244-2253.
Basso, D. M. et al., "Basso Mouse Scale for Locomotion Detects Differences in Recovery after Spinal Cord Injury in Five Common Mouse Strains." Journal of Neurotrauma, 2006, 23 (5): 635-659.

(56) References Cited

OTHER PUBLICATIONS

Berry, M. F. et al., "Mesenchymal stem cell injection after myocardial infarction improves myocardial compliance." Am. J. Physiol. Heart Circ. Physiol., Jun. 2006, 290(6): H2196-H2203.

Bianchi, M. E. et al., "The DNA binding site of HMG1 protein is composed of two similar segments (HMG boxes), both of which have counterparts in other eukaryotic regulatory proteins." The EMBO Journal, Mar. 1992, 11 (3): 1055-1063.

Bianchi, M. E. et al., "High mobility group 1 protein (HMGB1) N-terminal peptide." Geneseq Accession No. ADO80180, Aug. 12, 2004.

Bittira, B. et al., "Mobilization and homing of bone marrow stromal cells in myocardial infarction." European Journal of Cardio-thoracic Surgery, 2003, 24(3): 393-398.

Brunner, S., et al., "Erythropoientin Administration After Myocardial Infarction in Mice Attenuates Ischemic Cardiomyopathy Associated with Enhanced Homing of Bone Marrow-Derived Progenitor Cells Via the CXCR-4/SDF-1 Axis." The FASEB Journal, 2009, 23: 351-361.

Bustin, M., "Regulation of DNA-Dependent Activities by the Functional Motifs of the High-Mobility-Group Chromosomal Proteins." Mol. Cell. Biol., 1999, 19 (8): 5237-5246.

Castro, R. F. et al., "Failure of Bone Marrow Cells to Transdifferentiate into Neural Cells in Vivo." Science, Aug. 2002, 297(5585): 1299.

Chamberlain, G. et al., "Concise Review: Mesenchymal Stem Cells: Their Phenotype, Differentiation Capacity, Immunological Features, and Potential for Homing." Stem Cells, 2007, 25: 2739-2749.

Charoonpatrapong, K. et al., "HMGB1 Expression and Release by Bone Cells." Journal of Cellular Physiology, 2006, 207(2): 480-490.

Chen, T., et al., "Involvement of high mobility group box-1 in imiquimod-induced psoriasis-like mice model." Journal of Dermatology, 2017, 44: 573-581.

Chen, X. et al., "Human Bone Marrow Stromal Cell Cultures Conditioned by Traumatic Brain Tissue Extracts: Growth Factor Production." Journal of Neuroscience Research, 2002, 69: 687-691.

Chen, Y. et al., "Coaxing bone marrow stromal mesenchymal stem cells towards neuronal differentiation: progress and uncertainties." Cellular and Molecular Life Sciences, 2006, 63(14): 1649-1657.

Chopp, M., Li, Y., "Treatment of neural injury with marrow stromal cells." The Lancet Neurology, Jun. 2002, 1(2): 92-100.

Chou, D. K. H. et al., "Identity of nuclear high-mobility-group protein, HMG-1, and sulfoglucuronyl carbohydratebinding protein, SBP-1, in brain." Journal of Neurochemistry, 2001, 77(1): 120-131.

Cole, J. S., "Pharmacologic Mobilization of Mesenchymal Stem Cells for Enhanced Bone Formation." Colby College, Rush University, 2009, UMI No. 1466383, 1-82.

Degryse, B. et al., "The High Mobility Group (HMG) Boxes of the Nuclear Protein HMG1 Induce Chemotaxis and Cytoskeleton Reorganization in Rat Smooth Muscle Cells." The Journal of Cell Biology, Mar. 2001, 152 (6): 1197-1206.

Delarosa, O., Lombardo, E., "Modulcation of Adult Mesenchymal Stem Cells Activity by Toll-Like Receptors: Implications on Therapeutic Potential." Mediators of Inflammation, 2010 vol. 2010, Article ID: 865601, pp. 1-9.

Desai, N. P., Hubbell, J. A., "Tissue response to intraperitoneal implants of polyethylene oxide-modified polyethylene terephthalate." Biomaterials, 1992, 13 (8): 505-510.

De Souza, A. W. S. et al., "HMGB1 in vascular diseases: its role in vascular inflammation and atherosclerosis." Autoimmunity Reviews, 2012, 11: 909-917.

Dong, Y. et al., "HMGB1 Protein Does Not Mediate the Inflammatory Response in Spontaneous Spinal Cord Regeneration." The Journal of Biological Chemistry, Jun. 11, 2013, 288 (25): 18204-18218.

Eckert, R. L. et al., "S100 Proteins in the Epidermis." The Journal of Investigative Dermatology, 2004, 123(1): 23-33.

Ehrchen, J. M. et al., "The endogenous Toll-like receptor 4 agonist S100A8/S100A9 (calprotectin) as innate amplifier of infection, autoimmunity, and cancer." Journal of Leukocyte Biology, Sep. 2009, 86: 557-566.

Erlandsson, H. et al., "The nuclear protein HMGB1 as a proinflammatory mediator," European Journal of Immunology, 2004, 34(6): 1503-1512.

Esposito, E. et al., "Melatonin reduces stress-activated/mitogen-activated protein kinases in spinal cord injury." J. Pineal. Res., 2009, 46: 79-86.

Fang, P. et al., "HMGB1 Contributes to Regeneration After Spinal Cord Injury in Adult Zebrafish." Mol. Neurobio., 2014, 49: 472-483.

Forte, G. et al., "Hepatocyte Growth Factor Effects on Mesenchymal Stem Cells: Proliferation, Migration, and Differentiation." Stem Cells, 2006, 24: 23-33.

Fritsch, A., et al., "A Hypomorphic Mouse Model of Dystrophic Epidermolysis Bullosa Reveals Mechanisms of Disease and Response to Fibroblast Therapy." The Journal of Clinical Investigation, 2008, 118(5): 1669-1679.

Fujii, M. et al., "Roles of Bone Morphogenetic Protein Type I Receptors and Smad Proteins in Osteoblast and Chondroblast Differentiation." Molecular Biology of the Cell, Nov. 1999, 10(11): 3801-3813.

Fukushima, N., et al., "Registry Report on Heart Transplantation in Japan (Jun. 2016)." Circulation Journal, 2016: CJ-16.

Germani, A. et al., "Pivotal Advance: High-mobility group box 1 protein—a cytokine with a role in cardiac repair," Journal of Leukocyte Biology, 2007, 81(1): 41-45. Epub Aug. 29, 2006.

Gong, W. et al., "The Anti-Inflammatory Activity of HMGB1 A Box is Enhanced When Fused with C-Terminal Acidic Tail," Journal of Biomedicine and Biotechnology, 2010, vol. 2010, Article ID 915234, 6, pp. 2-10. doi:10.115/2010915234.

Goto, et al., "Investigation of the application of myocardial regeneration inducing therapy using HMGB1 to cardiac infarction." Regenerative Medicine, Feb. 1, 2017, 16: 289.

Granero-Molto, F. et al., "Role of mesenchymal stem cells in regenerative medicine: application to bone and cartilage repair," Expert Opinion on Biological Therapy, 2008, 8(3): 255-268.

Gudjonsson, J. et al., "Psoriasis," Fitzpatrick's Dermatology in General Medicine, 8th edition, New York: Mc-Graw Hill Medical, 2012, pp. 197-217.

Gueukdjian S.A., "Intra-Arterial Injections in the Treatment of Peripheral Vascular Disease," Postgrad Medical Journal, Jan. 1955, 31(351): 30-31.

Guillot, L., et al., "Response of Human Pulmonary Epithelial Cells to Lipopolysaccharide Involves Toll-like Receptor 4 (TLR4)-dependent Signaling Pathways." Journal of Biological Chemistry, 2004, 279(4): 2712-2718.

Guo, J., et al., "Monocyte Chemotactic Protein-1 Promotes the Myocardial Homing of Mesenchymal Stem Cells in Dilated Cardiomyopathy." International Journal of Molecular Sciences, 2013, 14: 8164-8178.

Harris, H. et al., "Alarmin(g) news about danger," EMBO Reports, 2006, 7(8): 774-778. Epub Jul. 21, 2006.

He, Y.T., et al., "HMGB1 Ameliorates Inflammatory Bowel Disease by Inducing Circulating Mesenchymal Stem Cells." The 17th Congress of the Japanese Society for Regenerative Medicine, 2018, 34, Abstract.

Healthwise Staff, "Age-related Macular Degeneration," University of Michigan Health System, Aug. 2015, https:www.uofmhealth.org/health-library/hw176039.

Heil, M. et al., "An engineered heparin-binding form of VEGF-E (hbVEGF-E)," Angiogenesis, 2003, 6(3): 201-211.

Herrera, M.B. et al., "Exogenous mesenchymal stem cells localize to the kidney by means of CD44 following acute tubular injury," Kidney International, 2007, 72: 430-441.

Hiratsuka S. et al., "Tumour-mediated upregulation of chemoattractants and recruitment of myeloid cells predetermines lung metastasis," Natural Cell Biology, 2006, 8(12): 1369-1375. Epub Nov. 26, 2006.

(56) References Cited

OTHER PUBLICATIONS

HMGBiotech, "BoxA from HMGB1, human & mouse, LPS-free." HMGBiotech Srl, 2008, C.F. e P.IVA 04942740962, http://www.hmgbiotech.com/products.php?ID=91.

HMGBiotech, "BoxA from HMGB1, human & mouse, LPS-free-Datasheet." HMGBiotech Srl, 2008, Via Moretto da Brescia 25, 20133-Milano, Italy, http://www.hmgbiotech.com/upload/documenti/0515122144_boxa.

Hori, O. et al., "The Receptor for Advanced Glycation End Products (RAGE) Is a Cellular Binding Site for Amphoterin," Journal of Biological Chemistry, 1995, 270(43): 25752-25761.

Hornef, M., et al., "Toll-Like Receptor 4 Resides in the Golgi Apparatus and Colocalizes with Internalized Lipopolysaccharide in Intestinal Epithelial Cells." The Journal of Experimental Medicine, 2002, 195(5): 559-570.

Tamai, Katsuto et al., "PDGFRα-positive cells in bone marrow are mobilized by high mobility group box 1 (HMGB1) to regenerate injured epithelia," http://www.pnas.org/content/early/2011/03/30/1016753108.full.pdf+html, http://www.pnas.org/content/early/2011/03/30/1016753108/suppl/DCSupplemental, http://www.pnas.org/content/suppl/2011/03/31/1016753108.DCSupplemental/pnas.201016753Sl.pdf, http://www.pnas.org/content/early/2011/03/30/1016753108.abstract, http://www.pnas.org/content/early/2011/03/30/1016753108.full.pdf.

Tamai, Katsuto et al., "PDGFRα-positive cells in bone marrow are mobilized by high mobility group box 1 (HMGB1) to regenerate injured epithelia," http://www.pnas.org/content/108/16/6609.full.pdf+html, http://www.pnas.org/content/108/16/6609/suppl/DCSupplemental, http://www.pnas.org/content/suppl/2011/03/31/1016753108.DCSupplemental/pnas.201016753Sl.pdf, http://www.pnas.org/content/108/16/6609.abstract, http://www.pnas.org/content/108/16/6609.figures-only, http://www.pnas.org/content/108/16/6609.full.pdf, http://www.pnas.org/.

Tamai, K. et al., "PDGFRα-positive cells in bone marrow are mobilized by high mobility group box 1 (HMGB1) to regenerate inured epithelia," Proceedings of the National Academy of Sciences, 2011, 108(16): 6609-6614.

Tamai, K. et al., U.S. Appl. No. 11/997,475, "Mesenchymal Stem Cell Inducer, Tissue Regeneration Promoter and Method of Preparing Mesenchymal Stem Cell.", filed Jan. 31, 2008.

Tamai, K. et al., U.S. Appl. No. 16/713,202, "Peptide for Inducing Regeneration of Tissue and Use Thereof.", filed Dec. 13, 2019.

Tamai, K. et al., U.S. Appl. No. 16/768,654, "Therapeutic Agent for Inflammatory Bowel Disease.", filed May 30, 2020.

Tamai, K. et al., U.S. Appl. No. 16/967,919, "Therapeutic Agent for Psoriasis.", filed Aug. 6, 2020.

Tang, D. et al., "High-Mobility Group Box 1, Oxidative Stress, and Disease." Antioxidants & Redox Signaling, 2011, 14 (7): 1315-1335, doi: 10.1089/ars.2010.3356.

Tang, L., Eaton, J. W., "Fibrin(ogen) Mediates Acute Inflammatory Responses to Biomaterials." J. Exp. Med., Dec. 1993, 178: 2147-2156.

Tao, A., et al., "Cardiomyocyte-Fibroblast Interaction Contributes to Diabetic Cardiomyopathy in Mice: Role of HMGB1/TLR4/IL-33 Axis." Biochimica et Biophysica Acta, 2015, 1852: 2075-2085.

Tatsumi, R. et al., "HGF/SF Is Present in Normal Adult Skeletal Muscle and Is Capable of Activating Satellite Cells," Developmental Biology, 1998, 194: 114-128.

Technical Manual Version 2.2.0, "Enumeration, Expansion, and Differentiation of Human Mesenchymal Progenitor Cells Using MesenCult@." STEMCELL Technologies, Oct. 2007, 1-18.

Telusma, G. et al., "Dendritic cell activating peptides induce distinct cytokine profiles," International Immunology, 2006, 18(11): 1563-1573. Epub Sep. 11, 2006.

Teoh, N., et al., "Low-Dose TNF-Alpha Protects Against Hepatic Ischemia-Reperfusion Injury In Mice: Implications for Preconditioning." Hepatology, 2003, 37(1): 118-128.

Thorey, I.S. et al., "The Ca2+-binding Proteins S100A8 and S100A9 Are Encoded by Novel Injury-regulated Genes*," Journal of Biological Chemistry, 2001, 276(38): 35818-35825. Epub Jul. 19, 2001.

Tsung, A., et al., "Hepatic Ischemia/Reperfusion Injury Involves Functional TLR4 Signaling in Nonparenchymal Cells." The Journal of Immunology, 2005, 175(11): 7661-7668.

Türker, S. et al., "Nasal route and drug delivery systems," Pharmacy World and Science, 2004, 26: 137-142.

Uchida et al., "Nihon Seikei Geka Gakkai Zasshi," The Journal of Japanese Orthopaedic Surgical Society, 2005, 79 (8): S832, 1-P6-6. (English translation attached, titled "The chemotactic activity of PDGF-bb BMP-2, and FGF-2 towards committed and uncommitted mesenchymal stem cells").

Ueta, M., et al., "Intracellularly Expressed TLR2s and TLR4s Contribution to an Immunosilent Environment at the Ocular Mucosal Epithelium." The Journal of Immunology, 2004, 173(5): 3337-3347.

Ulloa, L. et al., "High-mobility group box 1 (HMGB1) protein: Friend and foe," Cytokine & Growth Factor Reviews, 2006, 17: 189-201.

Uronen-Hansson, H., et al., "Toll-like Receptor 2 (TLR2) and TLR4 are Present Inside Human Dendritic Cells, Associated with Microtubules and the Golgi Apparatus but are not Detectable on the Cell Surface: Integrity of Microtubules is Required for Interleukin-12 Production in Response to Internalized Bacteria." Immunology, 2004, 111: 173-178.

Vandal, K. et al., "Blockade of S100A8 and S100A9 Suppresses Neutrophil Migration in Response to Lipopolysaccharide." The Journal of Immunology, Sep. 1, 2003, 171(5): 2602-2609.

Venereau, E. et al., "Mutually exclusive redox forms of HMGB1 promote cell recruitment or proinflammatory cytokine release." The Journal of Experimental Medicine, 2012, 209 (9): 1519-1528.

Wang, F. C., et al., "Overexpression of HMGB1 A-box reduced lipopolysaccharide-induced intestinal inflammation via HMGB1/TLR4 signaling in vitro." World J Gastroenterol, Jul. 7, 2015, 21(25): 7764-7776.

Wang, H. et al., "HMG-1 as a Late Mediator of Endotoxin Lethality in Mice," Science, 1999, 285(5425): 248-251.

Wang, H. et al., "Kansaibou no riron to gijutu," Science Press, Mar. 2005, 5: 58-61 (English translation attached, titled "Theories and Technologies for Stem Cells").

Wang, H.L. et al., "High mobility group protein B1 and the research progress of its biological effect," Journal of Chinese Modern Surgery, 2006, 3(22): 1806-1809 (English translation attached).

Wang, L. et al., "Ischemic cerebral tissue and MCP-1 enhance rat bone marrow stromal cell migration in interface culture," Experimental Hematology, 2002, 30: 831-836.

Wang, Y., "Biology of hematopoietic stem cell and the research method therof," Science Press, Mar. 2007, 1st Edition, pp. 56-58.

Wang, W. et al., "Intravenous administration of bone marrow mesenchymal stromal cells is safe for the lung in a chronic myocardial infarction model," Regen Med, Mar. 2011, 6(2): 179-190.

Watanabe, T., et al., "The Role of HMGB-1 on the Development of Necrosis During Hepatic Ischemia and Hepatic Ischemia/Reperfusion Injury in Mice." Journal of Surgical Research, 2005, 124: 59-66.

Wexler, S. et al., "Adult Bone Marrow is a Rich Source of Human Mesenchymal 'Stem' Cells but Umbilical Cord and Mobilized Adult Blood are Not," British Journal of Haematology, 2003, 121(2): 368-374.

Wolf, G. et al., "From the Periphery of the Glomerular Capillary Wall Toward the Center of Disease," Diabetes, Jun. 2005, 54(6): 1626-1634.

Woodbury, D. et al., "Adult Rat and Human Bone Marrow Stromal Cells Differentiate into Neurons," Journal of Neuroscience Research, Aug. 15, 2000, 61(4): 364-370.

Wu, Y. et al., "Mesenchymal Stem Cells Enhance Wound Healing Through Differentiation and Angiogenesis," Stem Cells, 2007, 25(10): 2648-2659. Epub Jul. 5, 2007.

Yamada, T. et al., "Regulation of osteoclast development by Notch signaling directed to osteoclast precursors and through stromal cells," Blood, Mar. 2003, 101(6): 2227-2234.

Yamaoka, S., et al., "1043 Systemic delivery of HMGB1 peptide ameliorates imiquimod-induced psoriasis-like dermatitis." Journal of Investigative Dermatology, 2018, 138(5): S177.

(56) References Cited

OTHER PUBLICATIONS

Yang, D. et al., "High mobility group box-1 protein induces the migration and activation of human dendritic cells and acts as an alarmin," Journal of Leukocyte Biology, 2007, 81(1): 59-66. Epub Sep. 11, 2006.
Yang, H., et al., "Reversing established sepsis with antagonists of endogenous high-mobility group box 1." Proceedings of the National Academy of Sciences, 2004, 101(1): 296-301.
Yang, S., et al., "Does Pretreatment of Bone Marrow Mesenchymal Stem Cells with 5-Azacytidine or Double Intravenous Infusion Improve Their Therapeutic Potential for Dilated Cardiomyopathy?" Medical Science Monitor Basic Research, 2013, 19: 20-31.
Youn, J.H. et al., "High Mobility Group Box 1 Protein Binding to Lipopolysaccharide Facilitates Transfer of Lipopolysaccharide to CD14 and Enhances Lipoplysaccharide-Mediated TNF-α Production in Human Monocytes," Journal of Immunology, 2008, 180(7): 5067-5074.
Yuan, Y. et al., "Differentiation of Mesenchymal Stem Cells in Cardiomyogenic Cells Under the Induction of Myocardial Cell Lysate," Chinese Journal of Cardiology, 2005, 33(2): 170-173.
Yu, Q., et al., "Impact of Repeated Intravenous Bone Marrow Mesenchymal Stem Cells Infusion on Myocardial Collagen Network Remodeling in a Rat Model of Doxorubicin-Induced Dilated Cardiomyopathy." Molecular and Cellular Biochemistry, 2014: 279-285.
Zheng, X., et al., "Adeno-associated virus-mediated colonic secretory expression of HMGB1 A box attenuates experimental colitis in mice." J Gene Med, 2016, 18(10): 261-272.
Zhou, X. et al., "Exogenous High-Mobility Group Box 1 Protein Injection Improves Cardiac Function after Myocardial Infarction: Involvement of Wnt Signaling Activation," Journal of Biomedicine and Biotechnology, 2012, vol. 2012, pp. 1-5.
Arnau, J., et al., "Current strategies for the use of affinity tags and tag removal for the purification of recombinant proteins." Protein Expression and Purification, 2006, 48(1): 1-13.
DeSantis, S., et al., "TNFα Deficiency Results in Increased IL-1β in an Early Onset of Spontaneous Murine Colitis." Cell Death and Disease, 2017, 8: e2993, pp. 1-7.
Frankel, A.E., et al., "Characterization of diphtheria fusion proteins targeted to the human interleukin-3 receptor." Protein Engineering, 2000, 13(8): 575-581.
Hu, Z., et al., "Role of high-mobility group box 1 protein in inflammatory bowel disease." Inflammation Research, 2015, 64(8): 557-563.
Lemp, M.A., et al., "The Definition and Classification of Dry Eye Disease: Report of the Definition and Classification Subcommittee of the International Dry Eye Workshop." The Ocular Surface, 2007, 5(2): Abstract.
O'Callaghan, A., et al., "HMGB1 as a Key Mediator of Tissue Response to Injury: Roles in Inflammation and Tissue Repair." European Surgery, 2006, 38: Abstract.
Seffernick, J. L., et al., "Melamine Deaminase and Atrazine Chlorohydrolase: 98 Percent Identical but Functionally Different." Journal of Bacteriology, 2001, 183(8): 2405-2410.
Tamai, K. et al., U.S. Appl. No. 17/281,862, "Peptide Possessing Mesenchymal-Stem-Cell Mobilizing Activity.", filed Mar. 31, 2021.
Tamai, K. et al., U.S. Appl. No. 17/282,872, "Disease Treatment Drug Based On Mesenchymal-Stem-Cell Mobilization.", filed Apr. 5, 2021.
Tokuriki, N., et al., "Stability effects of mutations and protein evolvability." Current Opinion in Structural Biology, 2009, 19(5): 596-604.
Walfish, A.E., et al., "Crohn Disease (Regional Enteritis; Granulomatou Ileitis; Granulomatous Ileocolitis)," Merck Manual Professional Version, 2020, pp. 1-7.
Walfish, A.E., et al., "Overview of Inflammatory Bowel Disease," Merck Manual Professional Version, 2020, pp. 1-3.
Walfish, A.E., et al., "Ulcerative Colitis," Merck Manual Professional Version, 2020, pp. 1-8.
Whisstock, J. C., et al., "Prediction of Protein Function from Protein Sequence and Structure." Quarterly Reviews of Biophysics, 2003, 36(3): 307-340.
Witkowski, A., et al., "Conversion of a β-Ketoacyl Synthase to a Malonyl Decarboxylase by Replacement of the Active-Site Cysteine with Glutamine." Biochemistry, 1999, 38(36): 11643-11650.
Zhou, X., et al., "Section 2 The translation process of genetic information." Molecular Genetics, 1992, pp. 141-143.
Zhou, Y.-H., et al., "High mobility group box 1 protein attenuates myocardial ischemia reperfusion injury via inhibition of the p38 mitogen-activated protein kinase signaling pathway." Experimental and Therapeutic Medicine, 2017, 14: 1582-1588.
Andersson, Ulf et al. "HMGB1 is a therapeutic target for sterile inflammation and infection." Annual Review of Immunology 29: 39-162 (Year: 2011).
Andrassy, Martin et al. "High-Mobility Group Box-1 in Ischemia-Reperfusion Injury of the Heart." Circulation 117 (25): 3216-26 (Jun. 24, 2008).
Aikawa, Eriko et al. "HMGB1 accelerates skin regeneration by inducing bone marrow mesenchymal stromal cells." Journal of Dermatological Science 84(1): e51 (Year: 2016).
Chan, James K. et al. "Alarmins: awaiting a clinical response." The Journal of Clinical Investigation 122(8): 2711-2719 (Year: 2012).
Freitag, Julien et al. "The effect of autologous adipose derived mesenchymal stem cell therapy in the treatment of a large osteochondral defect of the knee following unsuccessful surgical intervention of osteochondritis dissecans—a case study." BMC Musculoskeletal Disorders 18: 298-308 (Year: 2017).
Lee, Geoffrey et al. "Fully reduced HMGB1 accelerates the regeneration of multiple tissues by transitioning stem cells to GAlert." Proceedings of the National Academy of Sciences 115(19): E4463-E4472 (Year: 2018).
Nickoloff, Brian. J. and Nestle, Frank O. "Recent insights into the immunopathogenesis of psoriasis provide new therapeutic opportunities." The Journal of Clinical Investigation 113(12): 1664-1675 (Year: 2014).
Nojiri, Shunsuki et al. "Synthesized HMGB1 peptide attenuates liver inflammation and suppresses fibrosis in mice." Inflammation and Regeneration 41: 1-15 (Sep. 27, 2021).
Tamai, Katsuto et al., U.S. Appl. No. 17/517,967, "Agents for Promoting Tissue Regeneration by Recruiting Bone Marrow Mesenchymal Stem Cells and/or Pluripotent Stem Cells into Blood.", filed Nov. 3, 2021.
Tamai, Katsuto et al., U.S. Appl. No. 17/817,084, "Therapeutic Agent for Psoriasis", filed Aug. 3, 2022.
Tamilselvi, E. et al. "Association of Disease Severity with IL-1 levels in Methotrexate-treated Psoriasis Patients." Scandinavian Journal of Immunology 78: 545-553 (Year: 2013).
Taniguchi, Noboru et al. "Stage-Specific Secretion of HMGB1 in Cartilage Regulates Endochondral Ossification." Molecular and Cellular Biology 27(16): 5650-5663 (Year 2007).
WHO Drug Information. vol. 32 No.1 Appendix 5 (2018): p. 155.
Musumeci, Domenica et al. "An overview on HMGB1 inhibitors as potential therapeutic agents in HMGB1-related pathologies." Pharmacology and Therapeutics. 141: 347-57 (Year: 2014).
Ahrens, N., et al., "Mesenchymal Stem Cell Content of Human Vertebral Bone Marrow." Transplantation, 2004, 78 (6): 925-929.
Alshorafa, A.K.H., et al., "Psoriasis is Associated with Low Serum Levels of Hydrogen Sulfide, a Potential Anti- Inflammatory Molecule." Tohoku J. Exp. Med., 2012, 228(4): 325-332.
Baer, P.C., et al., "Comprehensive Phenotypic Characterization of Human Adipose-Derived Stromal/Stem Cells and Their Subsets by a High Throughput Technology." Stem Cells and Development, 2013, 22(2): 330-339.
Goodman, W.A., et al., "IL-6 Signaling in Psoriasis Prevents Immune Suppression by Regulatory T Cells." J Immunol., 2009, 183(5): 3170-3176.
Grossman, R.M., et al., "Interleukin 6 is expressed in high levels in psoriatic skin and stimulates proliferation of cultured human keratinocytes."Proc. Natl. Acad. Sci. USA, Aug. 1989, 86(16): 6367-6371.

(56) References Cited

OTHER PUBLICATIONS

Kwak, M.S., et al., "Immunological Significance of HMGB1 Post-Translational Modification and Redox Biology." Frontiers in Immunology, Jun. 2020, 11(1189): pp. 1-16.
Lee, S.A., et al., "The Role of High Mobility Group Box 1 in Innate Immunity." Yonsei Med J, 2014, 55(5): 1165-1176.
Morikawa, S., et al., "Prospective identification, isolation, and systemic transplantation of multipotent mesenchymal stem cells in urine bone marrow." The Journal of Experimental Medicine, 2009, 206(11): 2483-2496.
Neuner, P., et al., "Increased IL-6 Production by Monocytes and Keratinocytes in Patients with Psoriasis." J Invest Dermatol., 1991, 97(1): 27-33.
PROCR gene—Protein C Receptor, Protein Coding., Weizmann Institute of Science, Downloaded from https://www.genecards.org/cgi-bin/carddisp.pl?gene=PROCR, accessed Mar. 31, 2023.
Sidney, L.E., et al., "Concise Review: Evidence for CD34 as a Common Marker for Diverse Progenitors." Stem Cells, 2014, 32(6): 1380-1389.
Suchacki, K.J., et al., "Bone marrow adipose tissue: formation, function and regulation." Curr Opin Pharmacol, 2016, 28:50-56.
Tamai, Katsuto et al. U.S. Appl. No. 17/995,017, "Peptide having Mesenchymal Stem Cell Mobilizing Activity.", filed Sep. 29, 2022.
Tamai, Katsuto et al. U.S. Appl. No. 18/069,421, "Peptide for Inducing Regeneration of Tissue and use Thereof.", filed Dec. 21, 2022.
Tamai, Katsuto et al. U.S. Appl. No. 18/152,249, "Pharmaceuticals That Promote Functional Regeneration of Damaged Tissues.", filed Jan. 10, 2023.
Wynn, T.A., et al., "Mechanisms of fibrosis: therapeutic translation for fibrotic disease." Nat Med, 2012, 18(7): 1028-1040.
Yang, H., et al., "The many faces of HMGB1: molecular structure-functional activity in inflammation, apoptosis, and chemotaxis." Journal of Leukocyte Biology, Jun. 2013, 93(6): 865-873.
Zaandarashvili, L., et al., "Real-time Kinetics of High-mobility Group Box 1 (HMGB1) Oxidation in Extracellular Fluids Studied by in Situ Protein NMR Spectroscopy." The Journal of Biological Chemistry, 2013, 288(17): 11621-11627.
Zhao, J., et al., "The Study Progression of the Role of HMGBI in Ischemic Heart Failure." Molecular Cardiology of China, 2014, pp. 1169-1171.
De Meyer, S.F. et al., "Extracellular Chromatin Is an Important Mediator of Ischemic Stroke in Mice." Arterioscler Throm Vasc Biol, 2012, 32: 1884-1891.
Drumm, M.L. et al., "Genetic Variation and Clinical Heterogeneity in Cystic Fibrosis." Annu Rev Pathol Mech Dis, 2012, 7: 267-282.
Ko, E., et al., "SERPINA3 is a key modulator of HNRNP-L transcription activity against oxidative stress in HCC." Redox Biology, 2019, 24(101217): 1-10.
Kolundzic, E., et al., "FACT sets a Barrier for Cell Fate Reprogramming in Caenorhabditis elegans and Human Cells." Developmental Cell, 2018, 46: 611-626, e1-e12.
Leenaars, M., et al., "Critical Steps in the Production of Polyclonal and Monoclonal Antibodies: Evaluation and Recommednations." ILAR Journal, 2005, 46(3): 269-279.
SPT16 (D7I2K) Rabbit Monocolonal Antibody, from https://www.cellssignal.com/products/primary-antibodies/spt16-d7i2k-rabbit-mab/1219?N=572736551=4294956287&Nrpp=100&No=%7Boffset%7D&fromPage=plp, pp. 1-5, accessed Nov. 1, 2023.
Yampolsky, L.Y., et al., "The Exchangability of Amino Acids in Proteins." Genetics, 2005, 170(4): 1459-1472.
Danese, S., et al., "Randomised trial and open-label extension study of anti-interleukin-6 antibody in Crohn's disease (ANDANTE I and II.)" Gut, 2019, 68(1): 40-48.
ICH, GCP, US Clinical Trials Registry, Clinical Trial NCT01287897, A Study to Assess the Efficacy and Safety of PF-042236921 in Subjects with Crohn's Disease who Failed Anti-TNF Therapy (ANDANTE), <<accessed from the Internet Dec. 1, 2023, https://ichgcp.net/clinical-trials-registry/NCT01287897>>.
Ito, H., et al., "A Pilot Randomized Trial of a Human Anti-Interleukin-6 Receptor Monoclonal Antibody in Active Crohn's Disease." Gastroenterology, 2004, 126(4): 989-996.
Nam, Y.-S., et al., "Negative impact of bone-marrow-derived mesenchymal stem cells on dextran sulfate sodium-induced colitis." World of Gastroenterology, 2015, 21(7): 2030-2039.
Sommer, J., et al., "Interleukin-6, but not the interleukin-6 antibody plays a role in recovery from dextran sulfate sodium-induced colitis" International Journal of Molecular Medicine, 2014, 34(3): 651-660.

\* cited by examiner

PDGFRα+CD105+DAPI staining x200

SEQUENCE LISTING

```
<160> NUMBER OF SEQ ID NOS: 3

<210> SEQ ID NO 1
<211> LENGTH: 44
<212> TYPE: PRT
<213> ORGANISM: Artificial sequence
<220> FEATURE:
```

<223> OTHER INFORMATION: An artificially synthesized peptide sequence

<400> SEQUENCE: 1

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys
        35                  40

<210> SEQ ID NO 2
<211> LENGTH: 215
<212> TYPE: PRT
<213> ORGANISM: Homo sapiens

<400> SEQUENCE: 2

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Lys Glu Glu Glu Glu Asp Glu Glu
            180                 185                 190

Asp Glu Glu Asp Glu Glu Glu Glu Asp Glu Glu Asp Glu Asp Glu Glu
        195                 200                 205

Glu Glu Asp Asp Asp Asp Glu
    210                 215

<210> SEQ ID NO 3
<211> LENGTH: 648
<212> TYPE: DNA
<213> ORGANISM: Homo sapiens

<400> SEQUENCE: 3
atgggcaaag gagatcctaa gaagccgaga ggcaaaatgt catcatatgc atttttttgtg    60 caaacttgtc gggaggagca taagaagaag cacccagatg cttcagtcaa cttctcagag    120
ttttctaaga agtgctcaga gaggtggaag accatgtctg ctaaagagaa aggaaaattt    180
gaagatatgg caaaagcgga caaggcccgt tatgaaagag aaatgaaaac ctatatccct    240

```
cccaaagggg agacaaaaaa gaagttcaag gatcccaatg cacccaagag gcctccttcg    300
gccttcttcc tcttctgctc tgagtatcgc ccaaaaatca aaggagaaca tcctggcctg    360
tccattggtg atgttgcgaa gaaactggga gagatgtgga ataacactgc tgcagatgac    420
aagcagcctt atgaaaagaa ggctgcgaag ctgaaggaaa aatacgaaaa ggatattgct    480
gcatatcgag ctaaaggaaa gcctgatgca gcaaaaaagg gagttgtcaa ggctgaaaaa    540
agcaagaaaa agaaggaaga ggaggaagat gaggaagatg aagaggatga ggaggaggag    600
gaagatgaag aagatgaaga tgaagaagaa gatgatgatg atgaataa                648
```

THERAPEUTIC AGENT FOR CARDIOMYOPATHY, OLD MYOCARDIAL INFARCTION AND CHRONIC HEART FAILURE

CROSS REFERENCE TO A RELATED APPLICATION

This application is a National Stage Application of International Application Number PCT/JP2018/002373, filed Jan. 26, 2018; which claims priority to Japanese Application No. 2017-013293, filed Jan. 27, 2017; and Japanese Application No. 2017-151788, filed Aug. 4, 2017.

The Sequence Listing for this application is labeled "6_G6-A1601Psq.txt", which was created on Jul. 5, 2019, and is 4 KB. The entire content is incorporated herein by reference in its entirety.

TECHNICAL FIELD

The present application relates to pharmaceutical compositions comprising a fragment peptide of the HMGB1 protein for the prevention and/or treatment of cardiomyopathy, old myocardial infarction, and chronic heart failure.

BACKGROUND ART

Cardiomyopathy is defined as a "disease of myocardium associated with cardiac dysfunction" often accompanied by structural abnormalities of the heart, such as cardiomegaly, cardiomyocyte hypertrophy, and myocardial fibrosis; and presents symptoms of chronic heart failure as it progresses. Secondary cardiomyopathy may be ameliorated by treatment of the primary disease, but there is still no definitive treatment for idiopathic cardiomyopathy.

Myocardial infarction, which causes myocardial necrosis due to coronary artery occlusion, is a major underlying disorder of heart disease which is the leading cause of death in developed countries (first in the United States and second in Japan). While the acute-phase treatment outcome has been improved by the advancement of diagnostic technologies, catheter treatment, and coronary artery bypass grafting, cardiomegaly and cardiac hypertrophy progress and chronic heart failure often occur in cases of extensive infarction, severe reperfusion failure, and cases that have missed the opportunity for treatment.

When chronic heart failure caused by cardiomyopathy or old myocardial infarction becomes severe, existing drugs for chronic heart failure (ACE inhibitors, β blockers, etc.) cannot achieve sufficient improving effects in some cases, and heart transplantation may be required. However, the transplantation waiting period in Japan is as long as about 3 years (Non-Patent Document 1), and complications such as cerebral infarction and device infection often occur during the waiting period. Further, even if a heart transplant is received, there are problems such as increased risk of infectious diseases due to side effects of immunosuppressants which require to be continuously administered subsequently and possible complications such as coronary artery lesions; and the 10-year survival rate after the heart transplantation is about 50% (Non-Patent Document 2). Under such circumstances, development of new therapeutic agents for cardiomyopathy and old myocardial infarction as well as chronic heart failure caused thereby is desired.

Recently, regenerative medicine using mesenchymal stem cells has attracted attention, and regarding chronic heart failure after myocardial infarction, it has been reported that a cardiac function improving effect could be obtained by directly transplanting a cell sheet made of mesenchymal stem cells derived from the egg membrane, bone marrow, or adipose tissue into the heart in an animal model of chronic myocardial infarction (Non-Patent Document 3 and Patent Document 1). However, transplantation of the cell sheet is very burdensome to the patient as it requires a thoracotomy operation, and it cannot be applied to patients whose operation is difficult due to factors such as advanced age.

Also, the mechanism in which an injured tissue releases bone-marrow pluripotent stem cell recruiting factors into the blood to induce regeneration of the injured tissue has been confirmed. In previous studies, the present inventors found that fragment peptides of the High mobility group box 1 (HMGB1) protein mobilize bone marrow mesenchymal stem cells from the bone marrow into the peripheral blood, and that administration of the fragment peptides in the acute phase of myocardial infarction leads to accumulation of bone marrow-derived mesenchymal stem cells at and near the site of infarction, resulting in an improved cardiac function (Patent Documents 2 and 3).

However, in the acute phase of myocardial infarction, a large quantity of cardiomyocytes are rapidly necrotized by ischemia and a strong inflammatory reaction is generated, whereas cardiomyopathy does not generally cause such phenomena and is characterized in that structural abnormalities such as cardiomegaly, cardiomyocyte hypertrophy, and myocardial fibrosis progress slowly. The pathologies of these two are greatly different. Necrosis and inflammation of cardiomyocytes are also settled in old myocardial infarction, and the progression of cardiomegaly and cardiac hypertrophy is characteristic for the disease. Therefore, it was unclear whether fragment peptides of the HMGB1 protein exert therapeutic effects on cardiomyopathy and old myocardial infarction.

CITATION LIST

Non-Patent Documents

Non-Patent Document 1: Fukushima et al., "Registry Report on Heart Transplantation in Japan (June 2016)," Circulation Journal (Advance Publication, Jan. 6, 2017, Article ID: CJ-16-0976)

Non-Patent Document 2: Lund et al., "The Registry of the International Society for Heart and Lung Transplantation: Thirty-third Adult Heart Transplantation Report-2016; Focus Theme: Primary Diagnostic Indications for Transplant," J Heart Lung Transplant. 2016 October; 35(10): 1158-1169

Non-Patent Document 3: Ishikane Shin, "Development of multi-growth factor secreted fetal membrane-derived mesenchymal stem cell sheets" Jun. 11, 2014, Grants-in-Aid for Scientific Research, Research report

Patent Documents

Patent Document 1: WO2006/080434
Patent Document 2: WO2012/147470
Patent Document 3: WO2014/065347

SUMMARY OF THE INVENTION

Problems to be Solved by the Invention

An objective of the present application is to provide new pharmaceuticals effective for the prevention and/or treatment of cardiomyopathy and old myocardial infarction as well as the chronic heart failure resulting therefrom. Another objective of the present application is to provide new pharmaceuticals that are effective for the prevention and/or treatment of cardiac diseases associated with structural abnormalities and/or dysfunction of the heart.

Means for Solving the Problems

As a result of studying the effects of HMGB1 fragment peptides in cardiomyopathy, the present inventors found that HMGB1 fragment peptides having particular amino acid sequences exhibit effects of improving cardiac functions, inhibiting structural abnormalities of the heart (cardiomyocyte hypertrophy and myocardial fibrosis), and promoting angiogenesis in an animal model of dilated cardiomyopathy. The present inventors also discovered that in an animal model of ischemic cardiomyopathy resulting from old myocardial infarction, the specific HMGB1 fragment peptides exhibit effects of improving cardiac function, inhibiting structural abnormalities of the heart (cardiomegaly, cardiomyocyte hypertrophy, and myocardial fibrosis), and promoting angiogenesis. Furthermore, the present inventors found that the specific HMGB1 fragment peptides exhibit an inhibitory effect on structural abnormalities of the heart (cardiomyocyte hypertrophy and myocardial fibrosis) in a hypertensive cardiomyopathy animal model. Thus, the present application provides pharmaceutical compositions comprising the specific HMGB1 fragment peptides for the prevention and/or treatment of cardiomyopathy and old myocardial infarction and chronic heart failure resulting therefrom. The specific HMGB1 fragment peptides also inhibit structural abnormalities and/or dysfunction of the heart in cardiomyopathy and inhibit structural abnormalities and dysfunction of the heart in old myocardial infarction. Thus, the present application provides pharmaceutical compositions comprising the specific HMGB1 fragment peptides for the prevention and/or treatment of cardiac diseases associated with structural abnormalities and/or dysfunction of the heart.

That is, the present application provides the following inventions:

[1] A pharmaceutical composition for preventing and/or treating a cardiac disease associated with a structural abnormality and/or dysfunction of the heart, which comprises the substance described in any of (a) to (c) below (herein below referred to as substance A):
(a) an HMGB1 fragment peptide comprising the amino acid sequence described in SEQ ID NO: 1;
(b) a peptide comprising an amino acid sequence in which one or more amino acids have been substituted, deleted, inserted, or added in the amino acid sequence described in SEQ ID NO: 1 and having an activity of stimulating cell migration; and
(c) a peptide comprising an amino acid sequence having about 80% or more sequence identity with the amino acid sequence described in SEQ ID NO: 1 and having an activity of stimulating cell migration.

[2] The pharmaceutical composition of [1], wherein the cardiac disease associated with a structural abnormality and/or dysfunction of the heart is cardiomyopathy.

[3] The pharmaceutical composition of [2], wherein the cardiomyopathy is idiopathic cardiomyopathy.

[4] The pharmaceutical composition of [3], wherein the idiopathic cardiomyopathy is selected from the group consisting of dilated cardiomyopathy, hypertrophic cardiomyopathy, restrictive cardiomyopathy, and arrhythmogenic right ventricular cardiomyopathy.

[5] The pharmaceutical composition of [2], wherein the cardiomyopathy is a secondary cardiomyopathy.

[6] The pharmaceutical composition of [5], wherein the secondary cardiomyopathy is selected from the group consisting of ischemic cardiomyopathy, hypertensive cardiomyopathy, valvular cardiomyopathy, drug-induced cardiomyopathy, alcoholic cardiomyopathy, mitochondrial cardiomyopathy, cardiomyopathy caused by cardiac sarcoidosis, cardiomyopathy caused by cardiac amyloidosis, cardiomyopathy caused by myocarditis, cardiomyopathy caused by muscular dystrophy, cardiomyopathy caused by cardiac Fabry's disease, and peripartum cardiomyopathy.

[7] The pharmaceutical composition of [1], wherein the cardiac disease associated with a structural abnormality and/or dysfunction of the heart is old myocardial infarction.

[8] A pharmaceutical composition comprising substance A, which is for preventing and/or treating a chronic heart failure caused by cardiomyopathy or old myocardial infarction.

[9] A pharmaceutical composition comprising substance A, which is for inhibiting a structural abnormality of the heart selected from the group consisting of cardiomegaly, cardiomyocyte hypertrophy, and myocardial fibrosis in a patient with cardiomyopathy or old myocardial infarction.

[10] A pharmaceutical composition comprising substance A, which is for the prevention and/or treatment of cardiomyopathy selected from the group consisting of dilated cardiomyopathy, ischemic cardiomyopathy, and hypertensive cardiomyopathy.

[11] The pharmaceutical composition of [10], wherein the ischemic cardiomyopathy is caused by old myocardial infarction.

[12] A pharmaceutical composition comprising substance A, which is for the prevention and/or treatment of a chronic heart failure caused by cardiomyopathy selected from the group consisting of dilated cardiomyopathy, ischemic cardiomyopathy, and hypertensive cardiomyopathy.

[13] The pharmaceutical composition of [12], wherein the ischemic cardiomyopathy is caused by old myocardial infarction.

[14] The pharmaceutical composition of [12], wherein the chronic heart failure is caused by dilated cardiomyopathy or ischemic cardiomyopathy.

[15] The pharmaceutical composition of [14], wherein the chronic heart failure caused by dilated cardiomyopathy or ischemic cardiomyopathy is HFrEF.

[16] The pharmaceutical composition of [12], wherein the chronic heart failure is caused by hypertensive cardiomyopathy.

[17] The pharmaceutical composition of [16], wherein the chronic heart failure caused by hypertensive cardiomyopathy is HFpEF.

[A1] A method of preventing and/or treating a cardiac disease associated with a structural abnormality and/or dysfunction of the heart, which comprises administering to a subject an effective amount of substance A.

[A2] The method of [A1], wherein the cardiac disease associated with structural abnormality and/or dysfunction of the heart is cardiomyopathy.

[A3] The method of [A2], wherein the cardiomyopathy is idiopathic cardiomyopathy.

[A4] The method of [A3], wherein the idiopathic cardiomyopathy is selected from the group consisting of dilated cardiomyopathy, hypertrophic cardiomyopathy, restrictive cardiomyopathy, and arrhythmogenic right ventricular cardiomyopathy.

[A5] The method of [A2], wherein the cardiomyopathy is a secondary cardiomyopathy.

[A6] The method of [A5], wherein the secondary cardiomyopathy is selected from the group consisting of ischemic cardiomyopathy, hypertensive cardiomyopathy, valvular cardiomyopathy, drug-induced cardiomyopathy, alcoholic cardiomyopathy, mitochondrial cardiomyopathy, cardiomyopathy caused by cardiac sarcoidosis, cardiomyopathy caused by cardiac amyloidosis, cardiomyopathy caused by myocarditis, cardiomyopathy caused by muscular dystrophy, cardiomyopathy caused by cardiac Fabry's disease, and peripartum cardiomyopathy.

[A7] The method of [A1], wherein the cardiac disease associated with structural abnormality and/or dysfunction of the heart is old myocardial infarction.

[A8] A method of preventing and/or treating a chronic heart failure caused by cardiomyopathy or old myocardial infarction, which comprises administering to a subject an effective amount of substance A.

[A9] A method of inhibiting a structural abnormality of the heart selected from the group consisting of cardiomegaly, cardiomyocyte hypertrophy, and myocardial fibrosis in a patient with cardiomyopathy or old myocardial infarction, which comprises administering to a subject an effective amount of substance A.

[A10] A method of preventing and/or treating a cardiomyopathy selected from the group consisting of dilated cardiomyopathy, ischemic cardiomyopathy, and hypertensive cardiomyopathy, which comprises administering to a subject an effective amount of substance A.

[A11] The method of [A10], wherein the ischemic cardiomyopathy is caused by old myocardial infarction.

[A12] A method of preventing and/or treating a chronic heart failure caused by a cardiomyopathy selected from the group consisting of dilated cardiomyopathy, ischemic cardiomyopathy, and hypertensive cardiomyopathy, which comprises administering to a subject an effective amount of substance A.

[A13] The method of [A12], wherein the ischemic cardiomyopathy is caused by old myocardial infarction.

[A14] The method of [A12], wherein the chronic heart failure is caused by dilated cardiomyopathy or ischemic cardiomyopathy.

[A15] The method of [A14], wherein the chronic heart failure caused by dilated cardiomyopathy or ischemic cardiomyopathy is HFrEF.

[A16] The method of [A12], wherein the chronic heart failure is caused by hypertensive cardiomyopathy.

[A17] The method of [A16], wherein the chronic heart failure caused by hypertensive cardiomyopathy is HFpEF.

[B1] Substance A for use in the prevention and/or treatment of a cardiac disease associated with structural abnormality and/or dysfunction of the heart.

[B2] Substance A of [B1], wherein the cardiac disease associated with structural abnormality and/or dysfunction of the heart is cardiomyopathy.

[B3] Substance A of [B2], wherein the cardiomyopathy is idiopathic cardiomyopathy.

[B4] Substance A of [B3], wherein the idiopathic cardiomyopathy is selected from the group consisting of dilated cardiomyopathy, hypertrophic cardiomyopathy, restrictive cardiomyopathy, and arrhythmogenic right ventricular cardiomyopathy.

[B5] Substance A of [B2], wherein the cardiomyopathy is a secondary cardiomyopathy.

[B6] Substance A of [B5], wherein the secondary cardiomyopathy is selected from the group consisting of ischemic cardiomyopathy, hypertensive cardiomyopathy, valvular cardiomyopathy, drug-induced cardiomyopathy, alcoholic cardiomyopathy, mitochondrial cardiomyopathy, cardiomyopathy caused by cardiac sarcoidosis, cardiomyopathy caused by cardiac amyloidosis, cardiomyopathy caused by myocarditis, cardiomyopathy caused by muscular dystrophy, cardiomyopathy caused by cardiac Fabry's disease, and peripartum cardiomyopathy.

[B7] Substance A of [B1], wherein the cardiac disease associated with structural abnormality and/or dysfunction of the heart is old myocardial infarction.

[B8] Substance A for use in the prevention and/or treatment of a chronic heart failure caused by cardiomyopathy or old myocardial infarction.

[B9] Substance A for use in inhibiting a structural abnormality of the heart selected from the group consisting of cardiomegaly, cardiomyocyte hypertrophy, and myocardial fibrosis in a patient with cardiomyopathy or old myocardial infarction.

[B10] Substance A for use in the prevention and/or treatment of a cardiomyopathy selected from the group consisting of dilated cardiomyopathy, ischemic cardiomyopathy, and hypertensive cardiomyopathy.

[B11] Substance A of [B10], wherein the ischemic cardiomyopathy is caused by old myocardial infarction.

[B12] Substance A for use in the prevention and/or treatment of a chronic heart failure caused by cardiomyopathy selected from the group consisting of dilated cardiomyopathy, ischemic cardiomyopathy, and hypertensive cardiomyopathy.

[B13] Substance A of [B12], wherein the ischemic cardiomyopathy is caused by old myocardial infarction.

[B14] Substance A of [B12], wherein the chronic heart failure is caused by dilated cardiomyopathy or ischemic cardiomyopathy.

[B15] Substance A of [B14], wherein the chronic heart failure caused by dilated cardiomyopathy or ischemic cardiomyopathy is HFrEF.

[B16] Substance A of [B12], wherein the chronic heart failure is caused by hypertensive cardiomyopathy.

[B17] Substance A of [B16], wherein the chronic heart failure caused by hypertensive cardiomyopathy is HFpEF.

[C1] Use of Substance A in the manufacture of a medicament for the prevention and/or treatment of a cardiac disease associated with structural abnormality and/or dysfunction of the heart.

[C2] The use of [C1], wherein the cardiac disease associated with structural abnormality and/or dysfunction of the heart is cardiomyopathy.

[C3] The use of [C2], wherein the cardiomyopathy is idiopathic cardiomyopathy.

[C4] The use of [C3], wherein the idiopathic cardiomyopathy is selected from the group consisting of dilated cardiomyopathy, hypertrophic cardiomyopathy, restrictive cardiomyopathy, and arrhythmogenic right ventricular cardiomyopathy.

[C5] The use of [C2], wherein the cardiomyopathy is a secondary cardiomyopathy.

[C6] The use of [C5], wherein the secondary cardiomyopathy is selected from the group consisting of ischemic cardiomyopathy, hypertensive cardiomyopathy, valvular cardiomyopathy, drug-induced cardiomyopathy, alcoholic cardiomyopathy, mitochondrial cardiomyopathy, cardiomyopathy caused by cardiac sarcoidosis, cardiomyopathy caused by cardiac amyloidosis, cardiomyopathy caused by myocarditis, cardiomyopathy caused by muscular dystrophy, cardiomyopathy caused by cardiac Fabry's disease, and peripartum cardiomyopathy.

[C7] The use of [C1], wherein the cardiac disease associated with structural abnormality and/or dysfunction of the heart is old myocardial infarction.

[C8] Use of substance A in the manufacture of a medicament for the prevention and/or treatment of a chronic heart failure caused by cardiomyopathy or old myocardial infarction.

[C9] Use of substance A in the manufacture of a medicament for inhibiting a structural abnormality of the heart selected from the group consisting of cardiomegaly, cardiomyocyte hypertrophy, and myocardial fibrosis in a patient with cardiomyopathy or old myocardial infarction.

[C10] Use of substance A in the manufacture of a medicament for the prevention and/or treatment of a cardiomyopathy selected from the group consisting of dilated cardiomyopathy, ischemic cardiomyopathy, and hypertensive cardiomyopathy.

[C11] The use of [C10], wherein the ischemic cardiomyopathy is caused by old myocardial infarction.

[C12] Use of substance A in the manufacture of a medicament for the prevention and/or treatment of a chronic heart failure caused by cardiomyopathy selected from the group consisting of dilated cardiomyopathy, ischemic cardiomyopathy, and hypertensive cardiomyopathy.

[C13] The use of [C12], wherein the ischemic cardiomyopathy is caused by old myocardial infarction.

[C14] The use of [C12], wherein the chronic heart failure is caused by dilated cardiomyopathy or ischemic cardiomyopathy.

[C15] The use of [C14], wherein the chronic heart failure caused by dilated cardiomyopathy or ischemic cardiomyopathy is HFrEF.

[C16] The use of [C12], wherein the chronic heart failure is caused by hypertensive cardiomyopathy.

[C17] The use of [C16], wherein the chronic heart failure caused by hypertensive cardiomyopathy is HFpEF.

MODE FOR CARRYING OUT THE INVENTION

Figure 1:
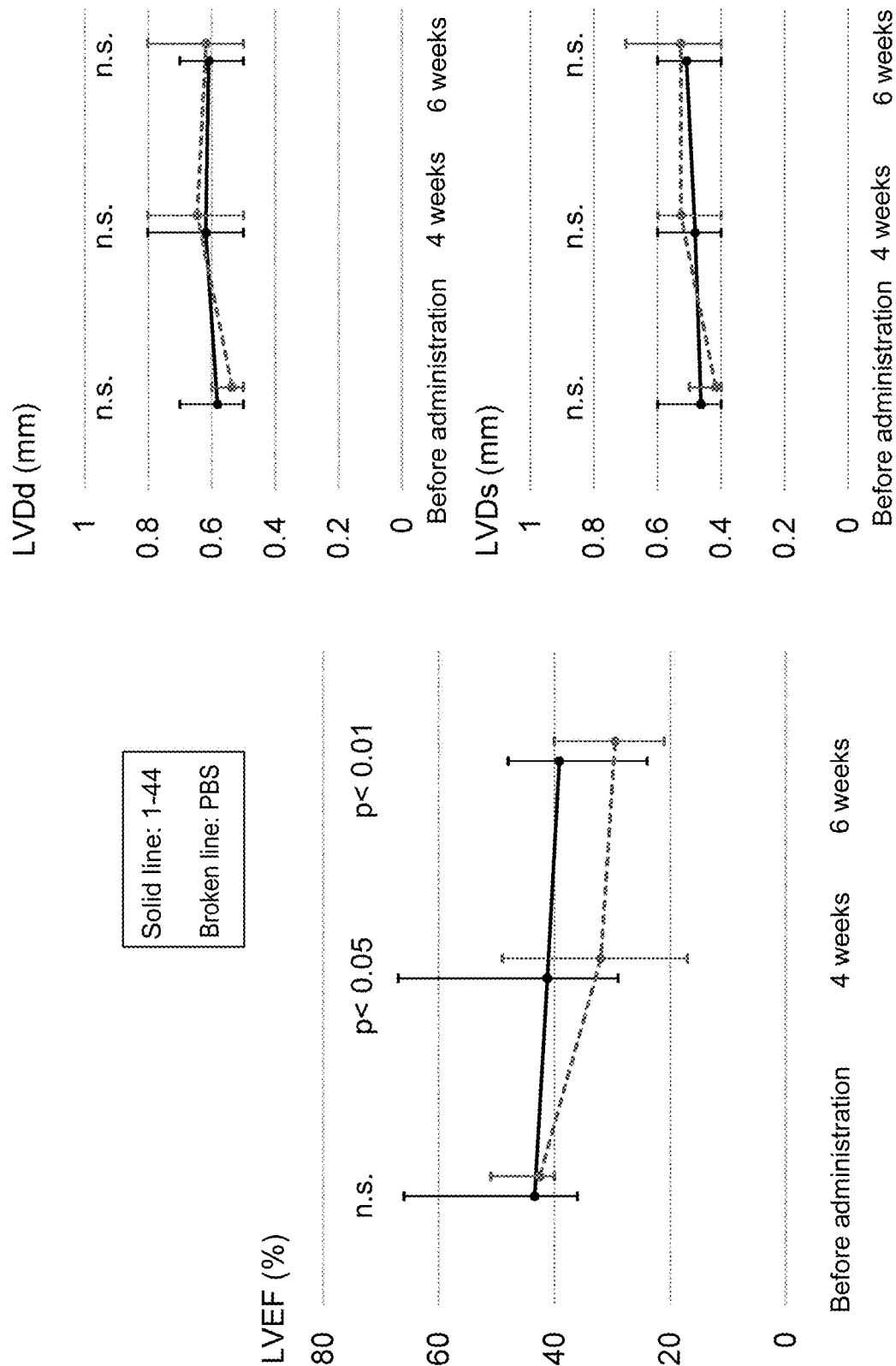
FIG. 1 presents graphs showing the results of measurement of left ventricular ejection fraction (LVEF), left ventricular end-diastolic diameter (LVDd), and left ventricular end-systolic diameter (LVDs) in the HMGB1 peptide (1-44) and PBS groups before, 4 weeks after, and 6 weeks after administration.

The present application provides pharmaceutical compositions for the prevention and/or treatment of cardiac diseases accompanied by structural abnormality and/or dysfunction of the heart, which comprise an HMGB1 fragment peptide comprising the amino acid sequence as described in SEQ ID NO: 1.

In the present application, structural abnormalities of the heart include, but are not limited to, cardiomegaly, cardiomyocyte hypertrophy, myocardial fibrosis, and such. In one aspect, the structural abnormality of the heart is selected from the group consisting of cardiomegaly, cardiomyocyte hypertrophy, and myocardial fibrosis.

As used in the present application, dysfunction of the heart (cardiac dysfunction) refers to impairment of the pump function by which the heart takes in and sends out blood, including impaired contractility and impaired diastolic capacity. In one aspect, dysfunction of the heart is selected from the group consisting of impaired contractility and impaired diastolic capacity. In another aspect, dysfunction of the heart is selected from the group consisting of impaired contractility and impaired diastolic capacity of the ventricle. In another aspect, dysfunction of the heart is selected from the group consisting of impaired contractility and impaired diastolic capacity of the left ventricle.

The present application provides pharmaceutical compositions for the prevention and/or treatment of cardiomyopathy, which comprise an HMGB1 fragment peptide comprising the amino acid sequence described in SEQ ID NO: 1.

In the present application, "cardiomyopathy" refers to a myocardial disease accompanied by cardiac dysfunction. Also, cardiomyopathy is often accompanied by structural abnormalities of the heart, such as cardiomegaly, cardiomyocyte hypertrophy, and myocardial fibrosis.

Among the cardiomyopathies, those having no obvious cause such as hypertension and coronary artery disease and having lesions predominantly in the myocardium are called idiopathic cardiomyopathy, and those having a clear relationship with the cause disease or systemic disease are called secondary cardiomyopathy.

Idiopathic cardiomyopathies include, but are not limited to, dilated cardiomyopathy, hypertrophic cardiomyopathy, restrictive cardiomyopathy, arrhythmogenic right ventricular cardiomyopathy, and unclassified cardiomyopathy. "Dilated cardiomyopathy" refers to a disease characterized by left ventricular enlargement and impaired left ventricular contractility, without coincidence of a coronary artery disease or an abnormal load condition (hypertension or valvular disease) that can lead to diffuse contractile impairment.

Secondary cardiomyopathies include, but are not limited to, ischemic cardiomyopathy, hypertensive cardiomyopathy, valvular cardiomyopathy, drug-induced cardiomyopathy, alcoholic cardiomyopathy, mitochondrial cardiomyopathy, cardiomyopathy caused by cardiac sarcoidosis, cardiomyopathy caused by cardiac amyloidosis, cardiomyopathy caused by myocarditis, cardiomyopathy caused by muscular dystrophy, cardiomyopathy caused by cardiac Fabry's disease, and peripartum cardiomyopathy. In one aspect, the cardiomyopathy caused by muscular dystrophy is cardiomyopathy caused by Duchenne type-, Becker type-, or Emery-Dreifuss type-muscular dystrophy.

In the present application, "ischemic cardiomyopathy" refers to a disease in which an ischemic heart disease (old myocardial infarction or angina pectoris) causes cardiomegaly and impairment of myocardial contractility. The HMGB1 fragment peptides can prevent and/or treat ischemic cardiomyopathy because the peptides have an inhibitory effect on cardiomegaly and an improving effect on myocardial contractility. In one aspect, the ischemic cardiomyopathy is caused by old myocardial infarction.

In the present application, "hypertensive cardiomyopathy" refers to a disease in which hypertension causes cardiomyocyte hypertrophy and cardiac dysfunction (impaired diastolic capacity or impaired contractility). The HMGB1 fragment peptides can prevent and/or treat hypertensive cardiomyopathy because the peptides can suppress cardiomyocyte hypertrophy caused by hypertension.

In the present application, the term "pharmaceutical composition" is used interchangeably with "pharmaceutical", "drug", and "pharmacological composition".

The present application provides pharmaceutical compositions that comprise an HMGB1 fragment peptide comprising the amino acid sequence described in SEQ ID NO:1 for the treatment of old myocardial infarction.

In the present application, "old myocardial infarction" refers to a condition in which 30 days or more have elapsed after the onset of myocardial infarction in humans (14 days or more after the onset of myocardial infarction in rats), and which is accompanied by a structural abnormality or functional disorder of the heart. Old myocardial infarction with cardiomegaly and impaired cardiac contractility is classified as ischemic cardiomyopathy. Also, in the present application, the term "old myocardial infarction" is used interchangeably with "chronic myocardial infarction".

The HMGB1 fragment peptides in the present application inhibit structural abnormalities (e.g., cardiomegaly, cardiomyocyte hypertrophy, and myocardial fibrosis) and dysfunction (e.g., impaired contractility) of the heart in old myocardial infarction. Also, the HMGB1 fragment peptides of the present application exert an improving effect on cardiac function (e.g., contractility) in cardiomyopathy. Thus, the HMGB1 fragment peptides of the present application are believed to exert broad therapeutic effects on cardiac diseases associated with structural abnormality and/or dysfunction of the heart, such as old myocardial infarction and cardiomyopathy.

The present application also provides pharmaceutical compositions for prevention and/or treatment of a chronic heart failure caused by cardiomyopathy, which comprise an HMGB1 fragment peptide comprising the amino acid sequence described in SEQ ID NO: 1.

Cardiomyopathy leads to a condition of chronic heart failure when cardiac function deteriorates due to progression of the disease state. The HMGB1 fragment peptides can prevent and/or treat chronic heart failure in cardiomyopathy patients because they can suppress structural cardiac abnormalities such as cardiomegaly, cardiomyocyte hypertrophy, and myocardial fibrosis and improve cardiac function in cardiomyopathy.

The present application also provides pharmaceutical compositions for prevention and/or treatment of a chronic heart failure caused by old myocardial infarction, which comprise an HMGB1 fragment peptide comprising the amino acid sequence described in SEQ ID NO: 1.

Old myocardial infarction leads to a state of chronic heart failure as the cardiac function deteriorates due to progression of a structural cardiac abnormality or such. The HMGB1 fragment peptides can prevent and/or treat chronic heart failure in patients with old myocardial infarction because they can suppress structural cardiac abnormalities such as cardiomegaly, cardiomyocyte hypertrophy, and myocardial fibrosis and improve the cardiac function in old myocardial infarction.

In the present application, "chronic heart failure" refers to a disease state in which the pump function of the heart deteriorates due to chronic myocardial impairment, and the absolute and relative volume of blood in proportion to the oxygen demand of the main peripheral organs cannot be pumped out, causing congestion of the lungs, the systemic venous system, or both systems, thereby impeding daily life. The types of chronic heart failure include heart failure with reduced left ventricular ejection fraction (heart failure with reduced ejection fraction: HFrEF) and heart failure with preserved left ventricular ejection fraction (heart failure with preserved ejection fraction: HFpEF). HFrEF is characterized by <50% left ventricular ejection fraction and has impaired contractility. HFpEF is characterized by a left ventricular ejection fraction of 50% or greater and has impaired diastolic capacity. In one aspect, the HFrEF is due to dilated cardiomyopathy or ischemic cardiomyopathy. In one aspect, the HFpEF is due to hypertensive cardiomyopathy.

The present application also provides pharmaceutical compositions for inhibiting a structural abnormality of the heart selected from the group consisting of cardiomegaly, cardiomyocyte hypertrophy, and myocardial fibrosis in patients with cardiomyopathy and old myocardial infarction, which comprise an HMGB1 fragment peptide comprising the amino acid sequence described in SEQ ID NO: 1. In one aspect, the pharmaceutical compositions of the present application are those used in patients with cardiomyopathy and old myocardial infarction to (i) inhibit a structural abnormality of the heart selected from the group consisting of cardiomegaly, cardiomyocyte hypertrophy, and myocardial fibrosis, (ii) promote angiogenesis in the heart, or (iii) improve the contractility or diastolic capacity of the heart. Contractility of the heart includes, but is not limited to, for example, ventricular contractility such as contractility of the left ventricle. Diastolic capacity of the heart includes, but is not limited to, for example, ventricular diastolic capacity such as diastolic capacity of the left ventricle.

In the present application, an HMGB1 fragment peptide comprising the amino acid sequence described in SEQ ID NO:1 refers to a peptide consisting of a portion of an HMGB1 protein and comprising the amino acid sequence described SEQ ID NO:1. Such peptides can be obtained as genetic recombinants (recombinants) by incorporating DNA encoding the peptide into an appropriate expression system, or they can be synthesized artificially.

In the present application, the HMGB1 protein includes, but is not limited to, proteins comprising the amino acid sequence described in SEQ ID NO:2 and proteins encoded by DNAs comprising the base sequence described in SEQ ID NO:3.

The HMGB1 fragment peptide comprising the amino acid sequence described in SEQ ID NO: 1 in the present application include, but is not limited to the following:

1) an HMGB1 fragment peptide comprising the amino acid sequence described in SEQ ID NO: 1 and having an activity to stimulate cell migration;
2) an HMGB1 fragment peptide comprising the amino acid sequence described in SEQ ID NO: 1 and having an activity to stimulate migration of mesenchymal stem cells; and
3) an HMGB1 fragment peptide consisting of the amino acid sequence described in SEQ ID NO: 1.

In the present application, cells whose migration is stimulated by an HMGB1 fragment peptide include, but are not limited to, bone marrow cells or bone marrow-derived cells (e.g., bone marrow stem cells or bone marrow-derived stem cells).

In the present application, "bone marrow cells" refers to cells present in the bone marrow, while "bone marrow-derived cells" refers to "bone marrow cells" mobilized from the bone marrow to the outside of the bone marrow. "Bone marrow cells" may also include undifferentiated cells such as stem cells and progenitor cells present in the bone marrow.

In the present application, cells whose migration is stimulated by an HMGB1 fragment peptide also include, but are not limited to, mesenchymal stem cells. "Mesenchymal stem cells" are cells taken from the bone marrow or other tissues (e.g., blood such as umbilical cord blood, and skin, fat, dental pulp, etc.), which can be cultured and propagated as adherent cells on culture dishes (made of plastic or glass) and having the potential to differentiate into mesenchymal tissues such as bone, cartilage, fat, and muscle. In one aspect, the mesenchymal stem cells also have an ability to differentiate into epithelial and nervous tissues. Mesenchymal stem cells in the present application may exist as a heterogeneous population of cells containing not only stem cells in a narrow sense but also progenitor cells, and they may include, under culture conditions, differentiated cells in addition to the narrow-sense stem cells and/or progenitor cells. In one aspect, the mesenchymal stem cells may be composed only of the narrow-sense stem cells, or they may be a cell population consisting of several types of progenitor cells.

In the present invention, progenitor cells are defined as cells having a unidirectional differentiation potential into cells of a specific tissue other than the blood system, and include cells having a potential to differentiate into a mesenchymal tissue, an epithelial tissue, a nervous tissue, a parenchymal organ, or vascular endothelium.

In the present application, cells whose migration is stimulated by an HMGB1 fragment peptide also include, but are not limited to, bone marrow mesenchymal stem cells and bone marrow-derived mesenchymal stem cells. "Bone marrow mesenchymal stem cells" are cells present in the bone marrow, and are cells characterized in that they are collected from the bone marrow and can be cultured and proliferated as adherent cells on culture dishes (made of plastic or glass) and have the differentiation potential into mesenchymal tissues such as bone, cartilage, adipose, and muscle, as well as nervous and epithelial tissues. In the present application, the term "bone marrow mesenchymal stem cells" is used interchangeably with "bone marrow mesenchymal stromal cells", "bone marrow pluripotent stem cells", and "bone marrow pluripotent stromal cells".

"Bone marrow-derived mesenchymal stem cells" refer to bone marrow mesenchymal stem cells mobilized from the bone marrow to the outside of the bone marrow, and they are cells that can be obtained by peripheral blood sampling and collection from mesenchymal tissues such as fat, epithelial tissues such as skin, and nerve tissues such as brain. In the present application, the term "bone marrow-derived mesenchymal stem cell" is used interchangeably with "bone marrow-derived mesenchymal stromal cell", "bone marrow-derived pluripotent stem cell", and "bone marrow-derived pluripotent stromal cell".

Bone marrow mesenchymal stem cells and bone marrow-derived mesenchymal stem cells are also characterized in that they have a potency to differentiate into epithelial tissues such as keratinocytes that constitute skin and tissues of the nervous system that constitute brain, when administered to a damaged portion of the living body immediately after collection or after once being adhered onto a culture dish.

Bone marrow mesenchymal stem cells and bone marrow-derived mesenchymal stem cells preferably have the potency to differentiate into osteoblasts (identifiable by observing calcification or such when differentiation is induced), chondrocytes (identifiable by positive Alcian blue staining, positive Safranin O staining or such), adipocytes (identifiable by positive Sudan III staining, etc.), as well as mesenchymal cells such as fibroblasts, smooth muscle cells, skeletal muscle cells, stromal cells, and tendon cells, nerve cells, pigment cells, epidermal cells, hair follicle cells (expressing the cytokeratin family, hair keratin family or such), epithelial cells (e.g., epidermal keratinocytes and intestinal epithelial cells express the cytokeratin family or such), endothelial cells, and moreover, cells of parenchymal organs such as liver, kidney, and pancreas. However, the cells after differentiation are not limited to the above-mentioned cells.

Examples of markers for human mesenchymal stem cells include, but are not limited to, all or some of PDGFRα positive, PDGFRβ positive, Lin negative, CD45 negative, CD44 positive, CD90 positive, CD29 positive, Flk-1 negative, CD105 positive, CD73 positive, CD90 positive, CD71 positive, Stro-1 positive, CD106 positive, CD166 positive, CD31 negative, CD271 positive, and CD11b negative.

Examples of markers for murine mesenchymal stem cells include, but are not limited to, all or some of CD44 positive, PDGFRα positive, PDGFRβ positive, CD45 negative, Lin negative, Sca-1 positive, c-kit negative, CD90 positive, CD105 positive, CD29 positive, Flk-1 negative, CD271 positive, and CD11 b negative.

Examples of markers for rat mesenchymal stem cells include, but are not limited to, all or some of PDGFRα positive, CD44 positive, CD54 positive, CD73 positive, CD90 positive, CD105 positive, CD29 positive, CD271 positive, CD31 negative, and CD45 negative.

In the present application, cells whose migration is stimulated by an HMGB1 fragment peptide also include, but are not limited to, PDGFRα-positive cells. Examples of PDGFRα-positive cells whose migration is stimulated by an HMGB1 fragment peptide include, but are not limited to, PDGFRα-positive mesenchymal stem cells, PDGFRα-positive bone marrow-derived mesenchymal stem cells, and PDGFRα-positive bone marrow-derived cells which are obtained as adherent cells by means of cell culture of a monocyte fraction of blood obtained by bone marrow collection (bone marrow cell collection) or peripheral blood collection. Examples of PDGFRα-positive mesenchymal stem cells include cells that are positive for PDGFRα and CD44, cells that are positive for PDGFRα and CD90, cells that are positive for PDGFRα and CD105, cells that are positive for PDGFRα and CD29, and such. In one aspect, the PDGFRα-positive mesenchymal stem cells may be cells that are negative for CD44.

In the pharmaceutical compositions of the present application, peptides that comprise an amino acid sequence with one or more amino acid residues modified (substitutions, deletions, insertions, or additions) in the amino acid sequence described in SEQ ID NO: 1 and have an activity of stimulating cell migration can be used instead of or in conjunction with the HMGB1 fragment peptide comprising the amino acid sequence described in SEQ ID NO: 1. Examples of such peptides include, but are not limited to, the following:

i) a peptide comprising an amino acid sequence in which one or more amino acids (e.g., one to ten, one to nine, one to eight, one to seven, one to six, one to five, one to four, one to three, or one or two) have been substituted, deleted, inserted, or added in the amino acid sequence described in SEQ ID NO: 1, and having an activity of stimulating cell migration;

ii) a peptide consisting of an amino acid sequence in which one or more amino acids (e.g., one to ten, one to nine, one to eight, one to seven, one to six, one to five, one to four, one to three, or one or two) have been substituted, deleted, inserted, or added in the amino acid sequence described in SEQ ID NO: 1, and having an activity of stimulating cell migration;

iii) a peptide comprising an amino acid sequence having about 80% or more, for example, about 85% or more, about 90% or more, about 91% or more, about 92% or more, about 93% or more, about 94% or more, about 95% or more, about 96% or more, about 97% or more, about 98% or more, or about 99% or more sequence identity with the amino acid sequence described in SEQ ID NO:1, and having an activity of stimulating cell migration; and iv) a peptide consisting of an amino acid sequence having about 80% or more, for example, about 85% or more, about 90% or more, about 91% or more, about 92% or more, about 93% or more, about 94% or more, about 95% or more, about 96% or more, about 97% or more, about 98% or more, or about 99% or more sequence identity with the amino acid sequence described in SEQ ID NO:1, and having an activity of stimulating cell migration.

Examples of cells whose migration is stimulated by these peptides include, but are not limited to, mesenchymal stem cells, bone marrow-derived mesenchymal stem cells, PDGFRα-positive cells, PDGFRα-positive mesenchymal stem cells, PDGFRα-positive bone marrow-derived mesenchymal stem cells, and PDGFRα-positive bone marrow-derived cells which are obtained as adherent cells by means of cell culture of a monocyte fraction of blood obtained by bone marrow collection (bone marrow cell collection) or peripheral blood collection.

An effective amount of a peptide of the present application or a pharmaceutical composition comprising the peptide (hereafter referred to as a peptide or such) is administered to a subject for the treatment or prevention of a disease or symptom described herein.

An effective amount as used herein refers to an amount sufficient for the treatment or prevention of a disease or symptom as described herein. Treatment in the present application includes, but is not limited to, alleviation, delay, blockade, improvement, remission, cure, complete cure, and such. Prevention in the present application also includes, but is not limited to, alleviation, delay, blockade, and such.

Subjects in the present application include, without limitation, mammals, birds, fish, and such. Mammals include, but are not limited to, humans and non-human animals, for example, humans, mice, rats, monkeys, pigs, dogs, rabbits, hamsters, guinea pigs, horses, sheep, whales, and such. In the present application, the term "subject" is used interchangeably with "patient", "individual", and "animal".

There is no restriction to the site of administration of a peptide or such of the present application, and the peptides and such of the present application can exert their effects when administered to any site, such as a site with structural or functional abnormality of a tissue or a site nearby, a site different from them (other than those sites), a site distant from a site with structural or functional abnormality of a tissue, a site distal from a site with structural or functional abnormality of a tissue, or a site distal and ectopic to a site with structural or functional abnormality of a tissue.

For example, by administering a peptide or such of the present application at or near a site with structural or functional abnormality of the heart, cells (e.g., mesenchymal stem cells) are recruited to the site of administration to induce or promote regeneration of the cardiac tissue or improvement of structural or functional abnormality of the heart. Also, for example, by administering the peptide or such of the present application to a site different from the site with structural or functional abnormality of the heart or its vicinity, bone marrow cells (e.g., bone marrow mesenchymal stem cells) are mobilized from the bone marrow to a site with structural or functional abnormality of the heart or its vicinity via peripheral circulation to induce or promote regeneration of the cardiac tissue or improvement of structural or functional abnormality of the heart. Here, "peripheral circulation" is also referred to as "blood circulation" and "peripheral circulatory blood flow".

The peptide or such of the present application can also exert its effects when administered to any tissue, such as a tissue different from the cardiac tissue, a tissue distant from the cardiac tissue, a tissue distal from the cardiac tissue, or a tissue distal and ectopic to the cardiac tissue. Thus, the peptide or such of the present application is effectively utilized to regenerate the cardiac tissue, which is difficult to be administered with a drug directly from outside the body, or to ameliorate structural or functional abnormalities of the heart.

Methods of administering the peptide or such of the present application include, but are not limited to, oral administration and parenteral administration including intravascular (intra-arterial, intravenous, and such), intramuscular, subcutaneous, intradermal, intraperitoneal, nasal, pulmonary, and transdermal administrations. Also, the peptide or such of the present application can be administered systemically or locally (e.g., subcutaneously, intradermally, or to the skin surface, eyeball or palpebral conjunctiva, nasal mucosa, oral and gastrointestinal mucosa, vaginal and endometrial mucosa, or injured site) by injection administration, for example, intravenous injection, intramuscular injection, intraperitoneal injection, and subcutaneous injection.

In addition, in place of the peptide or such of the present application, cells secreting the peptides of the present application, gene therapy vectors into which DNAs encoding the peptides have been inserted, and pharmaceutical compositions containing them can be used.

Further, the administration method can be appropriately selected according to the age and symptoms of the patient. When administering the peptides of the present application, for example, the dosage can be selected from the range of 0.0000001 mg to 1000 mg per kilogram of body weight per administration. Alternatively, the dosage can be selected, for example, from the range of 0.00001 to 100000 mg/body per patient. Also when a cell secreting a peptide of the present application or a gene therapy vector into which a DNA encoding the peptide has been inserted is administered, administration can be performed so that the amount of the peptide is within the above range. However, the pharmaceutical compositions in the present application are not limited to these doses.

Pharmaceutical compositions of the present application can be formulated according to conventional methods (e.g., Remington's Pharmaceutical Science, latest edition, Mark Publishing Company, Easton, U.S.A.), and may contain pharmaceutically acceptable carriers and additives together. Examples include, but are not limited to, surfactants, excipients, coloring agents, perfumes, preservatives, stabilizers, buffers, suspending agents, isotonizing agents, binding agents, disintegrants, lubricants, fluidity-promoting agents, and flavoring agents, and other commonly used carriers can be used as appropriate. Specific examples include, light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain fatty acid triglycerides, polyoxyethylene hydrogenated castor oil 60, white sugar, carboxymethyl cellulose, cornstarch, inorganic salts.

All prior art documents cited herein are incorporated herein as references.

The present invention is further illustrated by, but not limited to, the examples below.

EXAMPLES

[Example 1] Efficacy Evaluation of an HMGB1 Fragment Peptide for Dilated Cardiomyopathy (1) Materials and Methods J2N-k hamsters (18-week-old, male, 20 animals in total), which are model animals of dilated cardiomyopathy, were obtained from Japan SLC, acclimated for 2 weeks, and then used for experiments. J2N-k hamsters spontaneously develop dilated cardiomyopathy due to deletion mutations in the δ-sarcoglycan gene (specifically, cardiomyocyte shedding and fibrosis begin around 5 weeks of age, cardiomegaly and cardiac dysfunction appear at approximately 20 weeks of age, and eventually they die of congestive heart failure at approximately 1 year. J Biochem. 2003 August; 134(2):269-76). Also, a peptide consisting of amino acid residues 1-44 (SEQ ID NO: 1) of the human HMGB1 protein was chemically synthesized by a solid-phase method. Hereinafter, the peptide is referred to as the HMGB1 peptide (1-44), and is abbreviated as "1-44" in the drawing corresponding to the Examples.

J2N-k hamsters were divided into the HMGB1 peptide (1-44)-treated (n=10) and PBS-treated (control, n=10) groups, and treatment was begun at 20 weeks of age (body weight about 120 g). Administration of the test substance was carried out by injecting a solution of the HMGB1 peptide (1-44), which has been adjusted to a concentration of 1 mg/ml with PBS as the vehicle, into the external jugular vein at a dose of 3 ml/kg (3 mg/kg as the peptide dosage) once a day for four consecutive days. In the control group, PBS was injected into the external jugular vein at a dose of 3 ml/kg once a day for four consecutive days. At 6 weeks after administration, a thoracotomy was performed under deep anesthesia, and the heart was removed. The mid portion of the heart was divided for cryopreservation and for paraffin fixation, and a histopathological examination was performed. Molecular biological studies were also performed using apical myocardium to evaluate effects of administration of the HMGB1 peptide (1-44).

(2) Items for Evaluation i) Cardiac Function

Echocardiography was performed prior to dosing, and at 4 and 6 weeks after dosing; and left ventricular end-diastolic diameter (LVDd), left ventricular end-systolic diameter (LVDs), and left ventricular ejection fraction (LVEF) were measured and calculated to perform a cardiac function assessment.

ii) Myocardial Fibrosis

Myocardial tissue sections were stained with Sirius red, and the proportion of stain-positive area in the entire myocardial area was calculated as the percentage of fibrosis (%).

iii) Angiogenesis

Immunostaining of the myocardial tissue sections was performed using an anti-CD31 antibody to determine the number of blood vessels (number of vascular endothelial cells). This measurement was performed in five different fields and the mean value was calculated.

iv) Hypertrophy of Cardiomyocytes

Periodic Acid Schiff (PAS) staining of the myocardial tissue sections was performed to measure the short diameter of cardiomyocytes retaining a nuclear architecture, and the average of the measurements was obtained. This measurement was performed in five different fields and the mean value was calculated.

v) Recruitment of Mesenchymal Stem Cells

Immunostaining of the myocardial tissue sections was performed using antibodies against PDGFRα and CD29, which are surface markers of mesenchymal stem cells, to assess whether accumulation of mesenchymal stem cells was observed. Staining of the nuclei was performed using DAPI.

vi) RT-PCR

The intramyocardial expression of VEGF, an angiogenic factor secreted by mesenchymal myeloid stem cells, and that of TSG-6, an anti-inflammatory cytokine, were assessed by RT-PCR using apical myocardium.

vii) Mitochondrial Structure

The structure of cardiomyocytes was observed by electron microscopy. Specifically, the full-thickness myocardium of the mid-portion was sampled, and subjected to pre-fixation with ½ Karnofsky, post-fixation with 2% osmium tetroxide, block-staining with 0.5% uranium acetate aqueous solution and dehydration with ethanol, and then embedded and polymerized by infiltrating epoxy resin (Queto1812). Ultra-thin sections (70-110 nm) were made, and electron staining with uranium acetate and a lead stain solution was performed, and then observed by electron microscopy (H-7500, Hitachi High Technologies).

(3) Results i) Cardiac Function

Cardiac function assessments at 4 and 6 weeks after dosing showed significantly higher levels of LVEF in the HMGB1 peptide (1-44) group compared with the PBS group, and reduction in the left ventricular contractility was inhibited (FIG. 1). These results indicate the improving effect of HMGB1 peptide (1-44) on the cardiac function. There were no significant differences in LVDd and LVDs at any time point after 4 and 6 weeks of dosing.

ii) Myocardial Fibrosis

Figure 2:
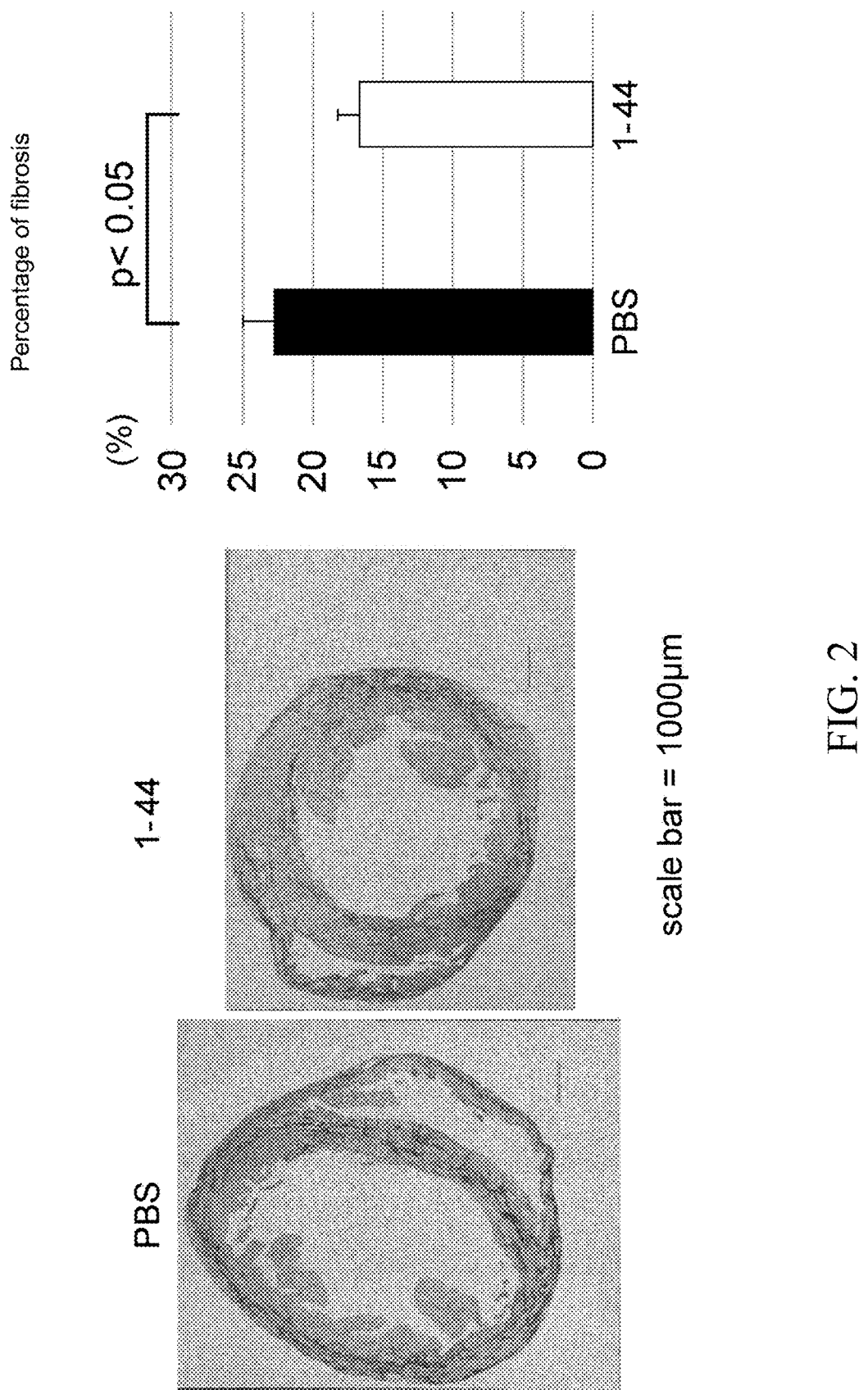
FIG. 2 is a photograph showing the result of Sirius red staining of myocardial tissue sections and a graph showing the percentage of positively stained area.

Analysis showed that the percentage of Sirius red stain-positive area was significantly smaller in the HMGB1 peptide (1-44) group than in the PBS group, indicating that myocardial fibrosis was inhibited (FIG. 2).

iii) Angiogenesis

Figure 3:
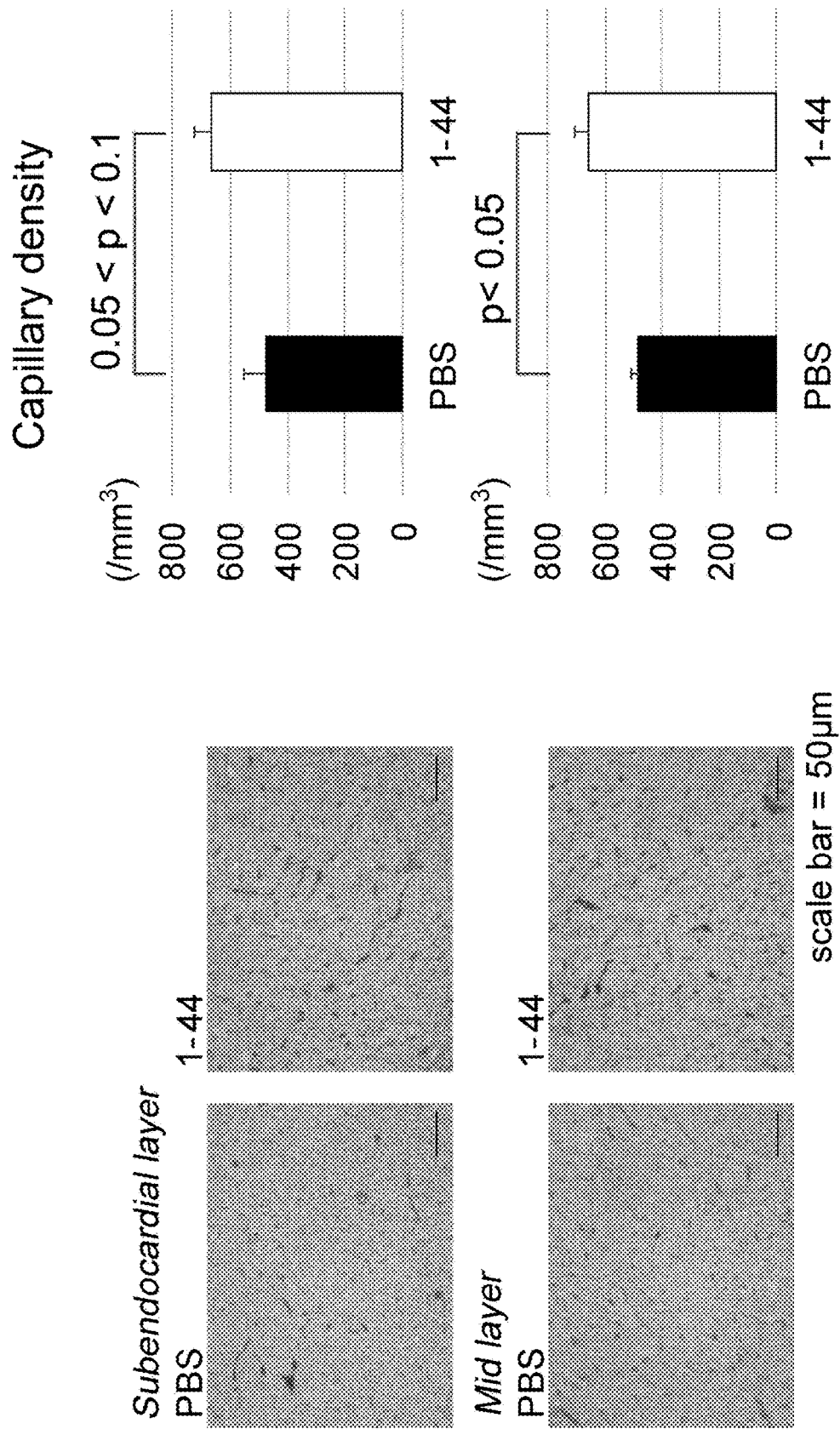
FIG. 3 is a photograph showing the result of immunostaining (anti-CD31 antibody) of myocardial tissue sections and a graph showing capillary density.

Immunostaining results showed that in the mid layer, the HMGB1 peptide (1-44) group had a significantly higher number of blood vessels and enhanced angiogenesis than the PBS group (FIG. 3). In the subendocardial layer also, the number of blood vessels tended to be higher in the HMGB1 peptide (1-44) group than in the PBS group.

iv) Hypertrophy of Cardiomyocytes

Figure 4:
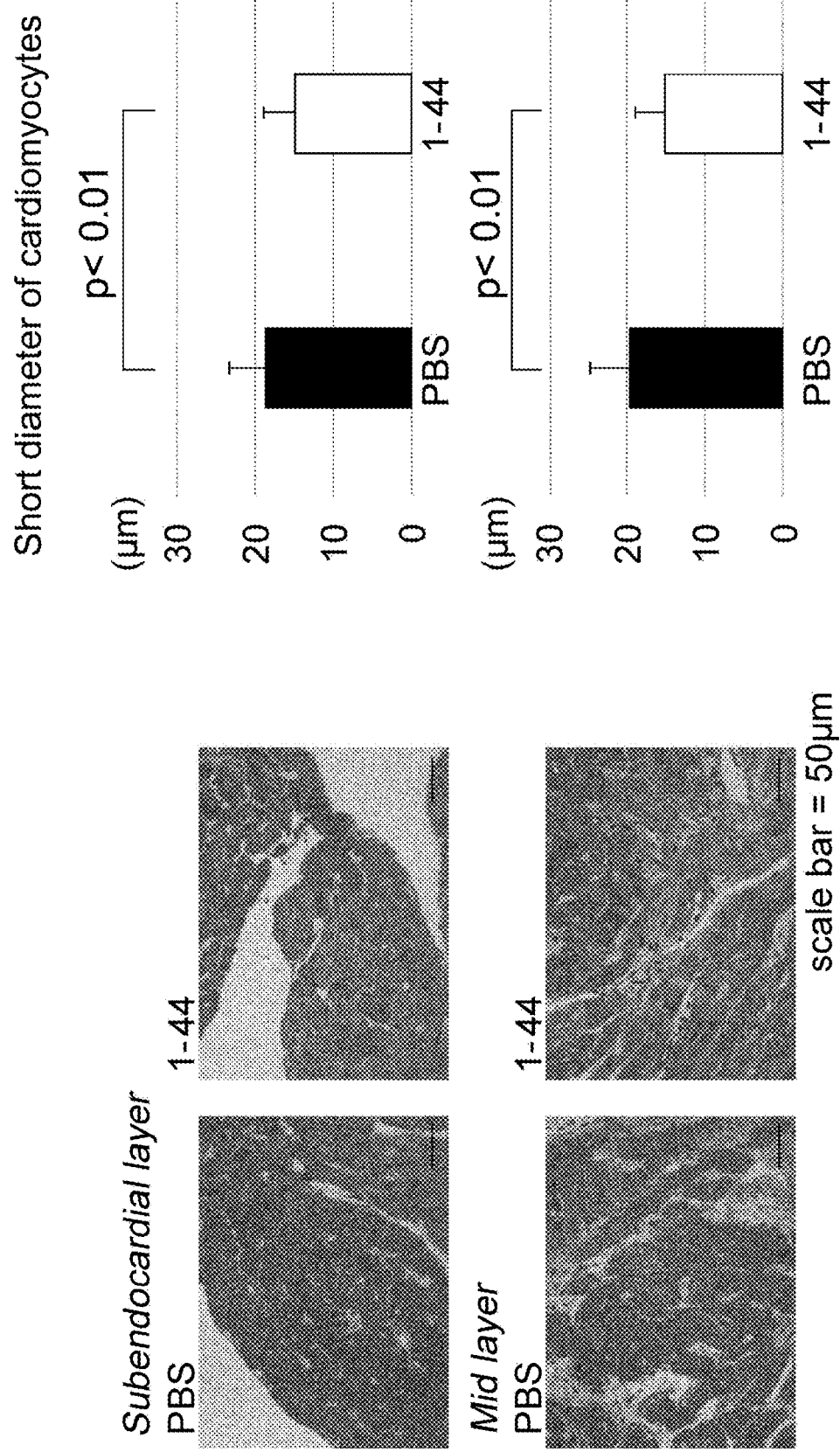
FIG. 4 is a photograph showing the result of PAS staining of myocardial tissue sections and a graph showing the short diameter of cardiomyocytes.

PAS-staining results showed that the short diameter of cardiomyocytes was significantly smaller in the HMGB1 peptide (1-44) group than in the PBS group in both the subendocardial layer and mid layer, indicating that hypertrophy of the cardiomyocytes was inhibited (FIG. 4).

v) Recruitment of Mesenchymal Stem Cells

Figure 5:
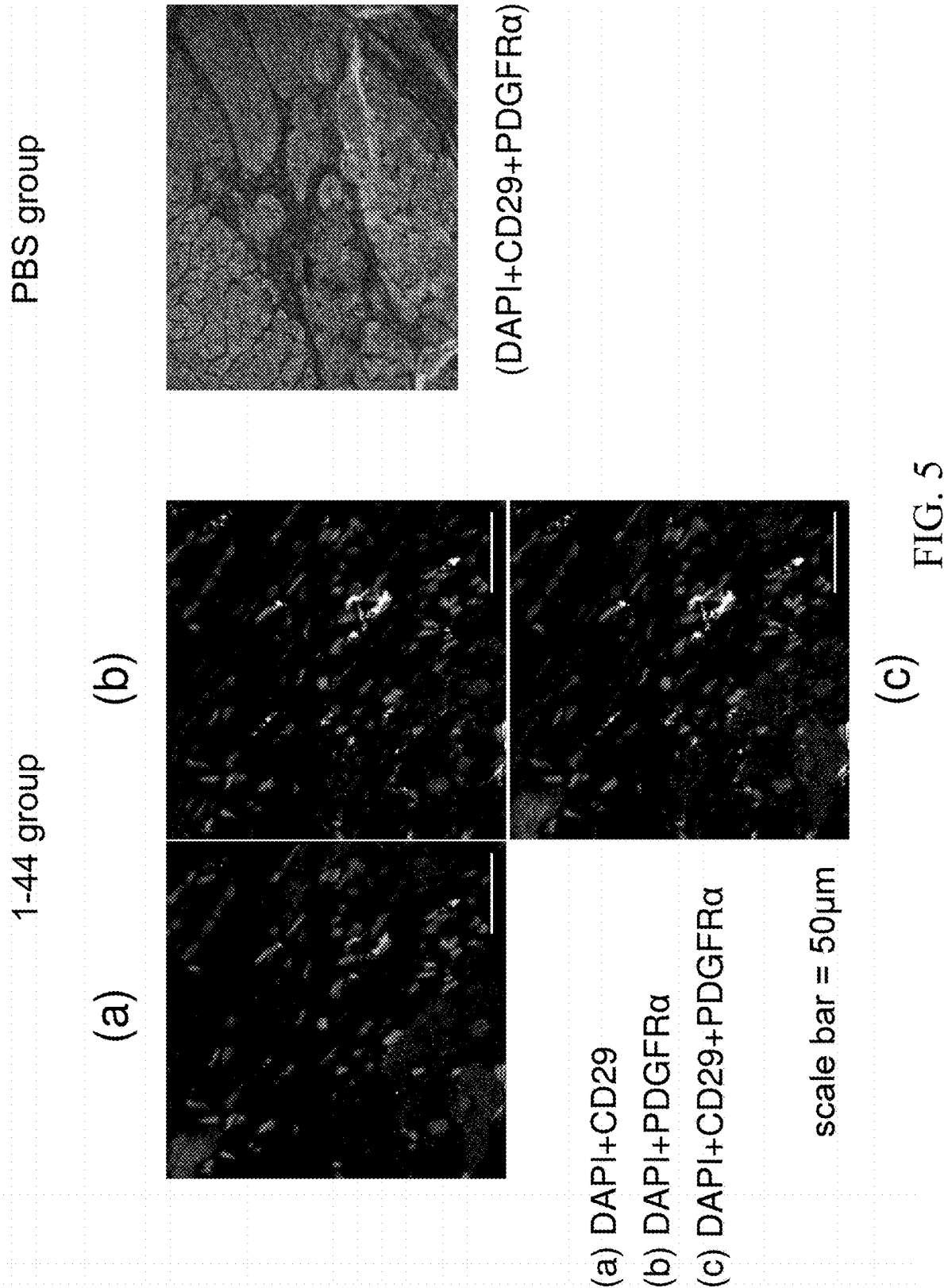
FIG. 5 is a photograph showing the result of immunostaining using antibodies against PDGFRα and CD29. PDGFRα, green; CD29, red; DAPI, blue.
Figure 6:
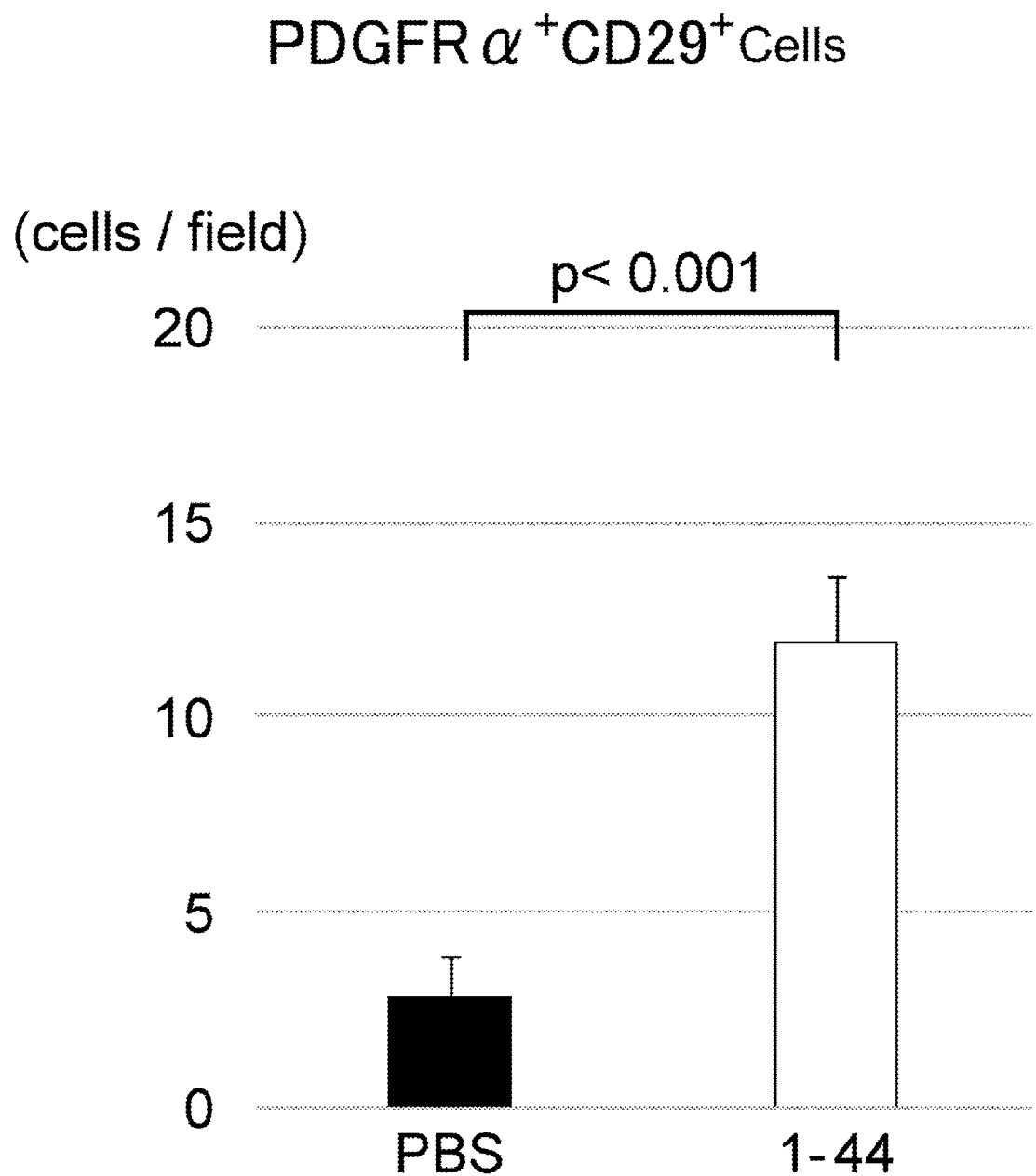
FIG. 6 is a graphical representation of the number of PDGFRα-positive and CD29-positive cells in the HMGB1 peptide (1-44) and PBS groups.

Immunostaining revealed that cells positive for both PDGFRα and CD29 were recruited to the myocardial tissue of the HMGB1 peptide (1-44) group (FIG. 5). Also, significantly more PDGFRα-positive and CD29-positive cells were present in the myocardial tissue of the HMGB1 peptide (1-44) group than in the PBS group (FIG. 6).

vi) RT-PCR

Figure 7:
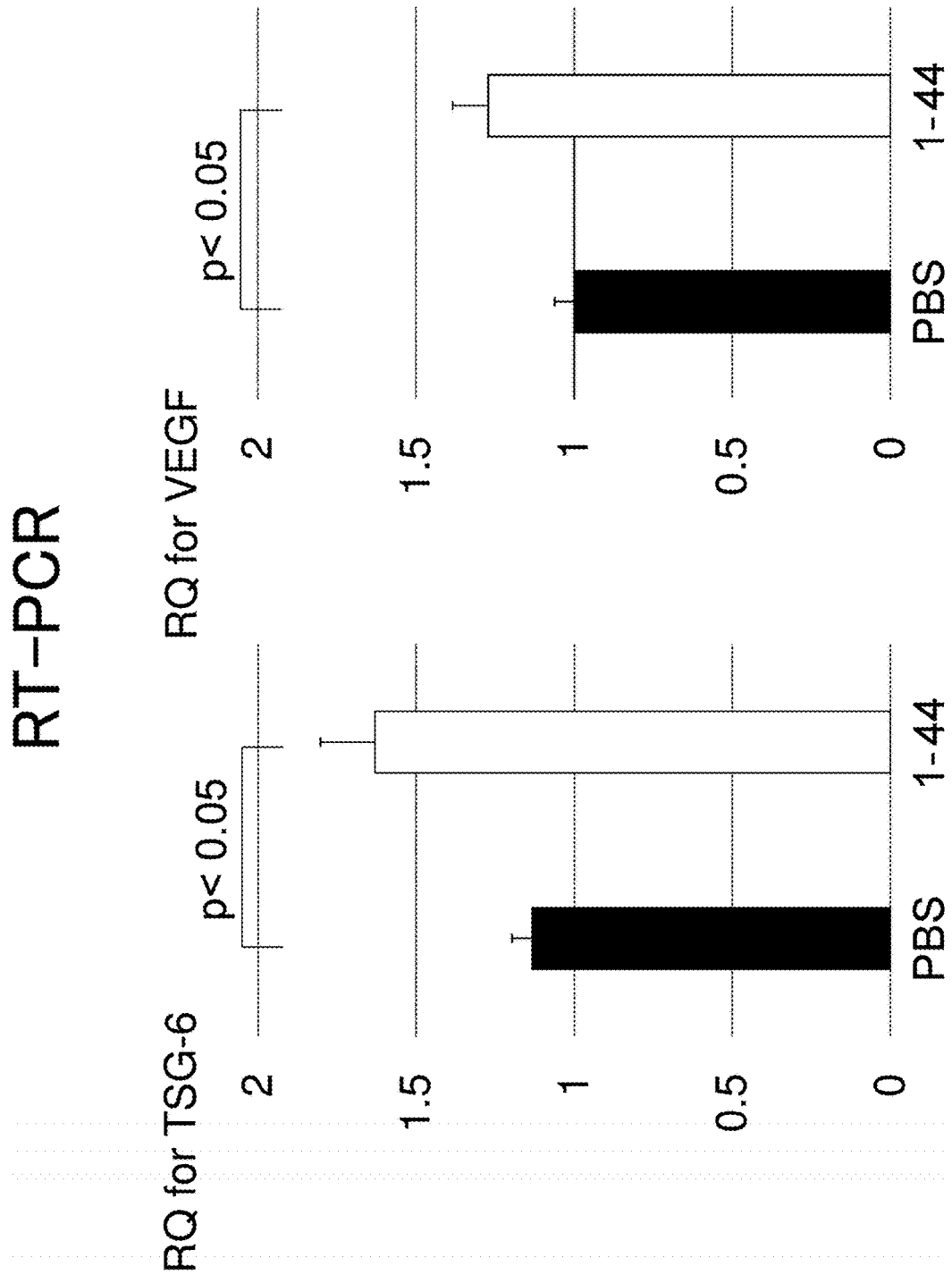
FIG. 7 is a graphical representation of the expression levels of VEGF and TSG-6 analyzed by RT-PCR. RQ, relative quantity.

Analysis showed that both VEGF and TSG-6 had significantly higher expression levels in the HMGB1 peptide (1-44) group than in the PBS group (FIG. 7).

vii) Mitochondrial Structure

Figure 8:
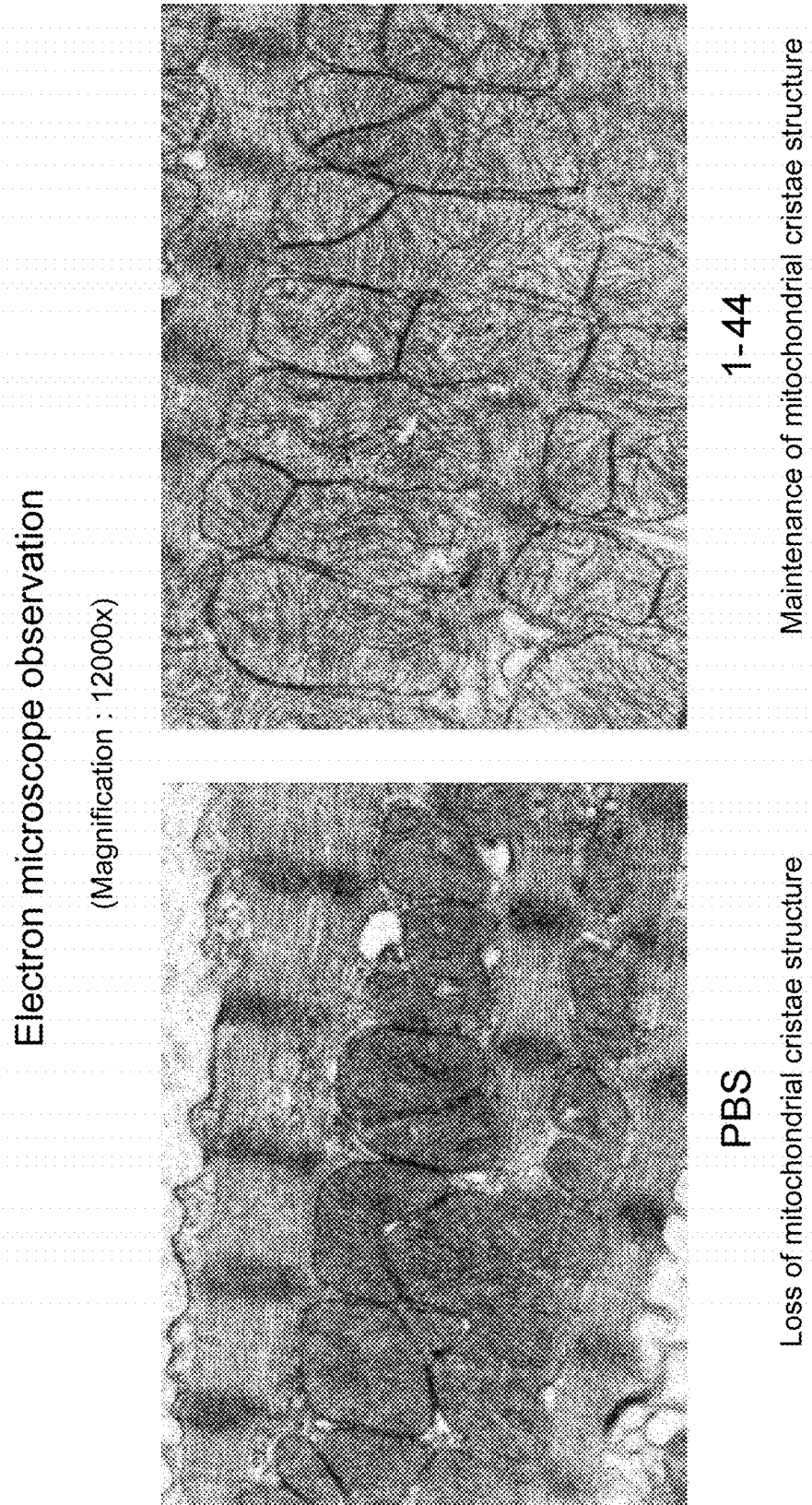
FIG. 8 is a photograph showing an observation result of cardiomyocytes by electron microscope.

Electron microscopic examination of cardiomyocytes revealed loss of the mitochondrial cristae structure in the PBS group, whereas the cristae structure was maintained in the HMGB1 peptide (1-44) group (FIG. 8). These results support the effect of the HMGB1 peptide (1-44) administration in maintaining the cardiac function.

[Example 2] Efficacy Evaluation of the HMGB1 Fragment Peptide for Dilated Cardiomyopathy (Long-Term Observations)

(1) Materials and Methods

As in Example 1, twenty J2N-k hamsters were prepared and divided into the HMGB1 peptide (1-44)-treated group (n=11) and the PBS-treated group (control, n=9), and treatment was begun at 20 weeks of age. Administration of the test substance was carried out by injecting a solution of the HMGB1 peptide (1-44), which has been adjusted to a concentration of 1 mg/ml with PBS as the vehicle, into the external jugular vein at a dose of 3 ml/kg (3 mg/kg as the peptide dosage) once daily for four consecutive days. In the control group, PBS was injected into the external jugular vein at a dose of 3 ml/kg once a day for four consecutive days. Evaluation of the cardiac function and survival rate was continued thereafter while rearing the hamsters under normal conditions.

(2) Items for Evaluation i) Cardiac Function

Echocardiography was performed prior to dosing, at 4 weeks after dosing, and every 2 weeks thereafter to measure LVEF.

ii) Survival Rate

After the last dose, the animals were kept under normal conditions and the survival rate was evaluated.

(3) Results i) Cardiac Function

Figure 9:
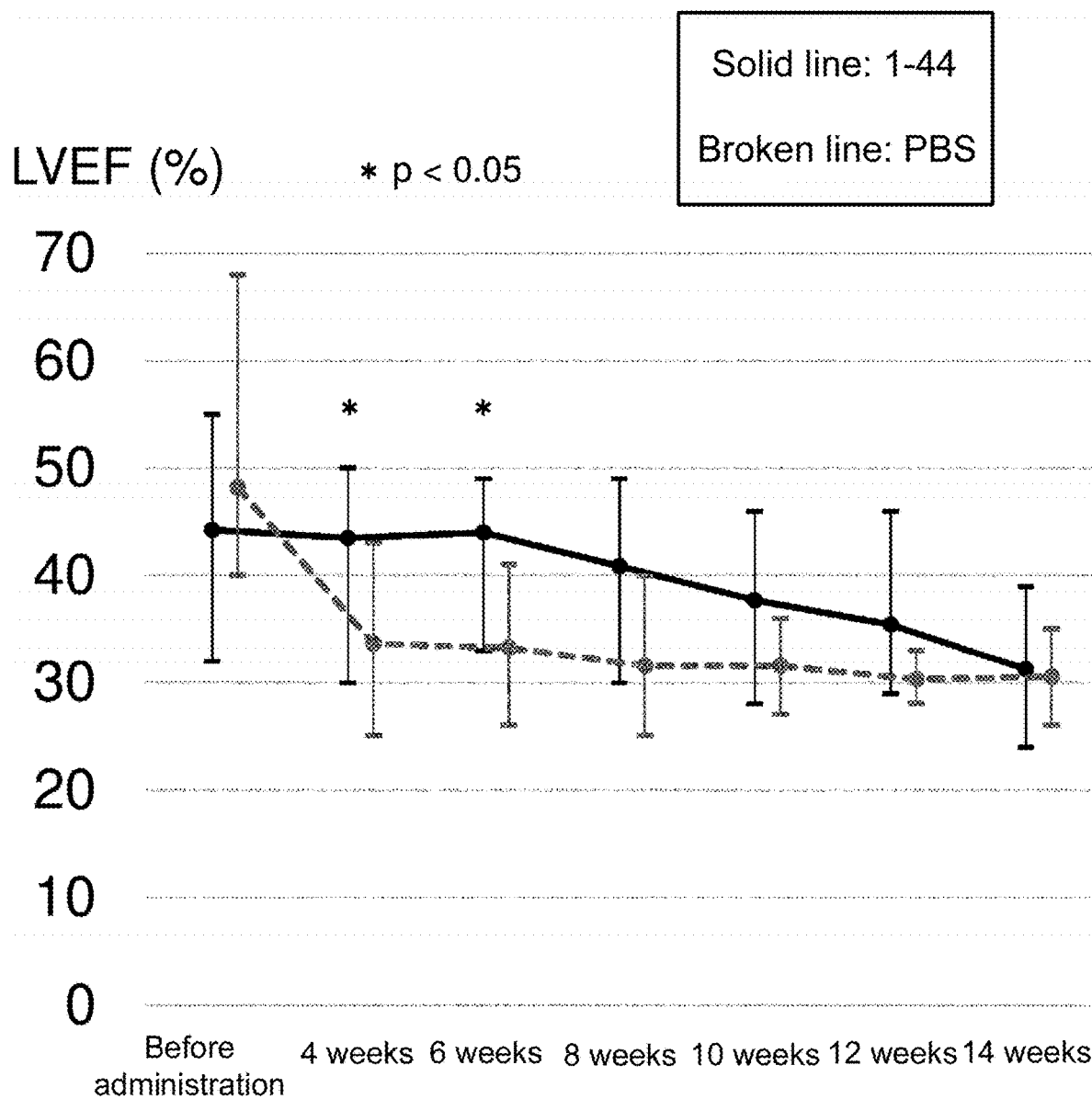
FIG. 9 presents graphs showing the results of the left ventricular ejection fraction (LVEF) measurement from pre-dose to 14 weeks post-dose in the HMGB1 peptide (1-44) group and PBS group.

The LVEF of the HMGB1 peptide (1-44) group remained significantly higher than that of the PBS group until 6 weeks after administration (FIG. 9).

ii) Survival Rate

Figure 10:
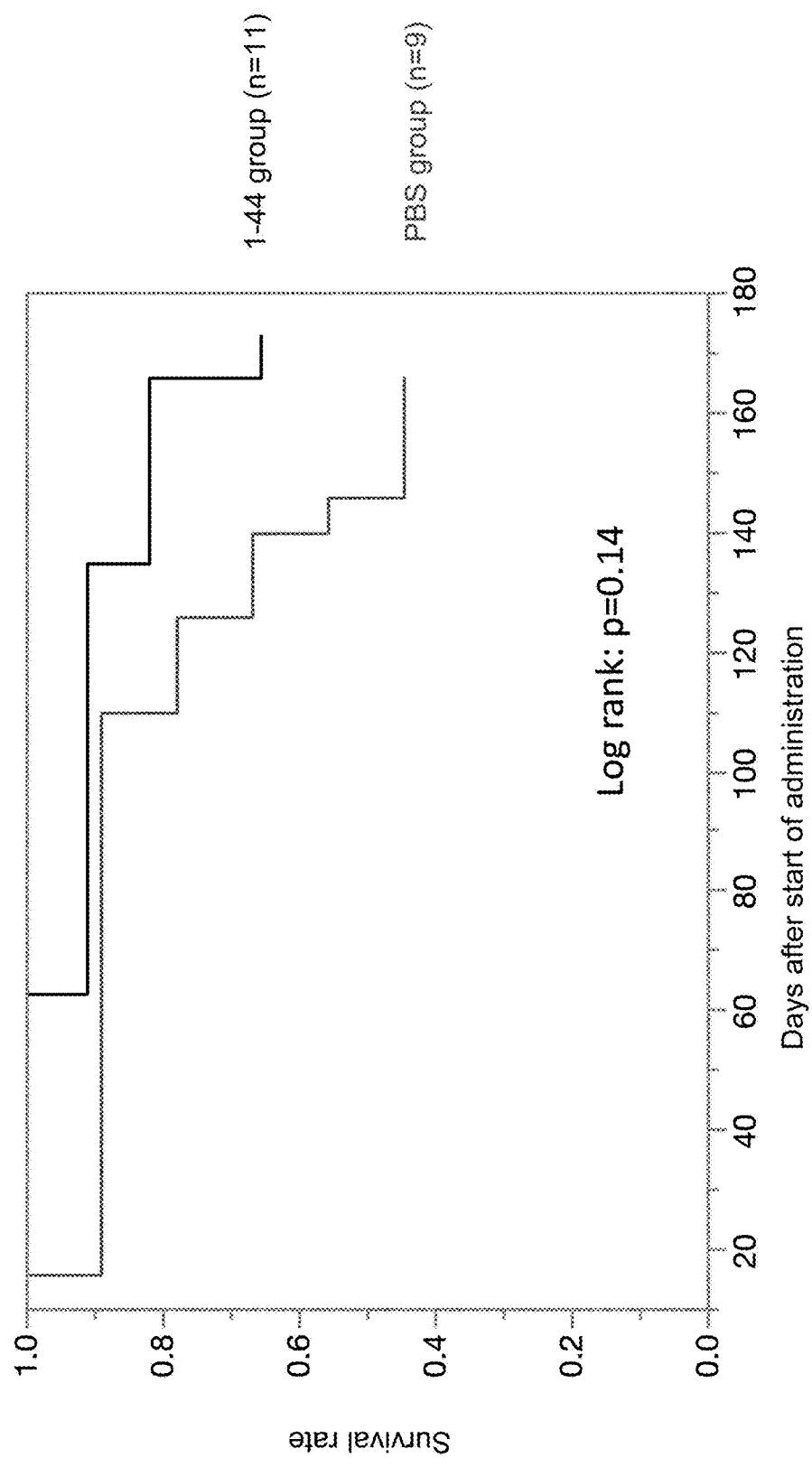
FIG. 10 is a graphical representation of the viability of the HMGB1 peptide (1-44) group and the PBS group.

Long-term observations showed a tendency toward higher viability in the HMGB1 peptide (1-44) group (FIG. 10).

[Example 3] Efficacy Evaluation of the HMGB1 Fragment Peptide on Improving the Cardiac Function after Old Myocardial Infarction (1) Materials and Methods SD rats (7-week-old, male, body weight of approximately 250 g) were anesthetized with the inhalation anesthetic sevofrane (or isoflurane) and intubated endotracheally after adequate suppression was achieved, and deep anesthesia was maintained with the inhalation anesthetic. A thoracotomy was performed in the supine position at the left fourth intercostal space, and the proximal portion of the left anterior descending coronary artery was ligated with 6-0 prolene sutures to create a broad-area myocardial infarction model. The cardiac function was evaluated by echocardiography 2 weeks after the infarction was made, and cases in which extensive infarction was obtained (LVEF<50%) were used as old myocardial infarction model rats (17 animals in total). Similar to the above examples, the HMGB1 peptide (1-44) consisting of SEQ ID NO: 1 was used.

The old myocardial infarction model rats were divided into the HMGB1 peptide (1-44)-treated group (n=9) and the PBS-treated group (control, n=8), and treatment was begun 2 weeks after the infarction was made. Administration of the test substance was carried out by injecting a solution of the HMGB1 peptide (1-44), which has been adjusted to a concentration of 1 mg/ml with PBS as vehicle, into the femoral veins at a dose of 3 ml/kg (3 mg/kg as the peptide dosage) once daily for four consecutive days. In the control group, PBS was injected at a dose of 3 ml/kg once a day via the femoral vein for four consecutive days. At 4 weeks after dosing, the heart was removed by re-thoracotomy under deep anesthesia. At the time of removal, 5 ml or more blood was collected by puncture from the right atrium toward the inferior vena cava, and the infarction area of heart was cut into four short-axis slices of equal thickness and divided for cryopreservation and paraffin fixation. Both groups were comparatively studied using cardiac physiological, histopathological, and molecular biological techniques to evaluate the effects of administering the HMGB1 peptide (1-44). The condition after 2 weeks (14 days) or more have passed following the onset of myocardial infarction in model rats is equivalent to the condition after 30 days or more have passed following the onset of myocardial infarction in humans. In addition, the old myocardial infarction model rats prepared in this study can be regarded as a model of ischemic cardiomyopathy because the LVEF was decreased to 42% at the time point prior to dosing, and the progression of cardiomegaly was observed in the control group.

(2) Items for Evaluation i) Cardiac Function

Echocardiography was performed at 1, 2, and 4 weeks after dosing, and the left ventricular end-diastolic diameter (LVDd), left ventricular end-systolic diameter (LVDs), and left ventricular ejection fraction (LVEF) were measured and calculated to perform a cardiac function assessment.

ii) Myocardial Fibrosis

Myocardial tissue sections were stained with Sirius red, and the proportion of stain-positive area in the total area of the left ventricular myocardium was calculated as the percentage of fibrosis (%).

iii) Angiogenesis

Von-Willebrand factors were stained at the infarct border to determine the number of blood vessels (number of vascular endothelial cells). This measurement was performed in 10 different fields and the mean value was calculated.

iv) Hypertrophy of Cardiomyocytes

Periodic Acid Schiff (PAS) staining was performed at the infarct border, and the short diameter of cardiomyocytes retaining a nuclear architecture at the infarct border was measured, and the average of the measurements was obtained. This measurement was performed in 10 different fields and the mean value was calculated.

v) Recruitment of Mesenchymal Stem Cells at the Infarct Boundary

Immunostaining of the myocardial tissue was performed using antibodies against PDGFRα, CD90, and CD105, which are surface markers of mesenchymal stem cells, to evaluate whether accumulation of mesenchymal stem cells was observed at the infarct border. Staining of the nuclei was performed using DAPI.

(3) Results i) Cardiac Function

Figure 11:
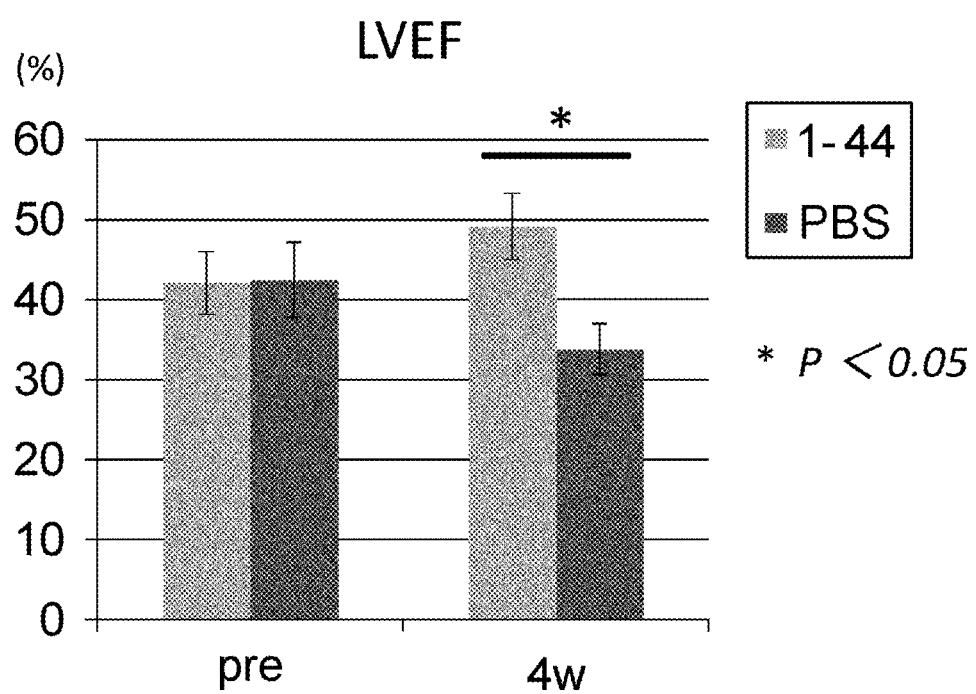
FIG. 11 presents a graph showing the results of the left ventricular ejection fraction (LVEF) measurement in the HMGB1 peptide (1-44) group and the PBS group before and 4 weeks after administration.
Figure 12:
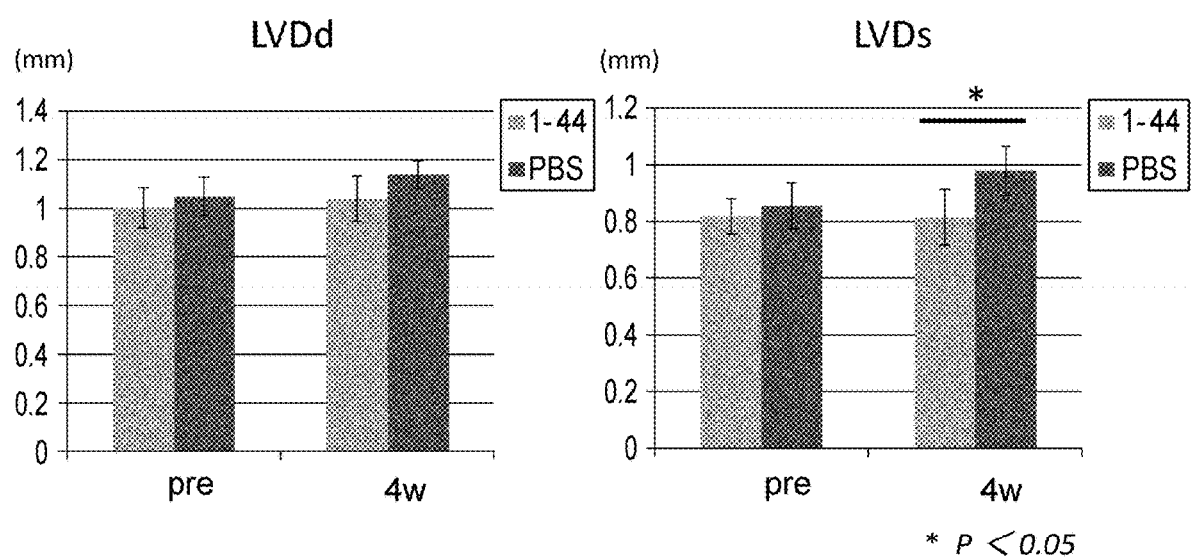
FIG. 12 presents graphs showing the results of measurement of the left ventricular end-diastolic diameter (LVDd) and left ventricular end-systolic diameter (LVDs) in the HMGB1 peptide (1-44) group and the PBS group before and 4 weeks after administration.

Cardiac function assessment at 4 weeks after dosing showed significantly higher levels of LVEF in the HMGB1 peptide (1-44) group compared to the PBS group (FIG. 11). In addition, LVDd and LVDs at 4 weeks after dosing showed smaller values in the HMGB1 peptide (1-44) group than in the PBS group, and inhibition of cardiomegaly was observed (FIG. 12).

Figure 13:
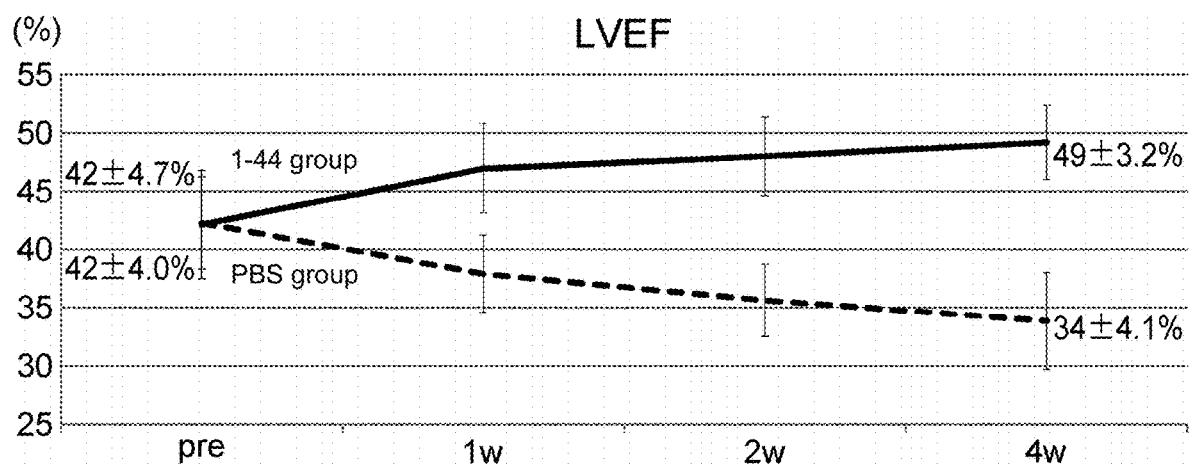
FIG. 13 presents a graph showing the results of the left ventricular ejection fraction (LVEF) measurement from pre-dose to 4 weeks post-dose in the HMGB1 peptide (1-44) and PBS groups.

In addition, with respect to the change in LVEF over time, the PBS group showed a decrease in LVEF over time after dosing, whereas the HMGB1 peptide (1-44) group showed an increase in LVEF over time up to 4 weeks after dosing, with an average improvement in LVEF of about 7% with respect to before the dosing (FIG. 13).

ii) Myocardial Fibrosis

Figure 14:
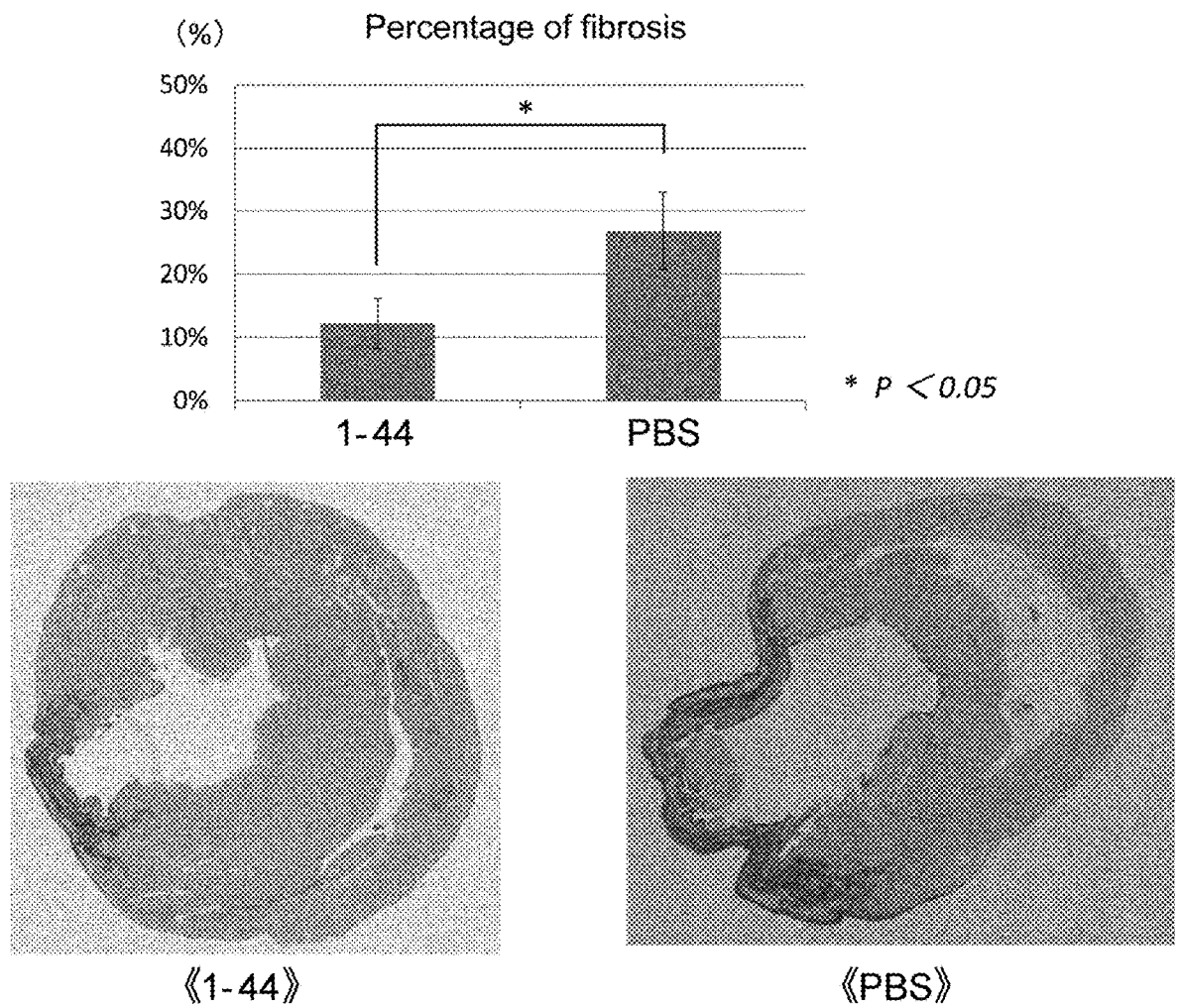
FIG. 14 is a photograph showing the result of Sirius red staining of myocardial tissue sections and a graph showing the percentage of positively stained area.

Analysis showed that the percentage of Sirius red stain-positive area was significantly smaller in the HMGB1 peptide (1-44) group than in the PBS group, indicating that myocardial fibrosis was inhibited (FIG. 14).

iii) Angiogenesis

Figure 15:
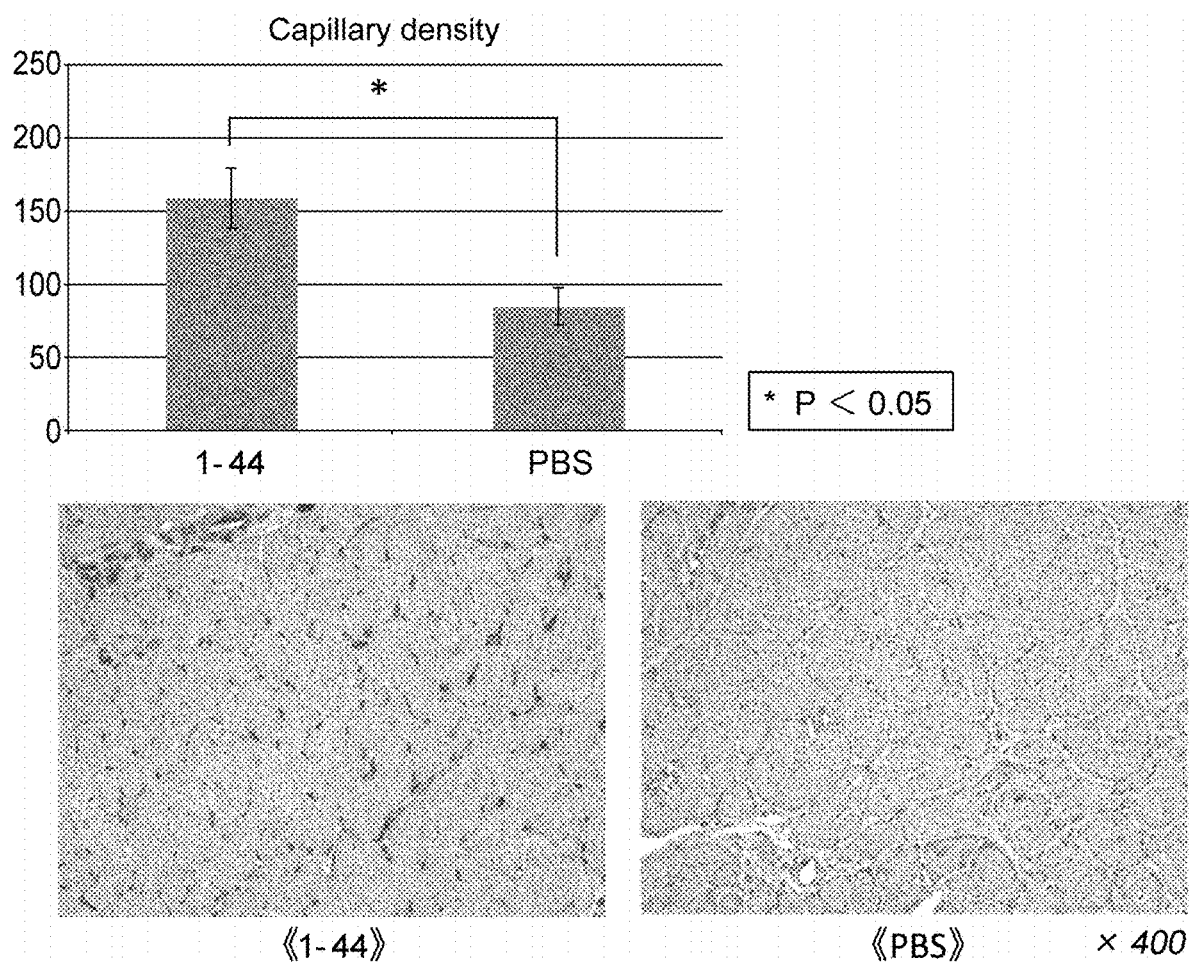
FIG. 15 presents a graph showing capillary density at the infarct border and a photograph showing the result of von-Willebrand factor staining at the infarct border.

Von-Willebrand factor-staining results at the infarct border showed that the HMGB1 peptide (1-44) group had significantly more vessels than the PBS group (P=0.05) indicating that angiogenesis was enhanced (FIG. 15).

iv) Hypertrophy of Cardiomyocytes

Figure 16:
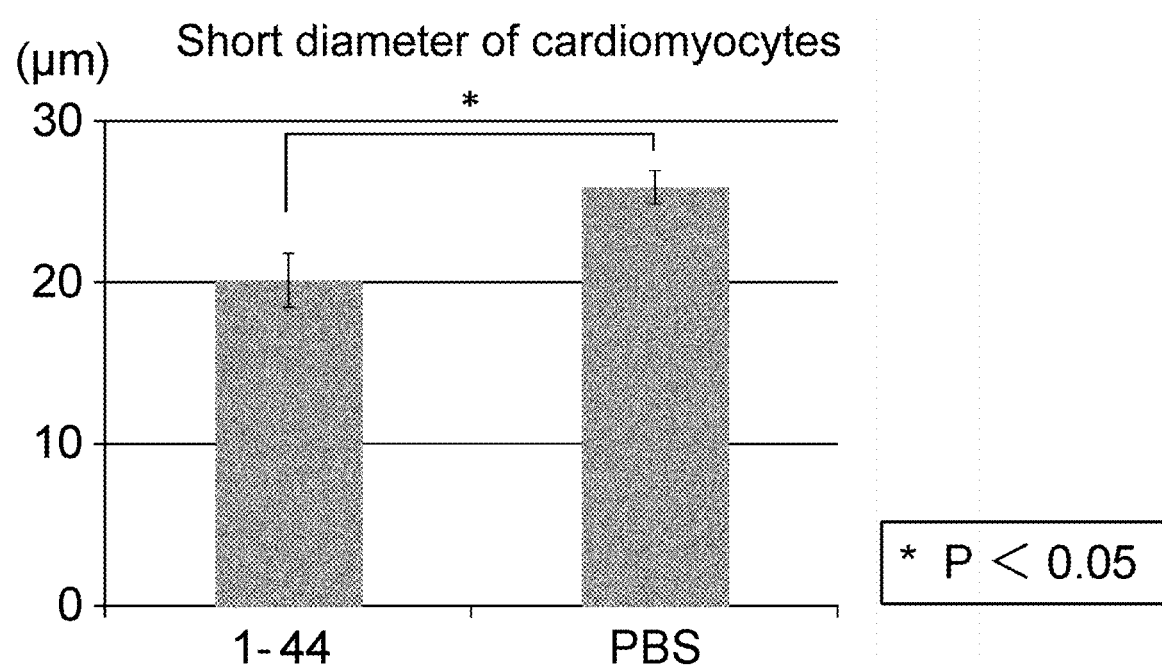
FIG. 16 presents a graph showing the short diameter of cardiomyocytes at the infarct border.

The results of PAS staining at the infarct border showed that the short diameter of cardiomyocytes was significantly smaller in the HMGB1 peptide (1-44) group than in the PBS group (P=0.05), indicating that the hypertrophy of cardiomyocytes was inhibited (FIG. 16).

v) Recruitment of Mesenchymal Stem Cells at the Infarct Border

Figure 17:
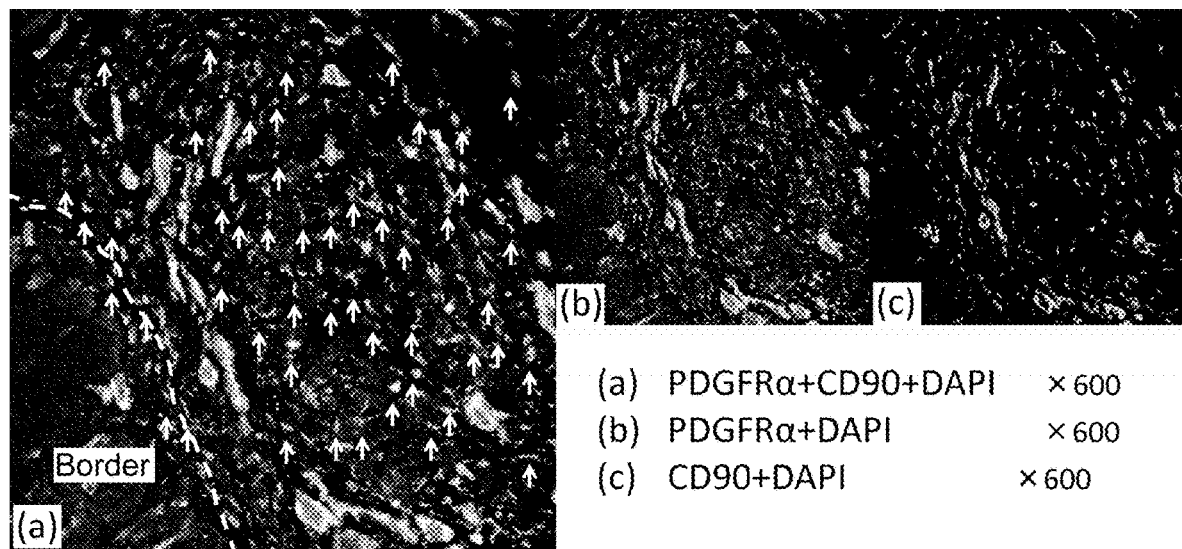
FIG. 17 is a fluorescent immunostaining image of the infarct border in the HMGB1 peptide (1-44) group. PDGFRα, green; CD90, red; DAPI, blue. The arrows in (a) indicate the PDGFRα- and CD90-double positive cells, and the broken line indicates the infarct border.
Figure 18:
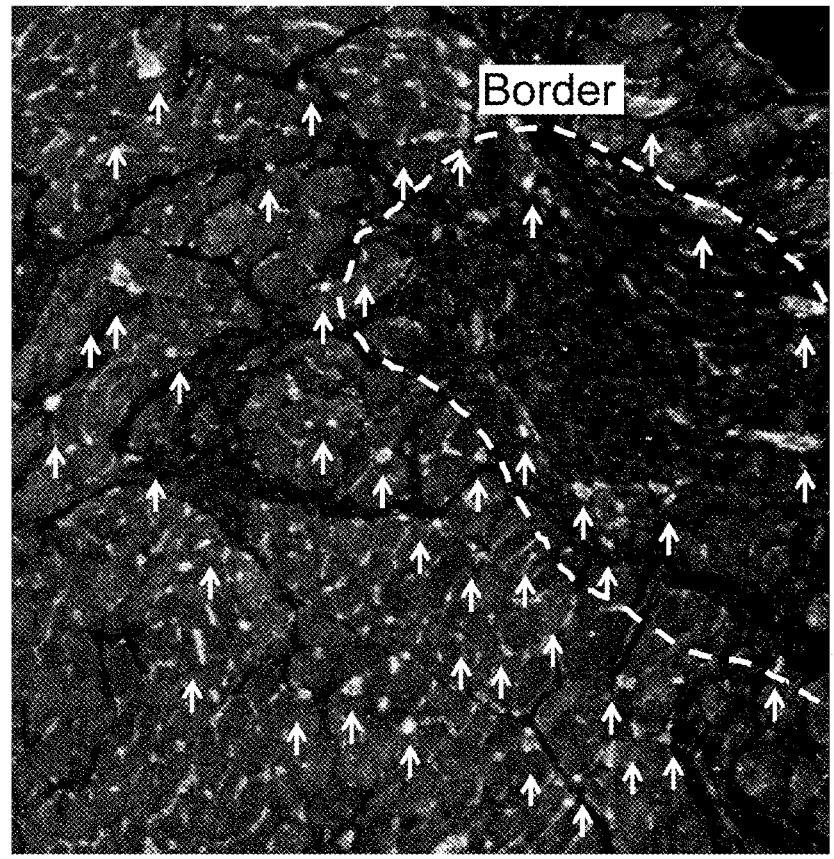
FIG. 18 is a fluorescent immunostaining image of the infarct border in the HMGB1 peptide (1-44) group. PDGFRα, green; CD105, red; DAPI, blue. The arrows indicate the PDGFRα- and CD105-double positive cells, and the broken line indicates the infarct border.
Figure 19:
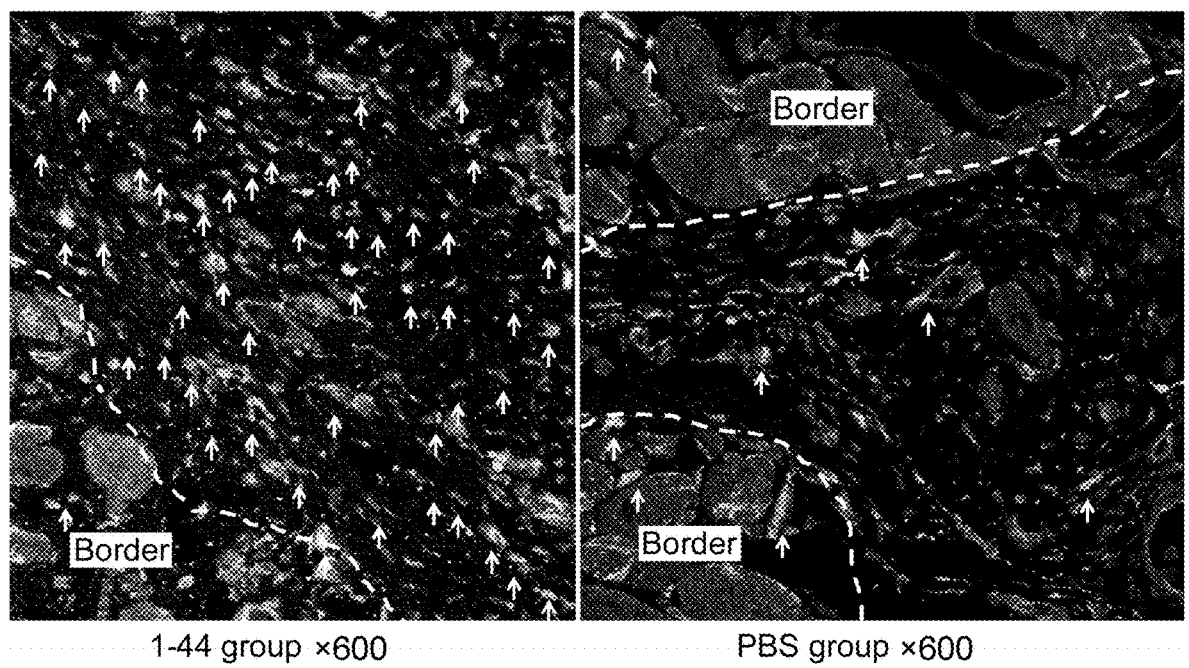
FIG. 19 is a fluorescent immunostaining image of the infarct border in the HMGB1 peptide (1-44) group and the PBS group. PDGFRα, green; CD90, red; DAPI, blue. The arrows indicate the PDGFRα- and CD90-double positive cells, and the broken line indicates the infarct border.

Immunostaining of the myocardial tissue revealed that cells positive for both PDGFRα and CD90 and cells positive for both PDGFRα and CD105 were recruited near the infarct border of the HMGB1 peptide (1-44) group (FIGS. 17 and 18). There were also more PDGFRα-positive and CD90-positive cells in the vicinity of the infarct border in the HMGB1 peptide (1-44) group than in the PBS group (FIG. 19).

[Example 4] Efficacy Evaluation of the HMGB1 Fragment Peptide for Hypertensive Cardiomyopathy (1) Materials and Methods The Dahl salt-sensitive rats (hereafter also referred to as DIS/Eis rats) were used in the experiments. DIS/Eis rats are hypertensive when fed with a high-salt diet and are a model that develop heart failure at a high incidence (e.g., when fed with a diet supplemented with 8% NaCl from 6 weeks of age, blood pressure reaches 250 mm Hg at 9 weeks of age, death begin to appear from 12 weeks of age, and death is highly probable by 16 weeks of age).

Ten DIS/Eis rats (6-weeks-old, male, body weight about 200 g, Japan SLC) were prepared and divided into two groups, a high-salinity diet group (n=7) and a low-salinity diet group (n=3), and feeding was continued until 15 weeks of age in which the former was fed with a diet supplemented with 8% NaCl and the latter was fed with a diet supplemented with 0.3% NaCl. Aside from the meals, nothing interfered with free movement and they were kept clean and rested without restriction on drinking water, feeding, and such in their cages.

At 11 weeks of age, the high-salinity diet group (n=7) was divided into the HMGB1 peptide (1-44)-treated group (n=3) and the control group (n=4), and treatment was initiated. Administration of the test substance was carried out by injecting a solution of the HMGB1 peptide (1-44), which has been adjusted to a concentration of 1 mg/ml with PBS as the vehicle, into the tail vein at a dose of 3 ml/kg (3 mg/kg as the peptide dosage) once daily for four consecutive days. The control group was injected with PBS at a dose of 3 ml/kg once a day via the tail vein for four consecutive days. Similar to the control group, the low-salinity diet group (n=3) also received PBS via the tail vein for four consecutive days. At 4 weeks after dosing (at 15 weeks, of age), hearts were removed from the rats by thoracotomy under general anesthesia, and their weight was measured, and then histological sections of the left ventricular myocardial cross sections were prepared at the papillary muscle level and subjected to histological analysis. In the following description, the HMGB1 peptide (1-44) administration group fed with a high-salinity diet is abbreviated as the "High-1-44 group"; the control group fed with a high-salinity diet is abbreviated as the "High-PBS group" and the low-salinity diet group is abbreviated as the "Low-PBS group".

(2) Items for Evaluation i) Heart Weight

At 15 weeks of age, hearts were removed from rats in each group and weighed.

ii) Cardiac Function and Ventricular Wall Thickness

Echocardiography was performed prior to dosing and every week after initiation of dosing to determine the left ventricular end diastolic diameter (LVDd), left ventricular end systolic diameter (LVDs), left ventricular ejection fraction (LVEF), end-diastolic left ventricular anterior wall thickness (LVAWd), and end-diastolic left ventricular posterior wall thickness (LVPWd).

iii) Myocardial Fibrosis

Myocardial tissue sections were stained with Sirius red, and the proportion of stain-positive area in the area of the whole heart or the left ventricle was calculated as the percentage of fibrosis (%).

(3) Results i) Heart Weight

Figure 20:
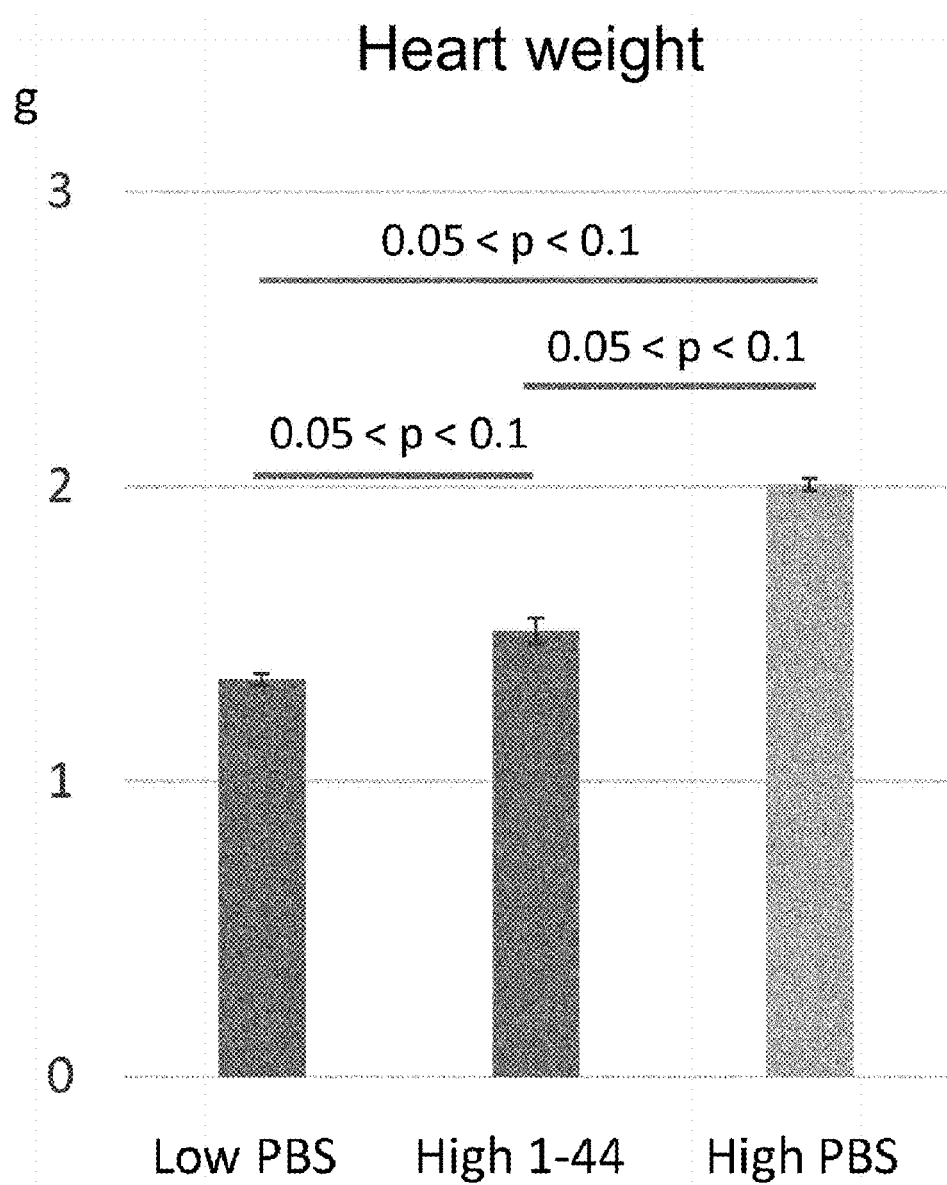
FIG. 20 presents a graph showing heart weight at 15 weeks of age.

Compared with the Low-PBS group, the High-1-44 and High-PBS groups had greater heart weights. Further, the High-1-44 group had smaller heart weights than the High-PBS group, indicating that administration of the HMGB1 peptide (1-44) inhibited cardiac hypertrophy (FIG. 20).

ii) Cardiac Function

During the observation period, LVEF remained at a value of 70% or more in all groups (no significant differences between the groups).

iii) Ventricular Wall Thickness

Figure 21:
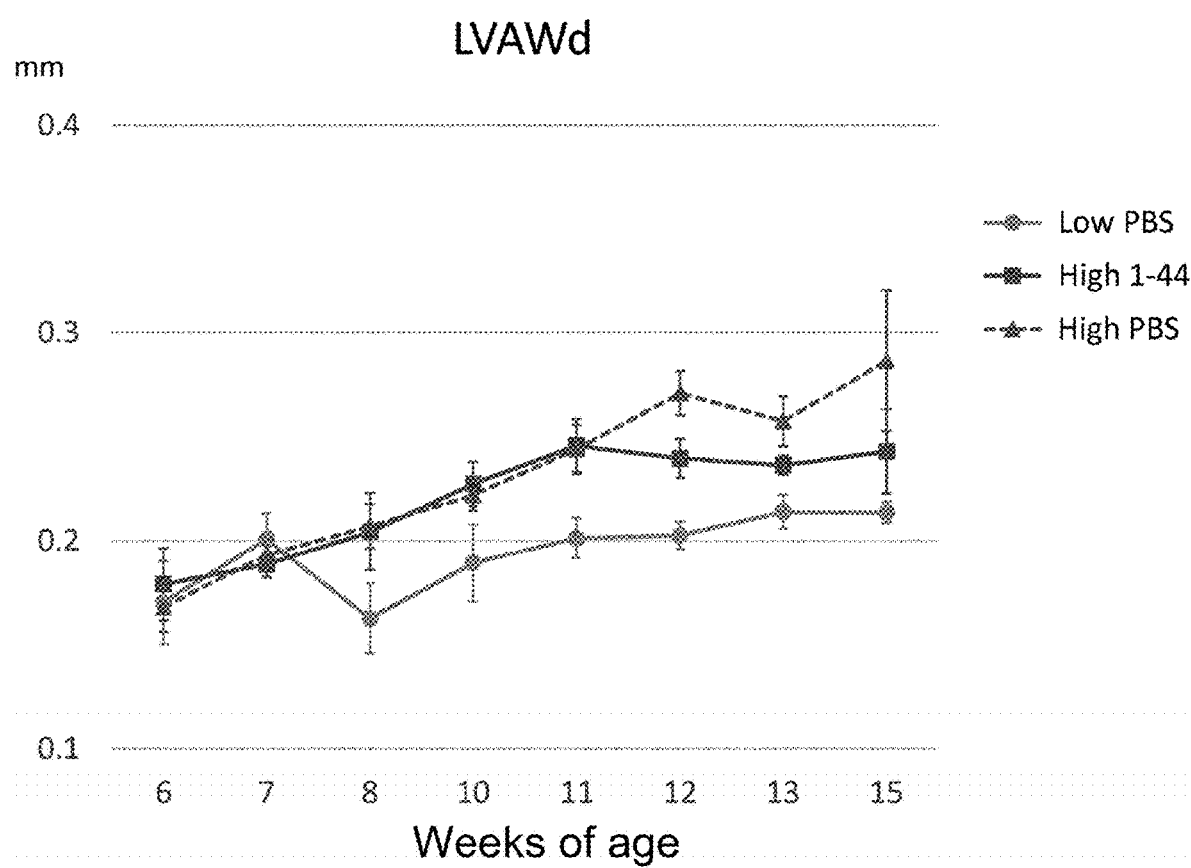
FIG. 21 presents a graph showing the transition of LVAWd from 6 weeks of age to 15 weeks of age (however, no measurements were taken at 9 and 14 weeks of age).

The changes in LVAWd during the observation period are shown in FIG. 21. At 15 weeks of age, the LVAWd of the High-PBS and High-1-44 groups were greater than that of the Low-PBS group, but the LVAWd of the High-1-44 group was smaller than that of the High-PBS group, showing the tendency for the increase of the left ventricular anterior wall thickness to be inhibited by administration of the HMGB1 peptide (1-44).

iv) Myocardial Fibrosis

Figure 22:
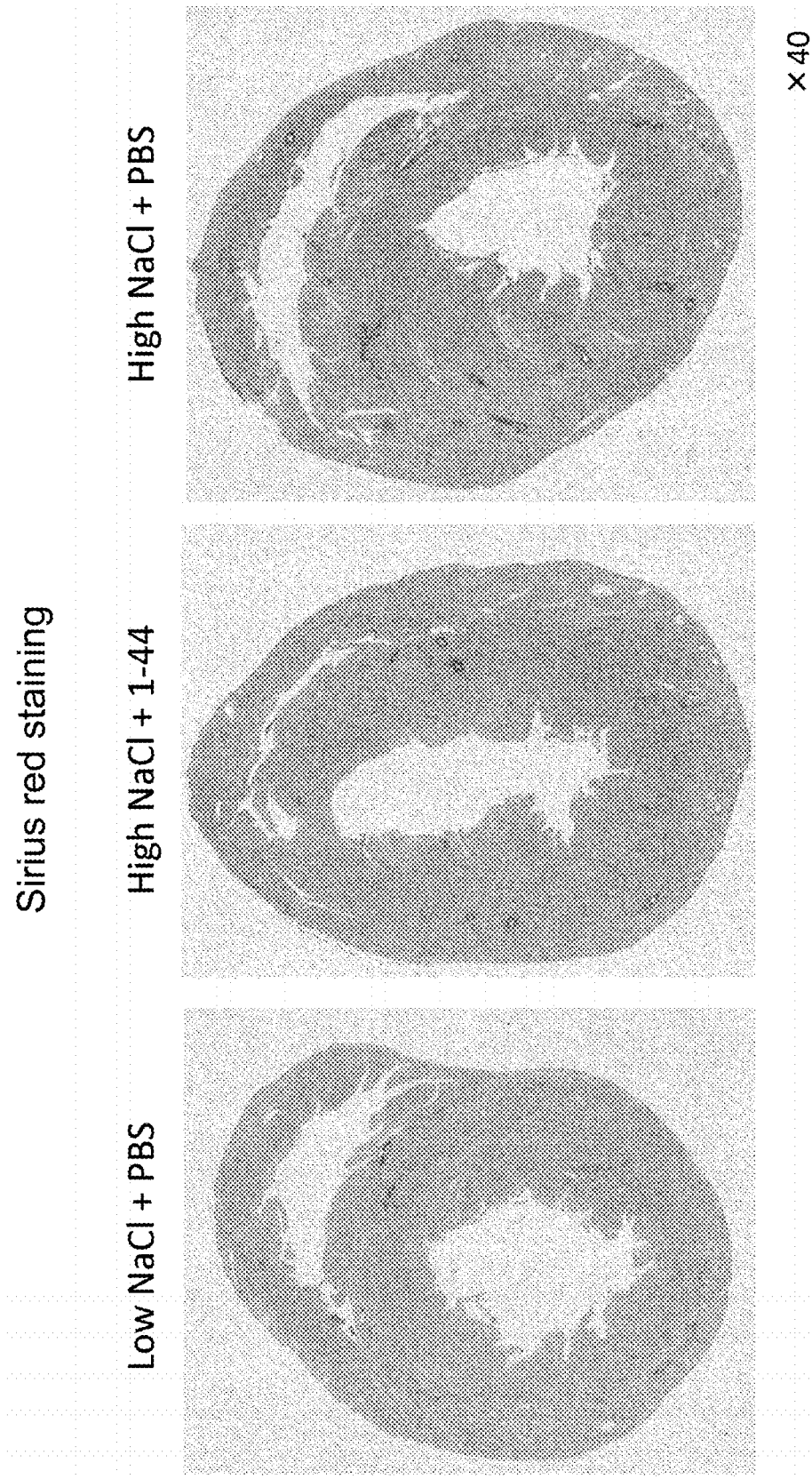
FIG. 22 is a photograph showing the results of Sirius red staining of myocardial tissue sections.
Figure 23:
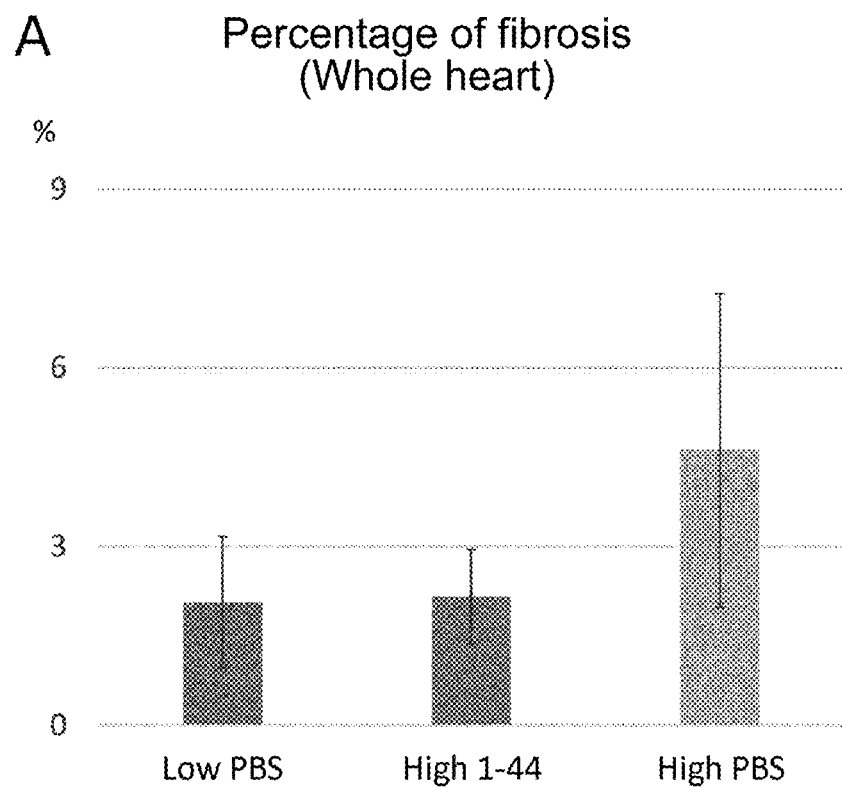
FIG. 23 presents graphs showing the percentage of area positively stained with Sirius red in myocardial tissue sections. All p values between groups are 0.1 or more, except those shown in the figure.
Figure 23:
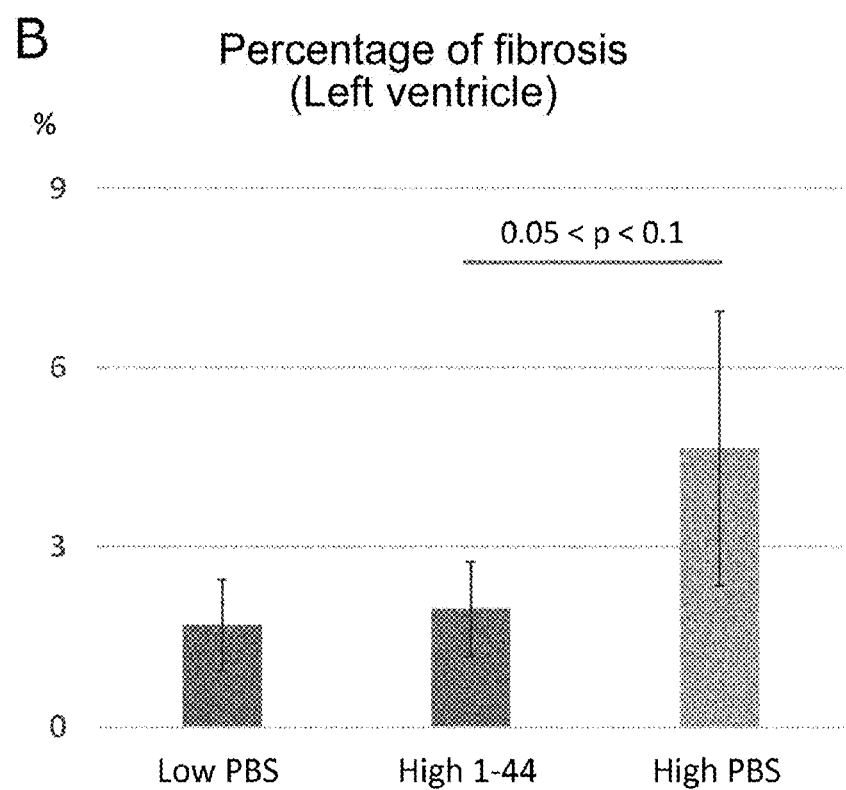

The results of Sirius red staining of the myocardial tissue sections are shown in FIG. 22. Compared with the Low-PBS group, the High-PBS group had increased fibrosis around the coronary arteries. The percentage of Sirius red-stained positive area (percentage of fibrosis) in the whole heart was smaller in the High-1-44 group than in the High-PBS group, showing the tendency for fibrosis of the myocardium to be inhibited by the administration of the HMGB1 peptide (1-44) (FIG. 23A). The percentage of fibrosis in the left ventricle was smaller in the High-1-44 group than in the High-PBS group, indicating that myocardial fibrosis was inhibited by the administration of the HMGB1 peptide (1-44) (FIG. 23B).

(4) Discussion

DIS/Eis rats fed with a high-salinity diet develop hypertension. It was also confirmed that the rats actually developed cardiac hypertrophy and cardiomyocyte hypertrophy. Therefore, the high-salinity diet-fed DIS/Eis rats used in the examples can be evaluated as a model of hypertensive cardiomyopathy.

Cardiac hypertrophy/cardiomyocyte hypertrophy is a structural abnormality that results in a reduced diastolic capacity of the heart. The high-salinity diet-fed DIS/Eis rats used in the present examples can also be evaluated as an HFpEF model because they developed cardiac hypertrophy/cardiomyocyte hypertrophy while maintaining normal left ventricular contractility.

The HMGB1 peptide (1-44) of the present invention inhibits cardiac hypertrophy and cardiomyocyte hypertrophy in high-salinity diet-fed DIS/Eis rats and thus can be used for the prevention and/or treatment of hypertensive cardiomyopathy and HFpEF.

INDUSTRIAL APPLICABILITY

Pharmaceutical compositions comprising a peptide of the present application are useful as pharmaceutical compositions for the prevention and/or treatment of cardiac diseases accompanied by structural abnormalities and/or dysfunction of the heart. The pharmaceutical compositions comprising a peptide of the present application are expected to provide great benefits to patients with cardiomyopathy and old myocardial infarction and chronic heart failure caused thereby, who are difficult to be operated due to factors such as advanced age, and who cannot receive a sufficient effect with existing drugs for chronic heart failure. In addition, the pharmaceutical compositions comprising a peptide of the present application exert effects such as improvement of the cardiac function and inhibition of cardiomyocyte hypertrophy in multiple cardiomyopathy models that are dilated cardiomyopathy, ischemic cardiomyopathy, and hypertensive cardiomyopathy, and thus they can be expected to exhibit broad therapeutic effects on various types of cardiomyopathy including idiopathic and secondary cardiomyopathies.

The invention claimed is:

1. A method of treating cardiomyopathy, wherein the method comprises identifying a subject with cardiomyopathy and administering to the subject an effective amount of a peptide, wherein the peptide is selected from the group consisting of:
   (a) a peptide consisting of the amino acid sequence described in SEQ ID NO: 1;
   (b) a peptide consisting of an amino acid sequence and having an activity of stimulating migration of mesenchymal stem cells, wherein the amino acid sequence results from substitution, deletion, insertion, or addition of one amino acid in the amino acid sequence described in SEQ ID NO: 1;
   (c) a peptide consisting of an amino acid sequence that shares 97% or more sequence identity with the amino acid sequence described in SEQ ID NO: 1 and having an activity of stimulating migration of mesenchymal stem cell; and
   (d) a peptide consisting of an amino acid sequence and having an activity of stimulating migration of mesenchymal stem cells, wherein the amino acid sequence results from addition of one or two amino acids to the amino acid sequence described in SEQ ID NO: 1,
   wherein the subject with cardiomyopathy has a structural abnormality and dysfunction of the heart,
   wherein the structural abnormality of the heart is selected from the group consisting of cardiomegaly, cardiomyocyte hypertrophy, and myocardial fibrosis,
   wherein the dysfunction of the heart is selected from the group consisting of impaired contractility and impaired diastolic capacity, and
   wherein cardiomyopathy is selected from the group consisting of dilated cardiomyopathy, ischemic cardiomyopathy, and hypertensive cardiomyopathy.

2. The method of claim 1, wherein the substance is administered systemically to a site different from the cardiac tissue.

3. The method of claim 1, wherein the method further comprises evaluating a treatment effect and determining that the treatment effect does occur.

4. The method of claim 3, wherein the treatment effect comprises (i) inhibition of a structural abnormality of the heart selected from the group consisting of cardiomegaly, cardiomyocyte hypertrophy, and myocardial fibrosis, (ii) promotion of angiogenesis in the heart, or (iii) improvement of the contractility or diastolic capacity of the heart.

5. The method of claim 4, wherein the promotion of angiogenesis is caused by enhanced capillary density.

6. The method of claim 1, wherein the administration promotes angiogenesis in the heart of the subject.

7. The method of claim 1, wherein the peptide is selected from the group consisting of:
   (a) a peptide consisting of the amino acid sequence described in SEQ ID NO: 1;
   (b) a peptide consisting of an amino acid sequence and having an activity of stimulating migration of mesenchymal stem cells, wherein the amino acid sequence results from substitution, deletion, insertion, or addition of one amino acid in the amino acid sequence described in SEQ ID NO: 1; and
   (c) a peptide consisting of an amino acid sequence that shares 97% or more sequence identity with the amino acid sequence described in SEQ ID NO: 1 and having an activity of stimulating migration of mesenchymal stem cells.

8. The method of claim 1, wherein the peptide is selected from the group consisting of:
   (a) a peptide consisting of the amino acid sequence described in SEQ ID NO: 1; and
   (b) a peptide consisting of an amino acid sequence and having an activity of stimulating migration of mesenchymal stem cells, wherein the amino acid sequence results from addition of one or two amino acids to the amino acid sequence described in SEQ ID NO: 1.

9. The method of claim 1, wherein the peptide is selected from the group consisting of:
   (a) a peptide consisting of the amino acid sequence described in SEQ ID NO: 1; and
   (b) a peptide consisting of an amino acid sequence and having an activity of stimulating migration of mesenchymal stem cells, wherein the amino acid sequence results from addition of one amino acid in the amino acid sequence described in SEQ ID NO: 1.

10. The method of claim 1, wherein the peptide is a peptide consisting of the amino acid sequence described in SEQ ID NO: 1.

11. The method of claim 1, wherein cardiomyopathy is dilated cardiomyopathy.

12. The method of claim 1, wherein cardiomyopathy is ischemic cardiomyopathy.

13. The method of claim 1, wherein cardiomyopathy is hypertensive cardiomyopathy.

14. A method of inhibiting a structural abnormality of the heart in cardiomyopathy, wherein the method comprises identifying a subject with cardiomyopathy and administering to the subject an effective amount of a peptide, wherein the peptide is selected from the group consisting of:
   (a) a peptide consisting of the amino acid sequence described in SEQ ID NO: 1;
   (b) a peptide consisting of an amino acid sequence and having an activity of stimulating migration of mesenchymal stem cells, wherein the amino acid sequence results from substitution, deletion, insertion, or addition of one amino acid in the amino acid sequence described in SEQ ID NO: 1;
(c) a peptide consisting of an amino acid sequence that shares 97% or more sequence identity with the amino acid sequence described in SEQ ID NO: 1 and having an activity of stimulating migration of mesenchymal stem cells; and
(d) a peptide consisting of an amino acid sequence and having an activity of stimulating migration of mesenchymal stem cells, wherein the amino acid sequence results from addition of one or two amino acids to the amino acid sequence described in SEQ ID NO: 1,
wherein the structural abnormality of the heart in cardiomyopathy is selected from the group consisting of cardiomegaly, cardiomyocyte hypertrophy, and myocardial fibrosis, and
wherein cardiomyopathy is selected from the group consisting of dilated cardiomyopathy, ischemic cardiomyopathy, and hypertensive cardiomyopathy.

15. The method of claim 14, wherein the substance is administered systemically to a site different from the cardiac tissue.

16. The method of claim 14, wherein the method further comprises evaluating inhibition of the structural abnormality of the heart in cardiomyopathy and determining that the inhibition does occur.

17. The method of claim 14, wherein the administration promotes angiogenesis in the heart of the subject.

18. The method of claim 14, wherein the peptide is a peptide consisting of the amino acid sequence described in SEQ ID NO: 1.

19. A method of promoting angiogenesis in the heart in cardiomyopathy, wherein the method comprises identifying a subject with cardiomyopathy and administering to the subject an effective amount of a peptide, wherein the peptide is selected from the group consisting of:
(a) a peptide consisting of the amino acid sequence described in SEQ ID NO: 1;
(b) a peptide consisting of an amino acid sequence and having an activity of stimulating migration of mesenchymal stem cells, wherein the amino acid sequence results from substitution, deletion, insertion, or addition of one amino acid in the amino acid sequence described in SEQ ID NO: 1;
(c) a peptide consisting of an amino acid sequence that shares 97% or more sequence identity with the amino acid sequence described in SEQ ID NO: 1 and having an activity of stimulating migration of mesenchymal stem cells; and
(d) a peptide consisting of an amino acid sequence and having an activity of stimulating migration of mesenchymal stem cells, wherein the amino acid sequence results from addition of one or two amino acids to the amino acid sequence described in SEQ ID NO: 1,
wherein the subject with cardiomyopathy has a structural abnormality and dysfunction of the heart,
wherein the structural abnormality of the heart is selected from the group consisting of cardiomegaly, cardiomyocyte hypertrophy, and myocardial fibrosis,
wherein the dysfunction of the heart is selected from the group consisting of impaired contractility and impaired diastolic capacity, and
wherein cardiomyopathy is selected from the group consisting of dilated cardiomyopathy, ischemic cardiomyopathy, and hypertensive cardiomyopathy.

20. The method of claim 19, wherein the substance is administered systemically to a site different from the cardiac tissue.

21. The method of claim 19, wherein the method further comprises evaluating promotion of angiogenesis in the heart in cardiomyopathy and determining that the promotion does occur.

22. The method of claim 21, wherein the promotion of angiogenesis is caused by enhanced capillary density.

23. The method of claim 19, wherein the peptide is a peptide consisting of the amino acid sequence described in SEQ ID NO: 1.

24. A method of improving the contractility or diastolic capacity of the heart in cardiomyopathy, wherein the method comprises identifying a subject with cardiomyopathy and administering to the subject an effective amount of a peptide, wherein the peptide is selected from the group consisting of:
(a) a peptide consisting of the amino acid sequence described in SEQ ID NO: 1;
(b) a peptide consisting of an amino acid sequence and having an activity of stimulating migration of mesenchymal stem cells, wherein the amino acid sequence results from substitution, deletion, insertion, or addition of one amino acid in the amino acid sequence described in SEQ ID NO: 1;
(c) a peptide consisting of an amino acid sequence that shares 97% or more sequence identity with the amino acid sequence described in SEQ ID NO: 1 and having an activity of stimulating migration of mesenchymal stem cells; and
(d) a peptide consisting of an amino acid sequence and having an activity of stimulating migration of mesenchymal stem cells, wherein the amino acid sequence results from addition of one or two amino acids to the amino acid sequence described in SEQ ID NO: 1,
wherein the subject with cardiomyopathy has a structural abnormality and dysfunction of the heart,
wherein the structural abnormality of the heart is selected from the group consisting of cardiomegaly, cardiomyocyte hypertrophy, and myocardial fibrosis,
wherein the dysfunction of the heart is selected from the group consisting of impaired contractility and impaired diastolic capacity, and
wherein cardiomyopathy is selected from the group consisting of dilated cardiomyopathy, ischemic cardiomyopathy, and hypertensive cardiomyopathy.

25. The method of claim 24, wherein the substance is administering systemically to a site different from the cardiac tissue.

26. The method of claim 24, wherein the method further comprises evaluating improvement of the contractility or diastolic capacity of the heart in cardiomyopathy and determining that the improvement does occur.

27. The method of claim 24, wherein the administration promotes angiogenesis in the heart of the subject.

28. The method of claim 24, wherein the peptide is a peptide consisting of the amino acid sequence described in SEQ ID NO: 1.

* * * * *